(12) United States Patent
Weindel et al.

(10) Patent No.: US 8,129,118 B2
(45) Date of Patent: Mar. 6, 2012

(54) MAGNETIC GLASS PARTICLES, METHOD FOR THEIR PREPARATION AND USES THEREOF

(75) Inventors: Kurt Weindel, Wielenbach-Hardt (DE); Michael Riedling, Penzberg (DE); Albert Geiger, Penzberg (DE)

(73) Assignee: Roche Diagnostics GmbH, Mannheim (DE)

( * ) Notice: Subject to any disclaimer, the term of this patent is extended or adjusted under 35 U.S.C. 154(b) by 158 days.

(21) Appl. No.: 11/128,024

(22) Filed: May 11, 2005

(65) Prior Publication Data

US 2005/0266462 A1 Dec. 1, 2005

Related U.S. Application Data

(60) Continuation of application No. 10/147,679, filed on May 16, 2002, now abandoned, and a continuation-in-part of application No. 11/041,750, filed on Jan. 24, 2005, which is a continuation of application No. 10/202,618, filed on Jul. 23, 2002, now abandoned, which is a division of application No. 09/756,743, filed on Jan. 10, 2001, now Pat. No. 6,870,047, which is a division of application No. 08/952,969, filed as application No. PCT/EP96/02459 on Jun. 6, 1996, now Pat. No. 6,255,477, application No. 11/128,024, which is a continuation-in-part of application No. 10/371,375, filed on Feb. 20, 2003, now Pat. No. 6,919,444, which is a continuation of application No. 09/856,737, filed as application No. PCT/EP99/08996 on Nov. 23, 1999, now Pat. No. 6,545,143.

(30) Foreign Application Priority Data

| Aug. 6, 1995 | (DE) | 195 20 398 |
| Oct. 12, 1995 | (DE) | 195 37 985 |
| Nov. 30, 1998 | (DE) | 198 54 973 |
| Nov. 30, 1998 | (DE) | 198 55 259 |
| Nov. 17, 1999 | (EP) | 99122853 |
| May 12, 2000 | (EP) | 00110165 |

(51) Int. Cl.
*C12Q 1/68* (2006.01)
*C12P 19/34* (2006.01)

(52) U.S. Cl. ............... 435/6.12; 435/91.2; 536/25.4

(58) Field of Classification Search ............ 435/6, 91.2, 435/6.12; 4/91.2; 536/25.4
See application file for complete search history.

(56) References Cited

U.S. PATENT DOCUMENTS

| 2,885,366 A | 5/1959 | Iler |
| 2,913,419 A | 11/1959 | Alexander |
| 3,926,659 A | 12/1975 | Bernhard et al. |
| 3,945,862 A | 3/1976 | Lee et al. |
| 4,082,905 A | 4/1978 | Stephan et al. |
| 4,124,385 A | 11/1978 | O'Horo |
| 4,124,735 A | 11/1978 | O'Horo |
| 4,126,437 A | 11/1978 | O'Horo |
| 4,233,169 A | 11/1980 | Beall et al. |
| 4,280,918 A | 7/1981 | Homola et al. |
| 4,297,337 A | 10/1981 | Mansfield et al. ............. 424/1 |
| 4,309,459 A | 1/1982 | Tokuoka |
| 4,336,310 A | 6/1982 | Okuyama et al. |
| 4,360,441 A | 11/1982 | Borrelli et al. |
| 4,395,271 A | 7/1983 | Beall et al. |
| 4,477,492 A | 10/1984 | Bergna et al. ............. 427/215 |
| 4,554,088 A | 11/1985 | Whitehead et al. ........ 252/62.54 |
| 4,564,537 A | 1/1986 | Austin et al. |
| 4,628,037 A | 12/1986 | Chagnon et al. |
| 4,672,040 A | 6/1987 | Josephson |
| 4,683,195 A | 7/1987 | Mullis et al. ............. 435/6 |
| 4,683,202 A | 7/1987 | Mullis et al. |
| 4,695,392 A | 9/1987 | Whitehead et al. |
| 4,695,393 A | 9/1987 | Chagnon et al. |
| 4,698,302 A | 10/1987 | Whitehead et al. |
| 4,699,717 A | 10/1987 | Riesner et al. |
| 4,751,211 A | 6/1988 | Fleming |
| 4,767,670 A | 8/1988 | Cox et al. |
| 4,804,561 A | 2/1989 | Tanioka et al. |
| 4,824,712 A | 4/1989 | Falleroni et al. |
| 4,910,148 A | 3/1990 | Sørensen et al. ............ 435/317.1 |
| 5,028,360 A | 7/1991 | Ito et al. |
| 5,041,390 A * | 8/1991 | Skov et al. ............. 436/527 |
| 5,055,194 A | 10/1991 | Goetz et al. |
| 5,057,426 A | 10/1991 | Henco et al. |
| 5,075,430 A | 12/1991 | Little |
| 5,076,950 A | 12/1991 | Ullman et al. |
| 5,155,018 A | 10/1992 | Gillespie et al. |

(Continued)

FOREIGN PATENT DOCUMENTS

CA 2223821 6/1996

(Continued)

OTHER PUBLICATIONS

From http://users.rcn.com/jkimball.maultranet/BiologyPages/N/Noncovalent.html, Noncovalent Bonding.*
Boom et al. J. of Clinical Microbiology, 1990, vol. 28 (3), p. 495-503.*
Marko et al. (Analytical Biochemistry, 1982, vol. 121, p. 382-387.*
Alderton et al., "Magnetic Bead Purification of M13 DNA Sequencing Templates," *Analytical Biochemistry*, vol. 201, 166-169, 1992.
Chou et al., "Prevention of pre-PCR MIS-Priming and Primer Dimerization Improves Low-Copy-Number Amplifications," *Nucleic Acids Research*, vol. 20, No. 7, 1717-1723, 1992.
Dang et al., "Oligonucleotide Inhibitors of Taq DNA Polymerase Facilitate Detection of Low Copy Number Targets by PCR," *JMB*, vol. 264, 268-278, 1996.
Jakobi et al., "Filter-Supported Preparation of λ Phage DNA," *Analytical Biochemistry*, vol. 175, 196-201, 1988.

(Continued)

*Primary Examiner* — Kenneth R. Horlick
*Assistant Examiner* — Joyce Tung
(74) *Attorney, Agent, or Firm* — Kilpatrick Townsend & Stockton LLP

(57) ABSTRACT

This invention relates to magnetic particles having a glass surface which are substantially spherical. This invention also relates to methods for making them, as well as to suspensions thereof and their uses for the purification of DNA or RNA in particular in automated processes.

17 Claims, 17 Drawing Sheets

U.S. PATENT DOCUMENTS

Figure 1:
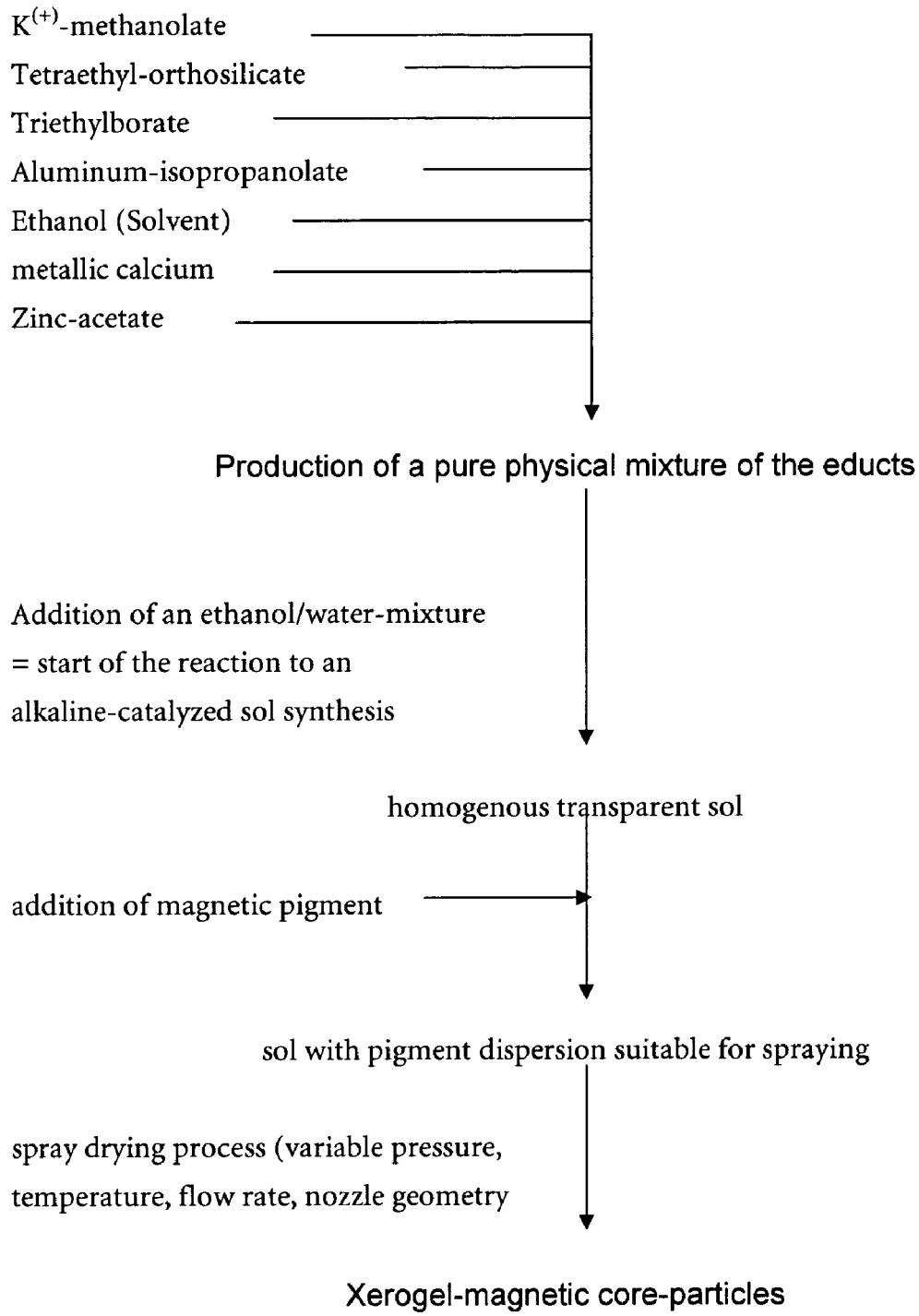

| | | | |
|---|---|---|---|
| 5,206,568 A | 4/1993 | Björnson et al. | |
| 5,210,015 A | 5/1993 | Gelfand et al. | 435/6 |
| 5,217,804 A | 6/1993 | James et al. | |
| 5,234,809 A | 8/1993 | Boom et al. | |
| 5,236,623 A | 8/1993 | Chevallier | |
| 5,279,936 A | 1/1994 | Vorpahl | |
| 5,312,485 A | 5/1994 | Wason et al. | |
| 5,316,699 A | 5/1994 | Ritter et al. | |
| 5,340,393 A | 8/1994 | Jacobson | |
| 5,346,994 A | 9/1994 | Chomczynski | |
| 5,352,645 A | 10/1994 | Schwartz | |
| 5,368,933 A | 11/1994 | Aoki et al. | |
| 5,389,482 A | 2/1995 | Okano et al. | |
| 5,395,498 A | 3/1995 | Gombinsky et al. | |
| 5,039,559 A | 8/1995 | Sang et al. | |
| 5,438,127 A | 8/1995 | Woodard et al. | 536/25.4 |
| 5,443,791 A | 8/1995 | Cathcart et al. | |
| 5,458,813 A | 10/1995 | Palladino et al. | |
| 5,470,660 A | 11/1995 | Misawa et al. | |
| 5,487,972 A | 1/1996 | Gelfand et al. | 435/6 |
| 5,503,816 A | 4/1996 | Woodard et al. | |
| 5,512,332 A | 4/1996 | Liberti et al. | |
| 5,512,405 A | 4/1996 | Misawa et al. | |
| 5,520,899 A | 5/1996 | Woodard et al. | 435/277 |
| 5,578,179 A * | 11/1996 | Demorest et al. | 204/451 |
| 5,578,238 A | 11/1996 | Weiss et al. | |
| 5,582,988 A | 12/1996 | Backus et al. | |
| 5,597,531 A | 1/1997 | Liberti et al. | |
| 5,599,627 A | 2/1997 | Aoki et al. | |
| 5,610,274 A * | 3/1997 | Wong | 530/334 |
| 5,648,170 A | 7/1997 | Okano et al. | |
| 5,658,548 A | 8/1997 | Padhye et al. | |
| 5,660,984 A | 8/1997 | Davis et al. | |
| 5,662,824 A | 9/1997 | Sang et al. | |
| 5,665,554 A | 9/1997 | Reeve et al. | |
| 5,681,946 A | 10/1997 | Reeve | |
| 5,683,875 A | 11/1997 | Lichtenwalter | |
| 5,693,502 A | 12/1997 | Gold et al. | 435/91.2 |
| 5,693,785 A | 12/1997 | Woodward et al. | |
| 5,698,271 A | 12/1997 | Liberti et al. | |
| 5,705,137 A | 1/1998 | Goerl et al. | |
| 5,705,628 A * | 1/1998 | Hawkins | 536/25.4 |
| 5,734,020 A | 3/1998 | Wong | |
| 5,747,663 A | 5/1998 | Colpan et al. | |
| 5,763,173 A | 6/1998 | Gold et al. | 435/6 |
| 5,783,686 A | 7/1998 | Gonzalez | |
| 5,804,375 A | 9/1998 | Gelfand et al. | 435/6 |
| 5,817,327 A * | 10/1998 | Ducheyne et al. | 424/425 |
| 5,898,071 A | 4/1999 | Hawkins | 536/25.4 |
| 5,904,848 A | 5/1999 | Wong et al. | |
| 5,925,573 A | 7/1999 | Collins et al. | 436/525 |
| 5,928,958 A | 7/1999 | Pilgrimm | 435/526 |
| 5,945,525 A | 8/1999 | Uematsu et al. | |
| 5,972,721 A | 10/1999 | Bruno et al. | |
| 5,990,301 A | 11/1999 | Colpan et al. | |
| 5,990,479 A | 11/1999 | Weiss et al. | |
| 6,027,945 A | 2/2000 | Smith et al. | |
| 6,136,083 A | 10/2000 | Schmidt et al. | |
| 6,255,477 B1 | 7/2001 | Kleiber et al. | |
| 6,274,386 B1 | 8/2001 | Hartig et al. | |
| 6,296,937 B2 | 10/2001 | Pryor et al. | |
| 6,368,800 B1 | 4/2002 | Smith et al. | |
| 6,870,047 B2 | 3/2005 | Kleiber et al. | |
| 6,919,444 B2 | 7/2005 | Harttig et al. | |
| 7,371,830 B2 | 5/2008 | Kleiber et al. | |
| 2003/0096984 A1 | 5/2003 | Cully et al. | |
| 2003/0096987 A1 | 5/2003 | Uematsu et al. | 536/25.4 |
| 2003/0199078 A1 | 10/2003 | Kleiber et al. | |

FOREIGN PATENT DOCUMENTS

| | | | |
|---|---|---|---|
| DE | 43 07 262 | | 11/1994 |
| DE | 195 20 964 | | 12/1996 |
| DE | 195 37 985 | A1 | 4/1997 |
| DE | 198 54 973 | * | 5/2000 |
| EP | 0 343 934 | A2 * | 5/1989 |
| EP | 0 343 934 | A2 | 11/1989 |
| EP | 0 389 063 | A2 | 9/1990 |
| EP | 0 125 995 | | 11/1991 |
| EP | 0 652 490 | | 5/1995 |
| EP | 0 757 106 | A2 | 7/1996 |
| EP | 0 757 106 | A3 | 2/1997 |
| EP | 0 811 694 | | 10/1997 |
| EP | 0 866 071 | A2 | 3/1998 |
| EP | 0 866 071 | A3 | 9/1998 |
| EP | 0 937 497 | A2 | 12/1998 |
| EP | 0 937 497 | A2 | 8/1999 |
| EP | 1 281 716 | B1 | 2/2003 |
| GB | 2 116 206 | A | 9/1993 |
| JP | 60-81012 | A | 5/1985 |
| JP | 62-1807 | A | 1/1987 |
| JP | 2-275713 | A | 11/1990 |
| JP | 4-31311 | A | 2/1992 |
| JP | 5281778 | | 10/1993 |
| JP | 7235407 | | 9/1995 |
| JP | 9-328311 | A | 12/1997 |
| JP | 9327291 | | 12/1997 |
| JP | 9327390 | | 12/1997 |
| WO | WO 83/03363 | | 10/1983 |
| WO | WO 88/06633 | | 9/1988 |
| WO | WO 89/01035 | A1 | 2/1989 |
| WO | WO 91/02811 | | 3/1991 |
| WO | WO 91/12079 | | 8/1991 |
| WO | WO 92/02638 | | 2/1992 |
| WO | WO 93/10162 | | 5/1993 |
| WO | WO 95/04140 | A1 | 2/1995 |
| WO | WO 95/06652 | | 3/1995 |
| WO | WO 96/03653 | | 2/1996 |
| WO | WO 96/11054 | | 4/1996 |
| WO | WO 96/41811 | | 12/1996 |
| WO | WO 96/41840 | | 12/1996 |
| WO | WO 97/10331 | | 3/1997 |
| WO | WO 97/10359 | | 3/1997 |
| WO | WO 97/29825 | | 8/1997 |
| WO | WO 98/31461 | | 7/1998 |
| WO | WO 98/31480 | | 7/1998 |
| WO | WO 99/16781 | | 4/1999 |
| WO | WO 99/26605 | | 6/1999 |
| WO | WO 00/32762 | | 11/1999 |
| WO | WO 99/67371 | | 12/1999 |
| WO | WO 00/32762 | A1 | 6/2000 |
| WO | WO 01/37291 | | 5/2001 |
| WO | WO 01/37291 | A1 | 5/2001 |

OTHER PUBLICATIONS

Marko et al., "A Procedure for the Large-Scale Isolation of Highly Purified Plasmid DNA Using Alkaline Extraction and Binding to Glass Powder," *Analytical Biochemistry*, vol. 121, 382-387, 1982.

Scalice et al., "Monoclonal Antibodies Prepared Against the DNA Polymerase From *Thermus aqualicus* are Potent Inhibitors of Enzyme Activity," *Journal of Immunological Methods*, vol. 172, 147-163, 1994.

Vogelstein et al., "Preparative and Analytical Purification of DNA From Agarose," *Proc. Natl. Acad. Sci. USA*, vol. 76, No. 2, 615-619, 1979.

Office Action dated Sep. 16, 2006 from U.S. Appl. No. 10/426,641, 5 pages.

Office Action dated May 30, 2007 from U.S. Appl. No. 10/426,641, 6 pages.

Office Action dated Jan. 2, 2008 from U.S. Appl. No. 10/426,641, 4 pages.

Office Action dated Jul. 11, 2008 from U.S. Appl. No. 10/426,641, 6 pages.

Office Action dated Feb. 24, 2009 from U.S. Appl. No. 10/426,641, 5 pages.

Office Action dated Jul. 31, 2009 from U.S. Appl. No. 10/426,641, 5 pages.

Office Action dated Mar. 16, 2010 from U.S. Appl. No. 10/426,641, 7 pages.

Alderton, R., et al, 1992, "Magnetic Bead Purification of M13 DNA Sequencing Templates", *Analytical Biochemistry*, (201):166-169.

Chou, Q., et al, 1992, "Prevention of pre-PCR mis-priming and primer dimerization improves low-copy-number amplifications", *Nucleic Acids Research*, 20 (7):1717-1723.

Dang, C., et al, 1996, "Oligonucleotide Inhibitors of Taq DNA Polymerase Facilitate Detection of Low Copy Number Targets by PCR", *J. Mol. Biol*, 264:268-278.

Jakobi, R., et al, 1988, "Filter-Supported Preparation of λ Phage DNA", *Analytical Biochemistry*, 175:196-201.

Marko, M., et al, 1982, "A Procedure for the Large-Scale Isolation of Highly Purified Plasmid DNA Using Alkaline Extraction and Binding to Glass Powder", *Analytical Biochemistry*, 121:382-387.

Scalice, E., et al, "Monoclonal antibodies prepared against the DNA polymerase from *Thermus acquaticus* are potent inhibitors of enzyme activity", *Journal of Immunological Methods*, 172:147-163, 1994.

Vogelstrein B, et al, 1979, "Preparative and analytical purification of DNA from agarose", *Proc. Natl. Acad. Sci. USA*, 78 (2):615-619.

BioRobot 9600 "The BioRobot 9600—An integrated, compact workstation for nucleic acid purification", Qiagen Product Guide (1997) 100-103.

Merel et al., "Completely automated extraction of DNA from whole blood", Clin Chem, (1996) 1285-6.

Yasumasa Goto, Japanese Journal of Applied Physics, "The Effect of Squeezing on the Phase Transformation and Magnetic Properties of ÿ-Fe2O3", vol. 3, No. 12, Dec. 1964, pp. 739-744.

Ullmann's Encyclopedia of Industrial Chemistry, Fifth Completely Revised Edition, vol. B2, Unite Operations I, pp. 19-1 through 19-3, vol. A 16, pp. 1-4, 1999.

Basic Inorganic Chemistry, 3rd Edition, 1995, p. 263.

Brooks et al., Communications of the American Ceramic Society, "Sol-Gel Coating of Lithium Zinc Ferrite Powders", Apr. 1991, pp. 851-853.

Hawkins et al., Nucleic Acids Research, "DNA Purification and Isolation Using A Solid-Phase", 1994, vol. 22, No. 21, pp. 4543-4544.

Kirk-Othmer Encyclopedia of Chemical Technology, Third Edition, "Boron Compounds", vol. 4, p. 67, 1984.

Boom et al., J. Clin. Microbiol. 28:495-503 (1990).

Jakobi et al., "Filter-Supported Preparation of Phage DNA," Anal. Biochem., vol. 175, 196-201, 1988.

Chapter 2 (DNA) and Chapter 4 (RNA) of F. Ausubel et al., eds., Current Protocols in Molecular Biology, Wiley-Interscience, New York (1993).

Chen et al., Anal. Biochem. 101:339-341 (1980).

Kirk-Othmer Encyclopedia-Chemical Technology, Fourth Edition, vol. 6, pp. 773-775, 1993.

Wirth et al., Science 275:44-47 (1997).

Database CAS online, AN 126:182277, Umatsu et al. 'Magnetic carriers for the separation of nucleic acids and methods of using them', Jpn. Kokai Tokkyo Koho, 9 pp. Jan. 21, 1997, abstract (EP 0 757 106 A2 corresponding thereto in English is enclosed).

Database CAS online, AN 126:86772, Kleiber et al. 'Magnetic particles and their use for isolation of biological material', Ger. Offen., 9 pp. Dec. 12, 1996, abstract.

Bischoff et al., "Nucleic Acid Resolution by Mixed-Mode Chromatography", J. Chromatog. (1984) 296:329-337.

Crowther et al., "High Performance Liquid Chromatographic Separation of Oligonucleotides and Other Nucleic Acid Constituents on Multifunctional Stationary Phases", J. Cromatog. (1983) 282:619-628.

Edwardson et al., "Separation and purification of oligonucleotides using a new bonded-phase packing material", J. Chromatog. (1991) 545:79-89.

Kirk-Othmer Encyclopedia of Chemical Technology, (1997) Fourth Edition, vol. 21, pp. 1021-1022.

Macherey-Nagel, Macherey-Nagel homepage on the Internet on Jun. 12, 1998, at http://www.machry-nagel.com.

McLaughlin, L., "Mixed-Mode Chromatography of Nucleic Acids", Chem Rev (1989) 89: 309-319.

Northrop et al., "Preparation and Evaluation of a Bimodal Size-Exclusion Chromatography Column Containing a Mixture of Two Silicas of Different Pore Diameter", Anal. Chem. (1991) 63:1350-1354.

Promega, Technical Bulletin No. 202 Wizard .RTM. Plus Series 9600 . TM. DNA Purification System, (Promega Corp.) (Sep. 1998).

Promega, Technical Bulletin No. 225 Wizard .RTM. Plus SV Minipreps DNA Purification System, (Promega Corp.) (Sep. 1999).

Promega, Technical Bulletin No. 259 Wizard .RTM. PureFection Plasmid DNA Purification System, (Promega Corp.) (Sep. 1999).

QuantiBlot, QuantiBlot Human DNA Quanitation System, PE Applied Biosystems, Feb. 5, 1996, pp. 1-5 (http://ww.pebio.com/fo/773503/773503.html).

* cited by examiner

Flow scheme for the preparation processing of the premature particles

Precondensation by temperature treatment (4h/200°C) in air for the stabilisation of the surface

↓

Final condensation and sintering under inert atmosphere (N₂) through treatment at high temperatures (1h, 750°C) => pigment cores surrounded by a weakly subcooled melt

↓

Rapid cooling => <u>m</u>agnetic pigment core-<u>g</u>lass coated-<u>p</u>article = <u>MGP</u>

↓

Temperature treatment in the air (4h, 200°C) = Oxidation of the glass shell

↓

Preparation of the non-aggregating fraction by the use of a sieve

↓

Bottling of the MGP powder, then 4h/200°C temperature treatment

↓

Cooling to approximately 80°C, Closing of the bottle with foil and screw top

↓

Storage of the MGP powder ==> Suspension in R-OH (e.g. isopropanol)

FIGURE 2

MAGNETIC GLASS PARTICLES, METHOD FOR THEIR PREPARATION AND USES THEREOF

This application is a continuation of U.S. application Ser. No. 10/147,679 filed May 16, 2002, now abandoned which claims the benefit of priority under 35 U.S.C. §119 of European application No. EP 00110165.8 filed. on May 12, 2000, and European application No. EP 99122853.7 filed on Nov. 17, 1999. This application is a continuation-in-part of U.S. application Ser. No. 11/041,750 filed Jan. 24, 2005, which is a continuation of U.S. application Ser. No. 10/202,618 filed Jul. 23, 2002, now abandoned which is a divisional of U.S. application Ser. No. 09/756,743 filed Jan. 10, 2001 (now U.S. Pat. No. 6,870,047), which is a divisional of U.S. application Ser. No. 08/952,969 filed Mar. 11, 1998 (now U.S. Pat. No. 6,255,477), which is a 35 U.S.C. §371 national phase filing of International Application No. PCT/EP96/02459 which was filed with the Patent Cooperation Treaty on Jun. 6, 1996 and is entitled to priority under 35 U.S.C. §119 to German Patent Applications 19537985.3 filed Oct. 12, 1995 and 19520398.4 filed Jun. 8, 1995. This application is a continuation-in-part of U.S. application Ser. No. 10/371,375 filed Feb. 20, 2003, now U.S. Pat. No. 6,919,444 which is a continuation of U.S. application Ser. No. 09/856,737 filed Jan. 9, 2002 (now U.S. Pat. No. 6,545,143), which is a 35 U.S.C. §371 national phase filing of International Application PCT/EP99/08996 which was filed with the Patent Cooperation Treaty on Nov. 23, 1999 and is entitled to priority under 35 U.S.C. §119 to German Patent Applications 198 55 259.9 and 198 54 973.3, both filed Nov. 30, 1998. All of the above cited applications are incorporated herein by reference.

BACKGROUND OF THE INVENTION

This invention relates to magnetic particles having a glass surface and are substantially spherical. This invention also relates to methods for making them, as well as to suspensions thereof and their uses for the purification of biological material in particular in automated processes.

Many biological materials, especially nucleic acids, present special challenges in terms of isolating them from their natural environment. On the one hand, they are often present in very small concentrations and, on the other hand, they are often found in the presence of many other solid and dissolved substances that make them difficult to isolate or to measure, in particular in biospecific assays.

Biospecific binding assays allow of the detection of specific analytes, e.g. nucleic acids, or specific analyte properties and play a major role in the field of diagnostics and bioanalytics. Examples therefor are hybridisation assays, immuno assays and receptor-ligand assays.

Hybridisation assays make use of the specific base-pairing for the molecular detection of nucleic acid analytes e.g. RNA and DNA. Hence, oligonucleotide probes with a length of 18 to 20 nucleotides may enable the specific recognition of a selected sequence in the human genome. Another assay which makes use of the selective binding of two oligonucleotide primers is the polymerase chain reaction (PCR) described in U.S. Pat. No. 4,683,195. This method makes use of the selective amplification of a specific nucleic acid region to detectable levels by a thermostable polymerase in the presence of desoxynucleotide triphosphates in several cycles.

Nucleic acids are comparatively complex analytes which have normally to be extracted from complex mixtures before they can be used in a probe-based assay.

There are several methods for the extraction of nucleic acids:
sequence-dependent or biospecific methods as e.g.:
affinity chromatography
hybridisation to immobilised probes on beads
sequence-independent or physico-chemical methods as e.g.:
liquid-liquid extraction with e.g. phenol-chloroform
precipitation with e.g. pure ethanol
extraction with filter paper
extraction with micelle-forming agents as cetyl-trimethyl-ammonium-bromide
binding to immobilised, intercalating dyes, e.g. acridine derivatives
adsorption to silica gel or diatomic earths
adsorption to magnetic glass particles (MGP) or organo silane particles under chaotropic conditions Many procedures and materials for isolating nucleic acids from their natural environment have been proposed in recent years by the use of their binding behavior to glass surfaces. In Proc. Natl. Acad. USA 76, 615-691 (1979), for instance, a procedure for binding nucleic acids in agarose gels in the presence of sodium iodide in ground flint glass is proposed.

The purification of plasmid DNA from bacteria on glass dust in the presence of sodium perchlorate is described in Anal. Biochem. 121, 382-387 (1982).

In DE-A 37 34 442, the isolation of single-stranded M13 phage DNA on glass fiber filters by precipitating phage particles using acetic acid and lysis of the phage particles with perchlorate is described. The nucleic acids bound to the glass fiber filters are washed and then eluted with a menthol-containing buffer in Tris/EDTA buffer.

A similar procedure for purifying DNA from lambda phages is described in Anal. Biochem. 175, 196-201 (1988).

The procedure known from the prior art entails the selective binding of nucleic acids to glass surfaces in chaotropic salt solutions and separating the nucleic acids from contaminants such as agarose, proteins or cell residue. To separate the glass particles from the contaminants according to the prior art, the particles are either centrifuged or fluids are drawn through glass fiber filters. This is a limiting step, however, that prevents the procedure from being used to process large quantities of samples.

It has been demonstrated that magnetic particles covered with a glass surface offer considerable advantages for isolating biological materials. If the magnetic particles have not been brought in contact with a magnetic field, gravity is the only force that can cause them to sediment out. They can be resuspended by shaking the solution.

The sedimentation procedure that does not utilize a magnetic field proceeds more slowly than the immobilization of biological materials on the surface of the particles. This is especially true for nucleic acids. The magnetic particles can be easily collected at a specific location in the sample fluid by means of a magnet. The fluid is then separated from the particles and, therefore, from the immobilized biological materials. The use of magnetic particles to immobilize nucleic acids after precipitation by adding salt and ethanol is described in Anal. Biochem. 201, 166-169 (1992) and PCT GB 91/00212. In this procedure, the nucleic acids are agglutinated along with the magnetic particles. The agglutinate is separated from the original solvent by applying a magnetic field and performing a wash step. After one wash step, the nucleic acids are dissolved in a Tris buffer. This procedure has a disadvantage, however, in that the precipitation is not selective for nucleic acids. Rather, a variety of solid and dissolved substances are agglutinated as well. As a result, this procedure can not be used to remove significant quantities of any inhibitors of specific enzymatic reactions that may be present. Magnetic, porous glass is also available on the market that contains magnetic particles in a porous, particular glass matrix and is covered with a layer containing streptavidin. This product can be used to isolate biological materials, e.g., proteins or nucleic acids, if they are modified in a complex preparation step so that they bind covalently to biotin.

Magnetizable particular adsorbents proved to be very efficient and suitable for automatic sample preparation. Ferrimagnetic and ferromagnetic as well as superparamagnetic pigments may be used for this purpose.

Particles, according to the expert, are solid materials having a small diameter. Particles like these are often also referred to as pigments.

Those materials are referred to as magnetic that are drawn to a magnet, i.e., ferromagnetic or superparamagnetic materials, for instance. Superparamagnetism is seen as advantageous and preferable in the state of the art (e.g. U.S. Pat. No. 5,928,958; U.S. Pat. No. 5,925,573; EP 757 106). The glass or organosilane surfaces are often functionalised in order to be used for biospecific capture reactions, e.g. U.S. Pat. Nos. 5,928,958, 5,898,071, 5,925,573, EP 937 497, U.S. Pat. Nos. 4,554,088 or 4,910,148. Alternatively, glass or organosilane surfaces may be treated with various solvents or salts to modify their hydrophilicity and/or electropositivity, e.g. U.S. Pat. No. 5,438,127.

However, the underivatized silanol groups of the glass or the silane surface may be used for the adsorption with pure physico-chemical forces under suitable reaction conditions as described in DE 195 20 964, DE 195 37 985, WO 96/41840, WO 96/41811, EP 757 106 or U.S. Pat. No. 5,520,899. Typically, magnetic cores or magnetic core aggregates are covered with a glass surface which is formed by an acid- or base-catalyzed sol-gel-process. These particles are called core-shell particles. The glass shell then has a typical layer thickness (see e.g. DE 195 20 964) wherein the size and shape of the pigment, which may contain a non-magnetic support as e.g. mica in addition to the magnetic metal oxide, determines size and form of the produced particle (see e.g. DE 195 37 985 and corresponding WO 96/41811). To obtain a high surface activity, glass material with a high porosity is used (see e.g. EP 757 106; WO 99/26605). Further, composite magnetic particles are described, e.g. silicate-covered ferric oxide covered with an inorganic silica matrix from silica particles (EP 757 106) or mixtures of glass and silica gel (WO95/06652).

DESCRIPTION OF THE INVENTION

The problem to be solved by the present invention can be seen as providing magnetic glass particles with improved properties for sample preparation and for biological assays, in particular for automated processes.

The deficiencies of the magnetic glass particles in the state of the art are overcome by the findings of the present invention.

It is an object of the invention to provide a composition of magnetic glass particles. The magnetic glass particles (MGPs) according to the present invention are a solid dispersion of small magnetic cores in glass. The MGPs are comparatively small and are substantially spherical. The non-magnetic fine content of a composition of the MPGs is very low because of the method of their preparation. This has the effect that suspensions of the MGPs sediment slowly and can therefore be advantageously used for processes in molecular biology which can be automated. In one embodiment of the invention compositions and suspensions of the MGPs according to the present invention are provided. In another embodiment of the invention a method for the composition of the MGPs is provided. In still another embodiment of the invention a method for the purification of DNA or RNA is provided in which the MGPs according to the present invention are used.

It is a object of the present invention to provide a composition of magnetic glass particles which are substantially spherical and have a small diameter and contain at least one magnetic object with a diameter between 5 and 500 nm. This has surprising consequences on the sedimentation kinetics, quantified by the half time values $t_{1/2}$, which is the time span until 50% of the particles have sedimented from a specific volume element (see Example 6). The half-life period for the sedimentation of a 3 mg/ml weight-per-volume suspension of the composition in isopropanol is more than 3 min, preferably 4 min, more preferably 6 min. However the most preferred values for the half-life period is more than 10 min or even more than 20 min. The smaller and closer to the ideal sphere, the longer the MGPs will be suspended. This may be explained by the fact that the closer the form will resemble an ideal sphere, the lower the possibility that two or more particles will stick together and built up aggregates which may sediment more rapidly. These data are shown in Example 6 and high resolution scanning electron microscopical images can be seen in FIG. 4 to FIG. 10. This has the advantage that for automated processes the required mixing intensity and mixing frequency of the storage containers containing the MGP suspension is reduced as the repetitive dosage of a specific MGP suspension volume from a surplus volume sucked into a syringe is easier (more precise delivery with regard to mass$_{MGP}$/volume).

The MGPs according to the present invention are glass droplets in which very small non-aggregating magnetic objects are dispersed. Those objects that are referred to as magnetic are drawn to a magnet, i.e., ferromagnetic or superparamagnetic materials, for instance. Preferred are ferromagnetic materials, in particular if they have not yet been premagnetized. Premagnetization in this context is understood to mean bringing in contact with a magnet, which increases the remanence. Preferred magnetic materials are iron or iron oxide as e.g. magnetite ($Fe_3O_4$) or $Fe_2O_3$, preferably $\gamma$-$Fe_2O_3$. In principle, barium ferrite, nickel, cobalt, Al—Ni—Fe—Co alloys or other ferri- or ferromagnetic could be used. The magnetic objects may be e.g. a magnetic pigment. The size of the magnetic objects is in the nanoscale range, i.e. according to the present invention the diameter is between 5 to 500 nm, preferably between 10 to 200 nm, most preferably between 15 to 50 nm. Suitable magnetic pigments are manufactured by the company CERAC which have a mean diameter of 23 nm and consist of $\gamma$-$Fe_2O_3$ (BET-surface 50 $m^2$/g, CERAC: P.O. Box 1178, Milwaukee, Wis. 53201-1178 USA; Article-No. I-2012). The magnetic glass particles according to the present invention are further characterized by the fact that the MGPs have a particle diameter between 0.5 μm and 5 μm, preferably between 1 μm to 2 μm as determined by high resolution scanning electron microscopy, whereas the magnetic objects have a diameter between 5 to 500 nm, preferably between 10 to 200 nm, most preferably in the range of 15 to 50 nm as said above. Hence, the MGPs of the present invention are further characterized by a diameter ratio of magnetic pigment core to magnetic glass particle of less than 1 to 10 as determined by high resolution scanning electron microscopy. Because of these diameter ratios as well as the absence of any inert carrier that would determine shape and size of the particles, the geometry of the MGPs and the number of incorporated magnetic objects, are determined by the conditions of manufacturing. The MGPs according to the present invention are microporous but have highly-structured and therefore relatively large surface with more than 6 m²/g. Preferably, the magnetic glass particles according to the present invention have a surface area in the range of 5 to 100 m²/g, preferably 5 to 90 m²/g, more preferably in the range of 10 to 50 m²/g, most preferably in the range of 15 to 30 m²/g. This surface is approximately double the size of the particles described in DE 195 37 985. This can be determined by the Braunauer-Emett-Teller-method using an automated commercial apparatus (see Example 4). For a discussion of this method, familiarly called the BET method, see S. Braunauer. The Adsorption of Gases and Vapors, Vol. 1, Princeton University Press, 1943. For example, the sample EJ0096.5R-01 which is of preferential interest (see Example 1 and Table 1 to Table 3 for a summary of the production parameters) has a BET-surface of 26.8525 m²/g, a micropore area of 2.3058 m²/g and an average pore diameter of 24.9132 nm. This means that the pore surface is less than 10% of the total surface and that the magnetic glass particle is microporous.

A pore is understood to be a recess in the outer surface of the particle. The surface reaches so far into the particle that a perpendicular line drawn in the recess on the surface cuts the particle at least once in the direction of the adjacent environment of the particle. In addition, pores reach into the particle to a depth that is greater than one radius of the pore.

The slower sedimentation kinetics, larger surface and the aggregation-inhibiting spherical form manifest themselves in the better functional performance as adsorbent in the nucleic acid diagnosis (see Example 3, 5 and 7) when compared to the German patent applications DE 198 54 973.3 or DE 198 55 259.9. This criterion can be quantified by a shift of the threshold cycles in so-called TaqMan® assays, the signal-to-noise ratio and of the statistically validated lower detection limit. The methods for this assay are disclosed in WO92/02638 and the corresponding U.S. Pat. Nos. 5,210,015, 5,804,375, 5,487,972). Radiotracing experiments (see Example 5.2) showed that the binding behavior with regard to DNA and RNA was the same when compared to reference material known in the state of the art. Surprisingly, the production parameters had an influence on the performance in the radiotracing experiments. A further advantage of the MGP-type of the present invention is that no tensions in the glass layer can lead to fissure during the drying process and corresponding damages in the glass shell because of the inner structure (solid dispersion of small magnetic cores in a glass drop). This can be investigated by image-producing methods (see Example 3).

Another embodiment of the present invention is a suspension of magnetic particles. It is obvious for the person skilled in the art to produce a suspension by adding a liquid to a composition of the MGPs and mix the suspension to homogeneity. A liquid according to the present invention may comprise any liquid which does not affect the stability of the magnetic particles and may be used to produce a homogenous suspension. Preferably liquids are used which are suitable for processes in molecular biology, in particular desoxyribonucleic acid (DNA) or ribonucleic acid (RNA) purification processes which make use of the binding of these substances to glass particles under certain conditions. Preferred liquids comprise alcohols or any mixtures thereof with water or ketones. Alcohols shall include according to the invention preferably primary, secondary or tertiary alcohols of the general formula R—OH where the R stands for the general formula -(—CH2)$_n$—CH3 with n >=0. However, other alcohols can also be used if they are suitable for molecular biology purposes as e.g. glycerol. Particularly suitable are the alcohols isopropanol, ethanol or mixtures thereof with water, preferably a mixture of 80 volume parts of isopropanol with 20 volume parts of water(. In another embodiment of the invention the liquid comprises ketones as e.g. acetone. In a preferred embodiment of the invention these suspensions contain between 5 to 60 mg/ml MGPs. In another embodiment of the invention the MGPs are suspended in aqueous buffered solutions which may optionally contain a chaotropic agent in a concentration of between 2 and 8 mol/l, and preferably between 4 and 6 mol/l. Chaotropic salts can be sodium iodide, sodium perchlorate, guanidinium thiocyanate, guanidinium isothiocyanate or guanidinium hydrochlorite. Other compounds are also possible. A chaotropic agent according to the present invention will be any chemical substance which will disturb the ordered structure of liquid water and will have the effect that DNA or RNA will bind to the MGPs according to the present invention if this agent is present in the DNA or RNA containing solution. It is obvious for the artisan to produce suitable aqueous buffered solutions. Buffer systems which may be used for molecular biology purposes may be found e.g. in Sambrook et al. (1989), Molecular Cloning, Cold Spring Harbor University Press, New York, N.Y., USA. Preferred buffer substances are Tris-hydroxymethylamine (TRIS), phosphate, N-(2-Hydroxyethyl)piperazine-N'-(2-ethanesulfonic acid) (HEPES), salts thereof or other suitable substances. Additionally, substances may be present which modify the ionic strength of the solution as e.g. NaCl, KCl or $CaCl_2$ or which are metal cation complexing agents as e.g. ethylene-diamine-tetra-acetic acid (EDTA) or the salts thereof. Biological material known to the expert in the field may also be present. In another embodiment of the invention the suspension of MGPs may additionally contain DNA or RNA optionally in a mixture with proteins, fatty acids, carbohydrates and other material from biological origin. In another embodiment of the invention the liquid may contain a mixture of one or more constituents selected from the group of alcohols, ketones, aqueous buffered solutions, chaotropic agents, substances which modify the ionic strength of the solution, complexing agents, biological material, DNA or RNA all with the features as described above.

In another embodiment of the invention a tube or reaction vessel containing the suspension according to the invention is provided. The tube can be made of plastics but it may also be part of a larger structure, e.g. part of a microtitreplate in 96- or 384-well-format. In still another embodiment of the invention a storage container is provided which contains a composition of magnetic glass particles or suspensions thereof.

In another embodiment of the invention a kit of parts is provided which comprises a storage container containing the magnetic glass particles or a suspension thereof according to the present invention. The kit may be used for the purification of DNA or RNA. Such kits known in the art further comprise plastics ware which may be used during the purification procedure as e.g. microtitreplates in the 96 or 384 well format or just ordinary reaction tubes manufactured e.g. by Eppendorf, Hamburg, Germany. The kit may further comprise a washing solution which is suitable for the washing step of the magnetic glass particles when DNA or RNA is bound thereto. Often the washing solution is provided as a stock solution which has to be diluted before the use. The kit may further comprise an eluent, i.e. a solution or a buffer (e.g. TE, 10 mM Tris, 1 mM EDTA, pH 8.0) or pure water to elute the DNA or RNA bound to the magnetic glass particles. Further, additional reagents may be present which can be used for the purification process of a nucleic acid, i.e. DNA or RNA. In one embodiment of the invention the kit of parts according to the present invention is used for the purification of a nucleic acid.

In one embodiment of the invention the composition of MGPs may be used to produce a suspension as already described.

In another embodiment of the invention the suspensions according to the present invention may be used for the purification of nucleic acids, i.e. RNA or DNA, from complex mixtures with other biological substances containing them. Thereby also mixtures of different nucleic acids may be purified, even mixtures containing a nucleic acid of interest in low abundance. The purification effect results from the behavior of DNA or RNA to bind to magnetic glass particles under certain conditions e.g. in the presence of certain concentration of a chaotropic agent. Preferably, the MGPs with the bound DNA or RNA are washed afterwards at least once, preferably with a mixture of 70 volume parts ethanol with 30 volume parts water ("70% Ethanol"). Afterwards, the conditions are reversed, e.g. the concentration of the chaotropic agent is decreased, to elute the DNA or RNA bound to the MGP the particle. Preferably, this is done by the pelleting of the magnetic glass particles, e.g. by gravity force or by the use of a magnet, and resuspending in a solution with no or only a low amount of chaotropic agent. Alternatively, the solution can be diluted with a solution with no or only a low amount of chaotropic agent. The purified DNA or RNA can now be used for other reactions. It is one object of the invention to provide a production method for the MGPs according to the present invention. A glass according to the present invention is understood to be an amorphous material that contains silicium. Glass can contain other materials such as $B_2O_3$ (0-30%), $Al_2O_3$ (0-20%), CaO (0-20%), BaO (0-10%), $K_2O$ (0-20%), $Na_2O$ (0-20%), MgO (0-18%), $Pb_2O_3$ (0-15%). Glass can also contain a smaller percentage (0-5%) of a number of other oxides such as $Mn_2O_3$, $TiO_2$, $As_2O_3$, $Fe_2O_3$, CuO, CoO, etc.

Especially preferred according to the present invention are glasses that are formed using the gel sol process described in WO 96/41811 and then dried and compressed. The basic principles of this process are known and were described, for instance, in C. J. Brinker, G. W. Scherer "Sol Gel Science—The Physics and Chemistry of Sol Gel Processing", Academic Press Inc. 1990, Sol-Gel Optics, Processing and Applications, Lisa C. Klein, Ed., Kluwer Academic Publishers 1994, p. 450 ff., and in DE-A-1941191, DE-A-3719339, DE-A-4117041, DE-A-4217432 and WO96/41811. Principally, in the gel-sol process, alkoxides of network-forming components, e.g., $SiO_2$, $B_2O_3$, $Al_2O_3$, $TiO_2$, $ZrO_2$, $GeO_2$, are combined with oxides and salts of other components, e.g., in an alcohol solution, and then hydrolized. The equation below describes the procedure for making sodium boroaluminium silicate glass:

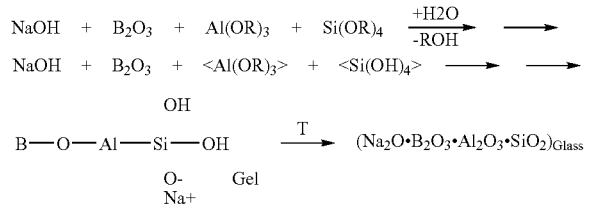

Water is added to begin the hydrolysis process of the starting components. The reaction proceeds relatively quickly because the alkali ions have a catalytic effect on the speed of hydrolysis of the silicic acid ester. Once the gel is formed it can be dried and densified (or condensed) by means of a thermal process to form glass.

In one embodiment of the invention the glass matrix will be produced by acid or base catalyzed sol-gel synthesis as shown schematically in FIG. 1 and FIG. 2 and described in detail in Example 1. Here, use is made of colloidal systems wherein at first the solid constituents are dispersed in the liquid phase (=sol) and after the processing they are interconnected like a honeycomb pattern (=gel). The composition of the glass (code EJ) as calculated from the quantity of the educts was 70.67 Mol % $SiO_2$, 14.33 Mol % $B_2O_3$, 5.00 Mol % $Al_2O_3$, 4.00 Mol % $K_2O$, 2.00 Mol % CaO, 4.00 Mol % ZnO. The composition of the glass (code RN) was 74 Mol % $SiO_2$, 15 Mol % $B_2O_3$, 5.00 Mol % $Al_2O_3$, 4.00 Mol % $K_2O$, 2.00 Mol % CaO. The composition of the glass (code EP) was 73.61 Mol % $SiO_2$, 14.93 Mol % $B_2O_3$, 5.21 Mol % $Al_2O_3$, 4.17 Mol % $K_2O$, 2.08 Mol % CaO.

The reaction may be described as follows: either acid-catalyzed, e.g.:

$$BCl_3 + 3H_2O \rightarrow B(OH)_3 + 3H^{(+)}Cl^{(-)}$$

$$AlCl_3 + 3H_2O \rightarrow Al(OH)_3 + 3H^{(+)}Cl^{(-)}$$

$$SiCl_4 + 4H_2O \rightarrow Si(OH)_4 + 4H^{(+)}Cl^{(-)}$$

$$Na^{(+)}NO_3^{(-)} + H_2O \rightarrow Na^{(+)}OH^{(-)+H(+)(-)}NO_3^{(-)}$$

$$K^{(+)(-)}OOCCH_3 + H_2O \rightarrow K^{(+)}OH^{(-)} + H^{(+)(-)}OOCCH_3$$

or alkaline-catalyzed, e.g.

$$K^{(+)(-)}OCH_2CH_3 + H_2O \rightarrow K^{(+)}OH^{(-)} + HOCH_2CH_3$$

$$Na^{(+)(-)}OCH_3 + H_2O \rightarrow Na^{(+)}OH^{(-)} + HOCH_3$$

$$Al^{(3+)}[^{(-)}OCH_2CH_2CH_3]_3 + 3H_2O \rightarrow Al(OH)_3 + 3HOCH_2CH_2CH_3$$

$$B(OCH_2CH_3)_3 + 3H_2O \rightarrow B(OH)_3 + 3HOCH_2CH_3$$

The diverse hydroxides condensate to the corresponding oxides which form a three-dimensional network, the amorphous glass matrix of $SiO_2/B_2O_3/Al_2O_3$ with metal ions occupying interstitial sites. In addition to the above-captioned alkaline and alkaline earth metal ions, transition metal ions as e.g. $Zn^{2+}$ and $Zr^{2+}$ may be incorporated in the matrix as network modifying agents.

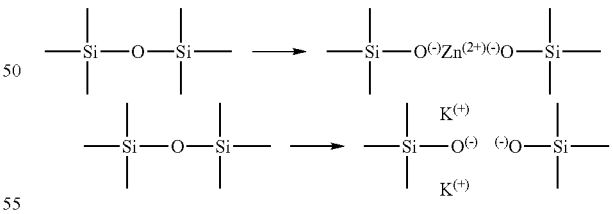

In another embodiment of the invention, the glass may be produced with methods known in the state of the art by the melting of the raw material $SiO_2$ and of carbonates of the alkali or alkaline earth metals $Na_2CO_3$, $K_2CO_3$ or $CaCO_3$ The reaction may be described as follows:

$$Na_2CO_3 + SiO_2 \rightarrow Na_2SiO_3 (=Na_2O \cdot SiO_2) + CO_2 \uparrow$$

$$K_2CO_3 + SiO_2 \rightarrow K_2SiO_3 (=K_2O \cdot SiO_2) + CO_2 \uparrow$$

$$CaCO_3 + SiO_2 \rightarrow CaSiO_3 (=CaO \cdot SiO_2) + CO_2 \uparrow$$

However in most cases, there is no pure silicate matrix but a borate-aluminate-silicate-matrix i.e. regarding the network building constituent a part of $SiO_2$ is substituted by $B_2O_3$ and $Al_2O_3$).

The sol:pigment ratio has a considerable effect on the yield of magnetic particles provided by this invention. It is essential for the process that the sol can still be pumped and sprayed which is in the skill of artisan.

To create a powder, the slurry is preferably sprayed through a two-fluid nozzle as described in FIG. 1 and in Example 1.3. Suitable spray-drying systems are produced by Nubilosa Molekularzerstäubung, Ladisch GmbH & Co. KG, Konstanz, Germany, e.g. the "Labor-Zerstäubungstrockner (Typ LTK)" or by Büchi AG, Uster, Switzerland, e.g. the Mini Spray Dryer (Type B-191).

Because of the diameter ratios of magnetic cores to the glass shell are less than 1 to 10, preferably between 1:10 and 1:1000, the geometry and the number of incorporated magnetic cores or of their inert carriers do not determine shape and size of the particles but the conditions of manufacturing, in particular the conditions during spray drying. In other words, the choice of pressure, inlet temperature, outlet temperature and flow rate during the spray drying procedure are the degrees of freedom which will determine the size distribution, the shape of the glass drops and thereby will modify the MGPs. When the spray pressure is increased, the size distribution will shift into the sub-β-range. The decreased temperature of the spray drying process will lead to slower evaporation of the solvent and thereby the form of the MGPs will come closer to an ideal sphere, i.e. the ratio of the radii in xy- and xz-plane will become approximately 1. The ratio of the radii will vary between 0.8 and 1.2, preferably between 0.9 and 1.1.

In a preferred embodiment of the invention the nozzles are heated. The inlet temperature is between 120° C. and 500° C., preferably between 170° C. and 230° C. or 150° C. and 230° C., most preferably between 150° C. and 200° C. or 190° C. and 210° C. or at 200° C. or slightly less. The outlet temperature depends on the boiling point of the sol and thereby on the solvent and may be above, equal or slightly under, i.e. less than 10° C., the boiling point of the solvent. When ethanol is used as solvent, it is between 50° C. and 300° C., preferably 70° C. and 150° C., most preferably between 80° C. and 110° C. The optimal temperature is between 90° C. to 100° C. The nozzle pressure is more than 3 bar, preferably it is regulated to 4 to 6 bar. The artisan will appreciate the fact that the exact parameters will depend on the spray-drying system used. However, he can transfer the teachings of the present invention to any other spray-drying and find out the parameters by taking the disclosures of this invention into account. Formula as described in Masters: Spray Drying Handbook, Fifth Edition, John Wiley & Sons, 1991, New York can lead him the way to find out which parameters have to be chosen for another setting. Preferably, he will question the manuals of his spray-drying system or contact the technical service of the spray-drying system manufacturer.

To optimize the yield, the densification or sinter temperature should be as high as possible, i.e. slightly below the melting range. If it is too high, however, the particles will stick together and form agglomerates that must be sieved out. If too low, the MGPs will not be optimally densified. Additional treatment of the particles at too high temperature will result in a loss of magnetic properties. Too high temperatures should therefore be omitted. The exact temperatures depend on the glass composition but may be between 400° C. to 1200° C. In the case of the EJ glass composition the sinter temperature is between 720° C. and 770° C., preferably around 750° C. It is in the skill of the artisan to find out the temperatures for each glass composition when taking the teachings of the present invention into account. According to the present invention, the spray-dried MGP powder may be further processed as depicted in FIG. 2 and described in Example 1.4. Preferably, the powder is heated for 1 hour to 200° C., optionally cooled to room temperature and heated to 750° C. (densification or sinter temperature) in a nitrogen atmosphere with a heating rate of 1 K/min and is held at that temperature for 1 hour. Then the furnace is cooled to 150° C. and heated again to 200° C. for one hour in air. After the cooling to room temperature, the powder is transferred to a sieve (50 μm) and sieved for 30 min. The sieved sample is bottled and sterilized at 200° C. for 4 h and then cooled to 80° C. Then the glass vessels are taken from the oven, covered with sterile foil and closed.

Surprisingly, the magnetic particles provided by the invention are especially suited for isolating biological materials from samples. In addition, the core material is a natural resource and therefore causes little ecological concern. Moreover, the particles according to the invention are inexpensive and easy to manufacture.

Another object of the invention is a procedure for isolating a biological material by bringing a sample containing the biological material in a liquid in contact with the magnetic particles according to the invention under conditions in which the biological material binds to the particle surface, and separating the biological material from the liquid. According to the invention the term "in a liquid" means that liquid may be added to the sample before the magnetic particles are added. However, it shall also comprise the situation when the sample itself has a low viscosity and is itself a liquid so that no additional liquid or buffer may have to be added to the sample for the sample preparation which may be done by adding solid agents before the magnetic glass particles are added. The order of reagent addition may be varied according to process requirements.

Biological materials are understood to mean materials with a particular or molecular basis. They include, in particular, cells such as viruses or bacteria, as well as isolated cells from multicellular organisms as e.g. human and animal cells such as leucocytes, and immunologically active low and high molecular chemical compounds such as haptens, antigens, antibodies and nucleic acids. Nucleic acids such as DNA or RNA are especially preferred. In one embodiment of the invention mixtures of specific nucleic acids are purified, in which the target nucleic acid(s) may be a minor component in terms of concentration (or may be present in low abundance). According to the present invention, a target nucleic acid shall be the nucleic acid of interest, i.e. a nucleic acid which shall be investigated as its presence is indicative of a certain condition or disease of a human or animal. For example, the presence of a viral sequence (e.g. from Hepatitis B Virus, Hepatitis C Virus or Human immunodeficiency virus) indicates that the respective individual is infected by the specific virus. Then, this viral sequence would be the target sequence. Other target sequences are sequences which are indicative of a predisposition of an individual to a certain disease as e.g. an inherited disease as sickle cell anemia or to certain types of cancer. This examples should be illustrative of the invention but should not ne delimiting. Samples according to the invention include clinical samples such as blood, serum, oral rinses, urine, cerebral fluid, sputum, stool, biopsy specimens and bone marrow samples. The sample can also be of a type used for environmental analysis, food analysis or molecular biology research, e.g., from bacterial cultures, phage lysates and products of amplification procedures such as the PCR.

The procedure described can be used to isolate native or modified biological material. Native biological material is understood to be material, the structure of which was not irreversibly changed compared with the naturally-occurring biological materials. This does not mean that other components of the sample can not be modified, however. Modified biological materials include materials that do not occur in nature, e.g., nucleic acids that are modified by attaching to them groups that are reactive, detectable or capable of immobilization. An example of this are biotinylated nucleic acids.

In certain cases the sample can be used without pretreatment in the isolation procedure according to the invention. In many cases, however, the sample should be lysed using an appropriate method, releasing the biological material contained in the sample. Procedures for lysing samples are known by the expert and can be chemical, enzymatic or physical in nature. A combination of these procedures is applicable as well. For instance, lysis can be performed using ultrasound, high pressure, by shear forces, using alkali, detergents or chaotropic saline solutions, or by means of proteinases or lipases. With regard for the lysis procedure to obtain nucleic acids, special reference is made to Sambrook et al.: Molecular Cloning, A Laboratory Manual, 2nd Addition, Cold Spring Harbour Laboratory Press, Cold Spring Harbour, N.Y. and Ausubel et al.: Current Protocols in Molecular Biology 1987, J. Wiley and Sons, NY.

In addition to the biological material to be isolated, the sample can also contain other components in a liquid such as cell residue, proteins, salts and other substances that are not to be isolated. This sample, which preferably contains the biological material in native form, is brought in contact with the particles under conditions in which the target biological material binds to the particle surface. The conditions for this depend on the type of biological material involved, but are basically known. They also depend on the method by which the biological material is bound to the surface. If immunological interactions are utilized for the binding, for instance, conditions must be selected that are suitable for the formation of immunocomplexes. If modified nucleic acids are used, the binding can take place via the groups of nucleic acids that represent the modification, e.g., biotin via binding with streptavidin-coated surfaces. With nucleic acids in particular, however, a direct binding of nucleic acids to glass is preferred because among other reasons the nucleic acids do not have to be modified and even native nucleic acids can be bound. The procedure for binding native nucleic acids to glass particles can be analogous to the procedure described in the prior art. It is preferably performed in the presence of chaotropic salts with a concentration of between 2 and 8 mol/l, and preferably between 4 and 6 mol/l. Chaotropic salts can be sodium iodide, sodium perchlorate, guanidinium thiocyanate, guanidinium isothiocyanate or guanidinium hydrochlorite. Other compounds are also possible.

To bring the sample in contact with the particles, the sample is mixed with the particles and incubated for a period of time sufficient for the binding to occur. Experts are usually familiar with the duration of the incubation step from procedures for performing treatment with non-magnetic particles. This step can be optimized by determining the quantity of immobilized biological material on the surface at different points in time. Incubation times of between 10 seconds and 30 minutes can be appropriate for nucleic acids.

Depending on the size and type of magnetic particles, the particles either separate out of the fluid during the incubation period itself or the suspension remains intact for a longer period of time. If the particles are very small and unmagnetized, the suspension remains intact for a longer period of time. If the particles are of larger size, the particles slowly separate out of the fluid during the incubation period.

Immobilization is preferably not performed via precipitation by lowering the solubility of the materials to be immobilized. Rather, immobilization is based on biospecific interactions (capture molecules) or adsorption. This largely prevents contaminants from being non-specifically included.

After incubation, the biological material is separated from the liquid. This is achieved in general by separating the material bound to the magnetic particles by applying a magnetic field. For instance, the magnetic particles can be pulled to the wall of the vessel in which incubation was performed. The liquid containing the sample contents that were not bound to the magnetic particles can then be removed. The removal procedure used depends on the type of vessel in which incubation was performed. Suitable steps include removing the liquid via pipetting or aspiration.

The magnetic particles can then be purified one or more times using a wash solution, if desired. A wash solution is used that does not cause the biological material to be released from the particle surface but that washes away the undesired contaminants as thoroughly as possible. This wash step preferably takes place by incubating the wash solution with the particles. The particles are preferable resuspended during this step, e.g., by means of shaking or applying a magnetic field that is not identical to the first magnetic field. The contaminated wash solution is preferably separated just like the sample in the step described above for binding the biological material.

After the last wash step, the magnetic particles can be dried briefly in a vacuum, or the fluid can be allowed to evaporate. A pretreatment step using acetone may also be performed. If desired, the biological material purified in this manner can be separated from the magnetic particles. This step also depends on the manner in which the biological material was bound to the magnetic particles. If the biological material is native nucleic acids and the magnetic particles are glass-coated particles, the nucleic acids can be removed from the particles according to the invention using an elution buffer having a low salt content. Buffers of this nature are known from DE 3724442 and Analytical Biochemistry 175, 196-201 (1988). The elution buffers with a low salt content are in particular buffers with a content of less than 0.2 mol/l. In an especially preferred embodiment, the elution buffer contains Tris. In another special embodiment, the elution buffer is demineralized water.

In yet another embodiment, the purification and isolation procedure described is performed after the cells (e.g., viral particles or prokaryotic or eukaryotic cells) are separated immunomagnetically from a bodily fluid or tissue. In this step, the sample is incubated, e.g., while shaking, with magnetic particles to which an antibody against an antigen on the cell is immobilized. These particles can be particles according to the invention or commercially available particles (e.g., MACS Microbeads from Miltenyi Biotec GmbH, Bergisch Gladbach, Germany). After a magnetic field is applied, one or more wash steps are performed using a saline solution. Particles are obtained to which the desired cells are bound. The bound cells are then resuspended in a saline buffer. In a preferred embodiment, this saline buffer is a chaotropic saline solution so that the nucleic acids contained in the cell are released from the cells.

An especially advantageous procedure for isolating nucleic acids from samples containing cells is achieved by combining the isolation of cells described above with the isolation of nucleic acids also described above, on the magnetic particles according to the invention. The advantage of this embodiment is its potential simplicity (single-tube method), high sensitivity (especially important in medical microbiology and oncology), and the ease with which it can be automated.

The biological materials isolated using the procedure according to the invention can now be used further as necessary. For instance, they can be used as a substrate for various enzymatic reactions. When nucleic acids are involved, they can be used for sequencing, radioactive or non-radioactive labelling, amplification of one or more of the sequences they contain, transcription, hybridization with labelled probe nucleic acids, translation or ligation. An advantage of the procedure according to the invention is that it is very easy to separate the biological material from the fluid. In the prior art, a centrifugation step was used to separate the glass particles from contaminants, or, when the biological material is bound to glass fiber filters, the fluid is drawn through the filters. This is a limiting step that makes it difficult to process large quantities of sample.

The biological materials can be separated from contaminants more effectively using the particles according to the invention. In particular, inhibitors for certain enzymatic reactions can be removed to a large extent according to the invention.

In the preferred embodiment, the particles according to the invention are added to the lysis mixture. After a suitable period of time for adsorption to take place—which can be optimized by mechanical agitation—the particles are separated from the surrounding fluid that contains additional cell components that are not to be detected. This is performed preferably by applying a magnetic field by placing a magnet against the vessel wall.

To remove any contaminants that may still be present, a wash step is preferably performed with a fluid that does not cause the nucleic acids to be determined to be released from the glass surface. An elution buffer having reagent conditions under which the nucleic acids separate from the glass surface is added to remove the nucleic acids from the glass surface. These conditions are low salt conditions in particular. Depending on the intended further use of the nucleic acids, the fluid can now be separated from the particles and processed further. This separation step is preferably performed via application of a magnetic field so that the particles are separated from the eluate.

A preferred embodiment of the present invention is to use the MGPs of the present invention in automatable methods as e.g. described in WO 99/16781. Automatable method means that the steps of the method are suitable to be carried out with an apparatus or machine capable of operating with little or no external control or influence by a human being. Automatized method means that the steps of the method are carried out with an apparatus or machine capable of operating with little or no external control or influence by a human being. Only the preparation steps for the method may have to be done by hand, e.g. the storage containers have to filled up and put into place, the choice of the samples has to be done by a human being and further steps known to the expert in the field, e.g. the operation of the controlling computer. The apparatus or machine may e.g. add automatically liquids, mix the samples or carry out incubation steps at specific temperatures. Typically, such a machine or apparatus is a robot controlled by a computer which carries out a program in which the single steps and commands are specified. Preferred automatic methods are those which are carried out in a high-throughput format which means that the methods and the used machine or apparatus are optimized for a high-throughput of samples in a short time. In another embodiment the MGPs according to the present invention are used in semi-automated process which means that some reaction steps may have to be done manually. In a preferred embodiment of the invention, a suspension containing MGPs according to the present invention is taken from a storage container and partial volumes are added to different reaction vessels. Reaction vessels may be reaction tubes made from plastics eventually in mictrotitreplate format contain 96 or 384 or more wells where a reaction can be carried out. However, these vessels may be made from other material e.g. from steel.

A preferred embodiment of the invention are purification methods followed by a detection step or purification methods followed by an amplification and detection step. The target nucleic or nucleic acid or nucleic acids of interest may be contained in a matrix of non-target nucleic acids, and may even be a minor component in said mixture of specific nucleic acids. Suitable DNA detection methods are known to the expert in the field and are described in standard textbooks as Sambrook et al.: Molecular Cloning, A Laboratory Manual, 2nd Addition, Cold Spring Harbour Laboratory Press, Cold Spring Harbour, N.Y. and Ausubel et al.: Current Protocols in Molecular Biology 1987, J. Wiley and Sons, NY. There may be also further purification steps before the DNA detection step is carried out as e.g. a precipitation step. The detection methods may include but are not limited to the binding or intercalating of specific dyes as ethidiumbromide which intercalates into the double-stranded DNA and changes its fluorescence thereafter. The purified DNA may also be separated by electrophoretic methods optionally after a restriction digest and visualized thereafter. There are also probe-based assays which make use of a oligonucleotide hybridisation to specific sequences and following detection of the hybrid. It is also possible to sequence the DNA after further steps known to the expert in the field. Newer methods apply a diversity of DNA sequences to a silicon chip to which specific probes are bound and yield a signal when a complementary sequences bind.

Preferred methods according to the invention are amplification methods as the ligase chain reaction and the polymerase chain reaction which specifically amplify target sequences to detectable amounts. Particularly preferred detection methods are the TaqMan® method disclosed in WO92/02638 and the corresponding U.S. Pat. Nos. 5,210,015, 5,804,375, 5,487,972. This method makes use of the exonuclease activity of a polymerase to generate a signal. In detail, the nucleic acid is detected by a process comprising contacting the sample with an oligonucleotide containing a sequence complementary to a region of the target nucleic acid and a labeled oligonucleotide containing a sequence complementary to a second region of the same target nucleic acid sequence strand, but not including the nucleic acid sequence defined by the first oligonucleotide, to create a mixture of duplexes during hybridization conditions, wherein the duplexes comprise the target nucleic acid annealed to the first oligonucleotide and to the labeled oligonucleotide such that the 3'-end of the first oligonucleotide is adjacent to the 5'-end of the labeled oligonucleotide. Then this mixture is treated with a template-dependent nucleic acid polymerase having a 5' to 3' nuclease activity under conditions sufficient to permit the 5' to 3' nuclease activity of the polymerase to cleave the annealed, labeled oligonucleotide and release labeled fragments; and the signal generated by the hydrolysis of the labeled oligonucleotide is detected and/or measured. TaqMan® technology eliminates the need for a solid phase bound reaction complex to be formed and made detectable.

In more general terms, a procedure for the purification of biological material followed by a detection step is disclosed wherein the amplification and/or detection reaction is a homogeneous solution-phase multiplex assay for the simultaneous detection of multiple targets (see examples 7.2).

In another embodiment of the invention, the described purification procedure is combined with a amplification procedure using one of the methods described in the following, preferably the use of blocking oligonucleotides. A problem often associated with amplification especially of low amounts of target nucleic acid is the activity of thermostable polymerases at lower temperatures (room temperature up to 40° C.). At this temperature primer oligonucleotides often bind unspecifically to each other or to background nucleic acid and may be extended by the polymerase. This entails a decrease of reaction components as well as to a higher level of background signal and consequently to a decreased sensitivity. It may also lead to false-positive results. In order to avoid unspecific activity of polymerases several approaches have been described, like "hot start"-PCR (Chou et al., 1992, Nucl. Acid Res 20, 1717-1723), covalently modified polymerases (e.g. AmpliTaq Gold, Perkin Elmer) or antibodies (Scalice et al., J. Immunol. Methods, 172, 147-163, 1994) and oligonucleotides (Dang and Jayasena, J M B 264, 268-278, 1996; U.S. Pat. No. 5,763,173; U.S. Pat. No. 5,693,502). According to the present invention blocking oligonucleotides shall be oligonucleotides which are able to block the active center of the polymerases up to the said temperature. These oligonucleotides may be e.g. an aptamer as described in Example 7.2.2.1.3.

In another embodiment of the invention aptamers (see e.g. in Example 7.2.2.1.3) and/or modified primers alone (see e.g. in Example 7.2.2.1.3) can be used in an amplification reaction and the detection methods connected thereto. This has advantageous effects and can be considered to be an invention on its own which provides superior results. In a preferred embodiment of the invention the 3'-terminal nucleobase, preferably an adenin is modified with a p-(t-butyl)-benzyl-residue.

Further modifications, including those at the 3'-1-position are described in EP 866 071 A2 which is incorporated herein by reference.

In still another embodiment of the invention for the purification of biological material followed by a detection step is disclosed wherein for at least 5 cycles of the polymerase chain reaction, the annealing temperature is less than 8° C., preferably less than 3° C. above the dissociation temperature of the polymerase-aptamer complex.

BRIEF DESCRIPTION OP THE FIGURES

Figure 3:
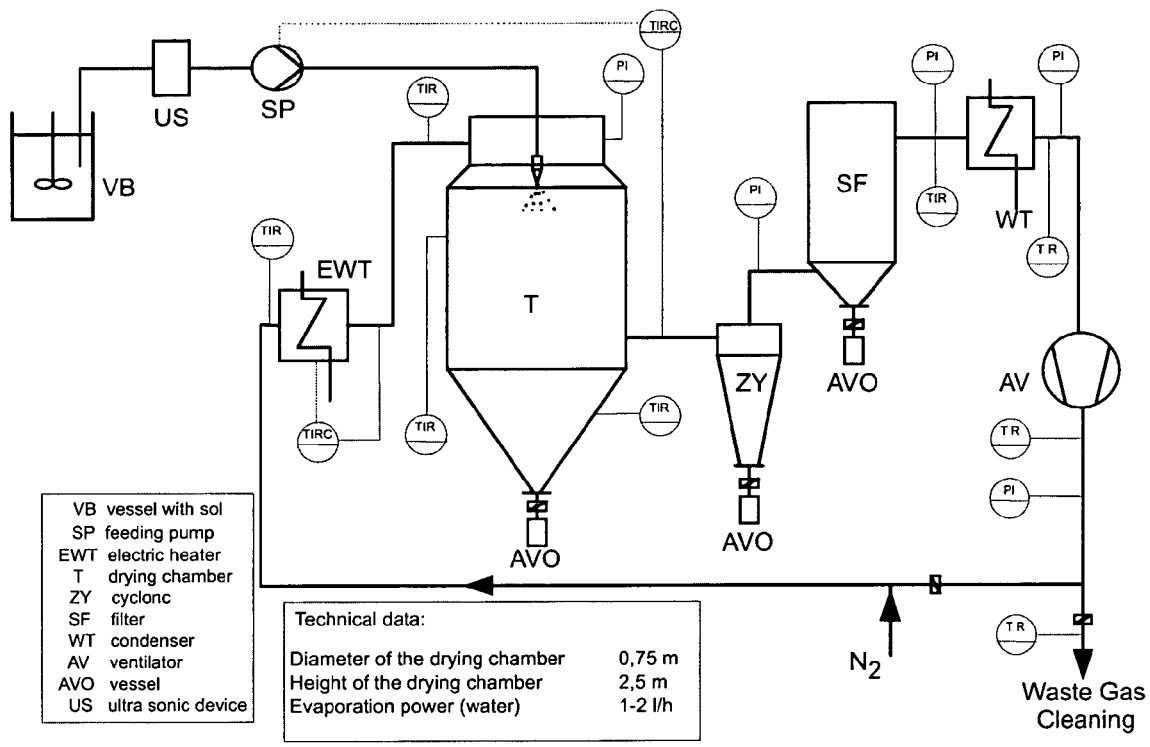
Figure 4:
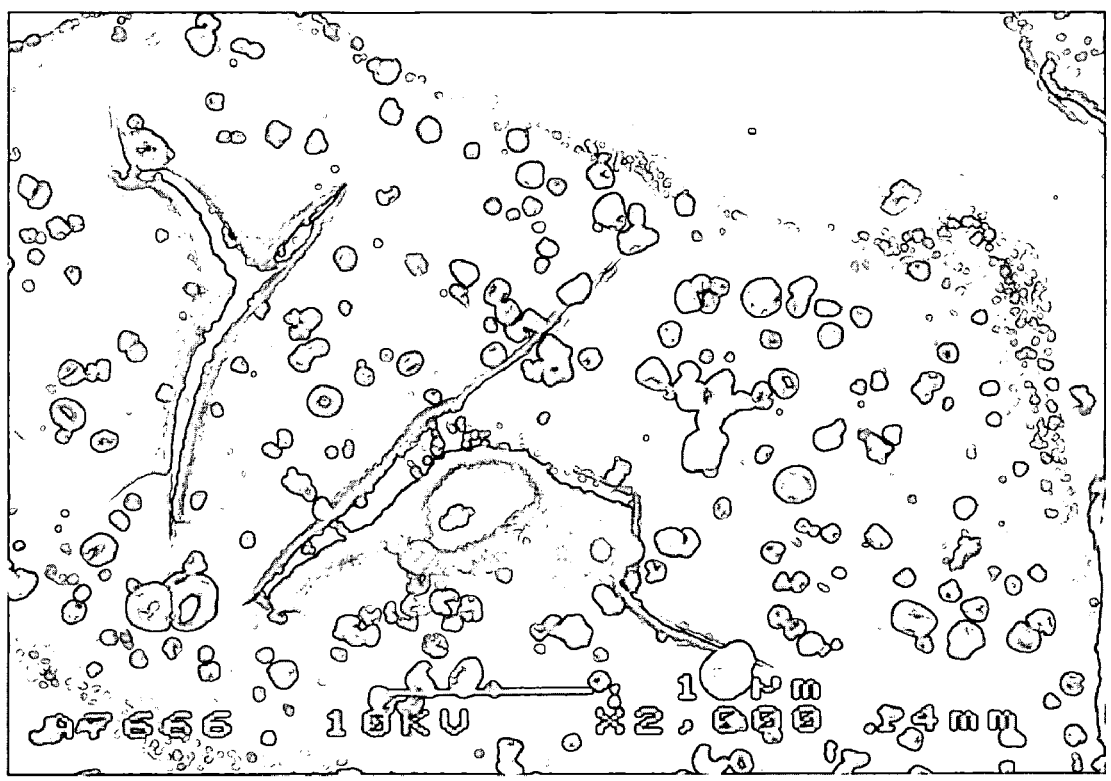
Figure 5:
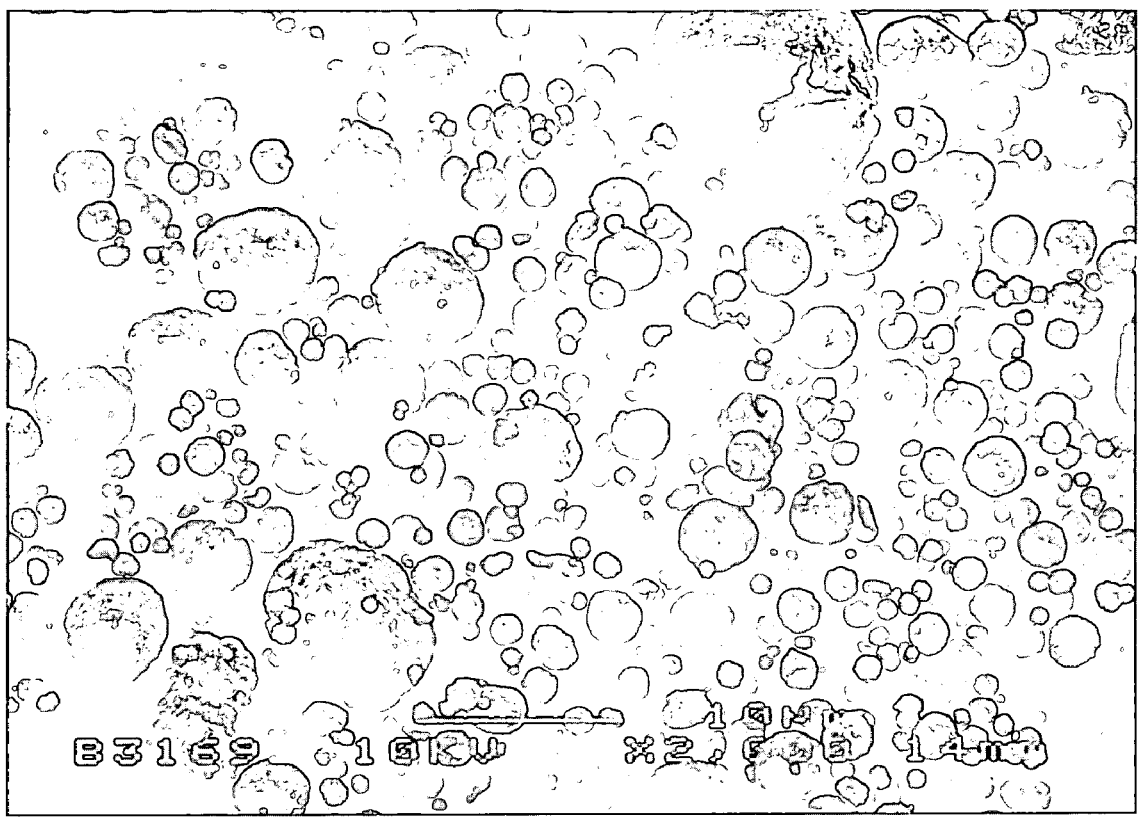
Figure 6:
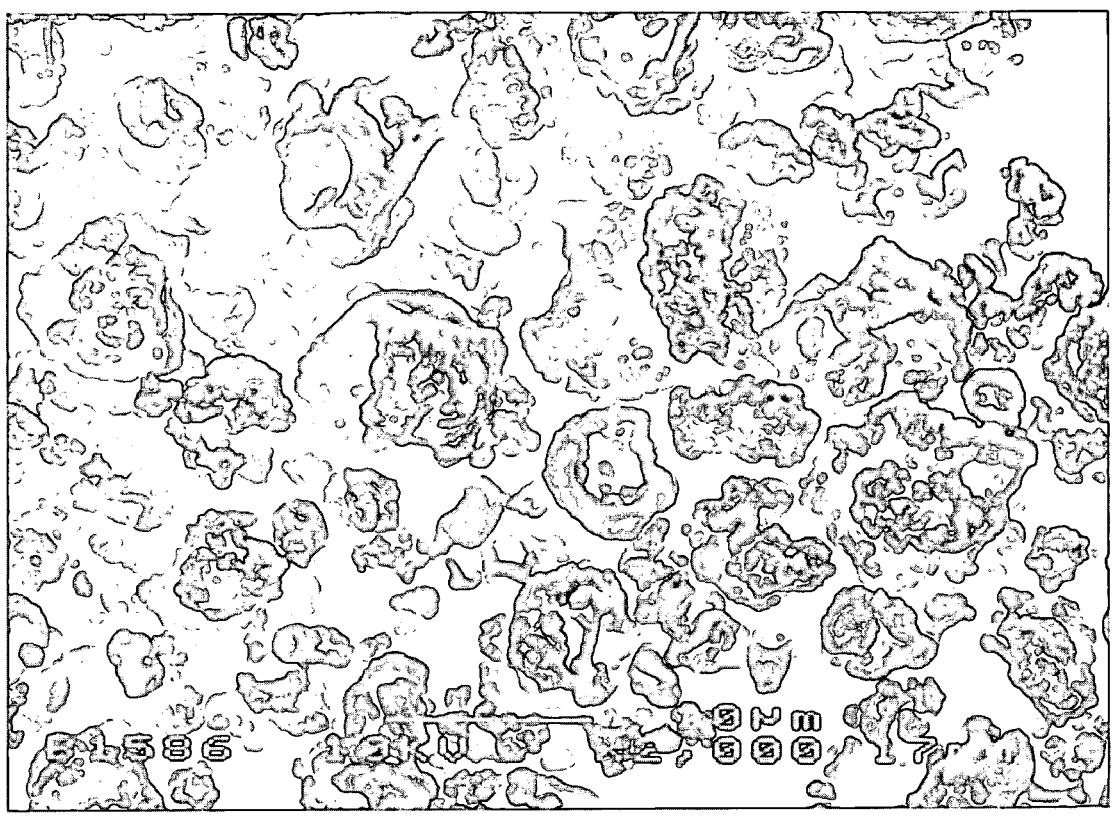
Figure 7:
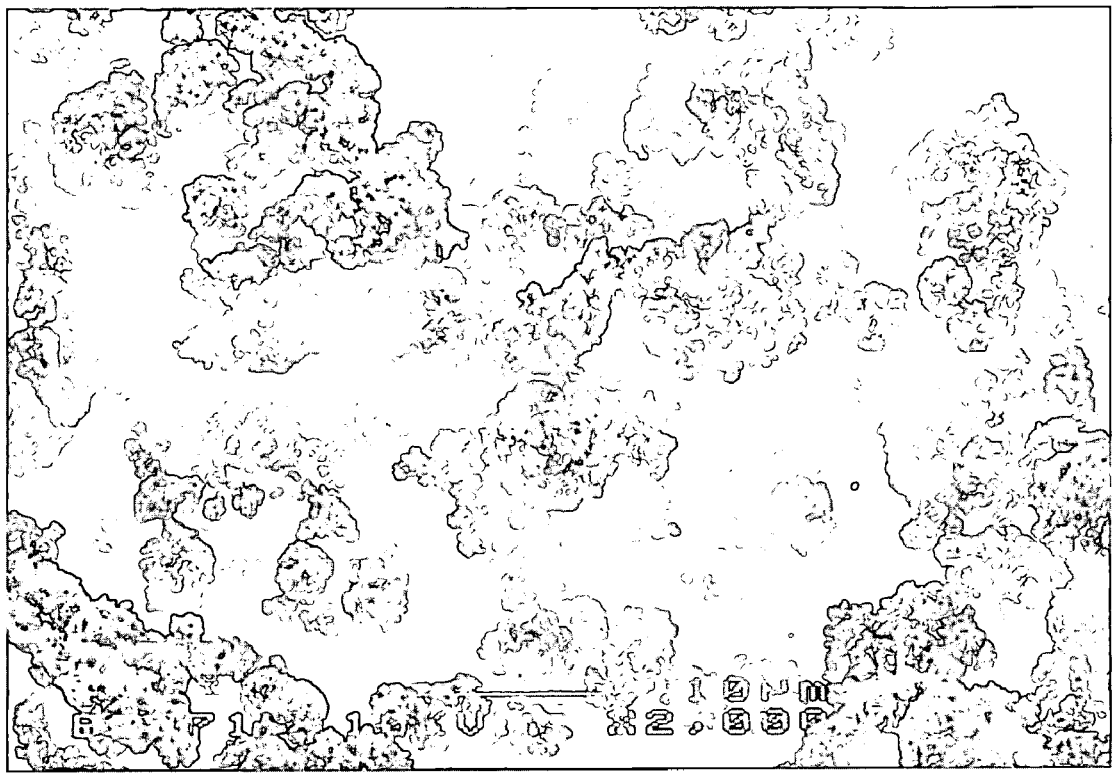
Figure 8:
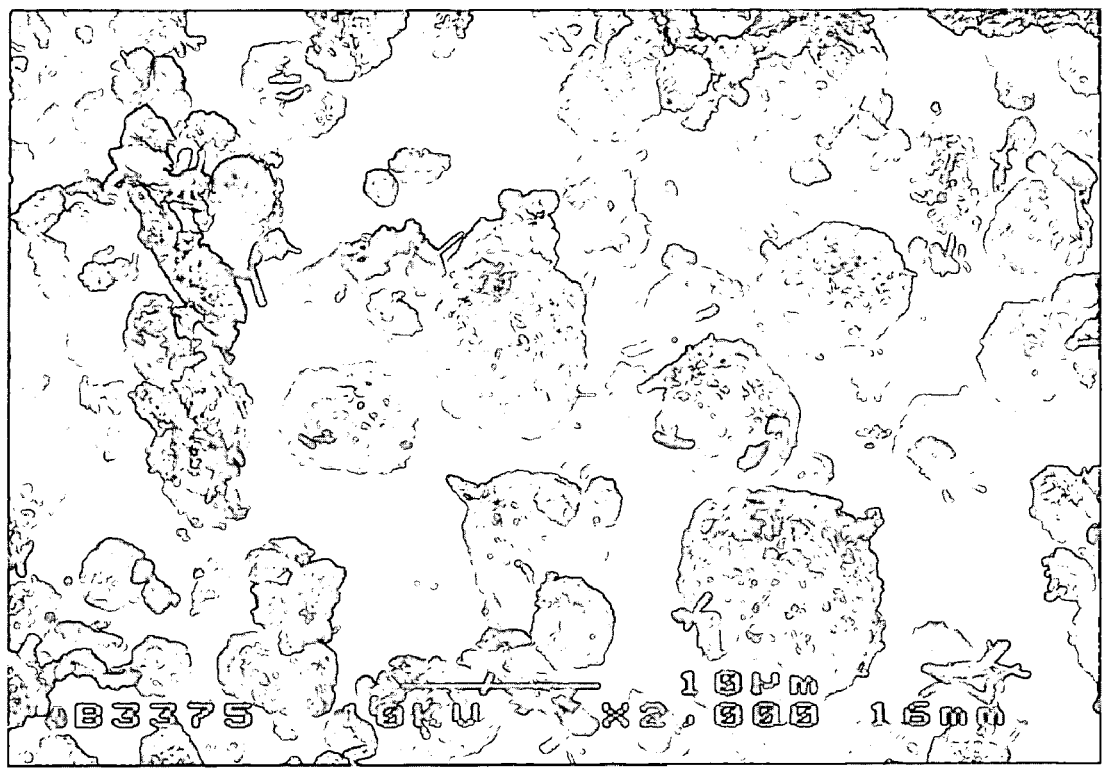
Figure 9:
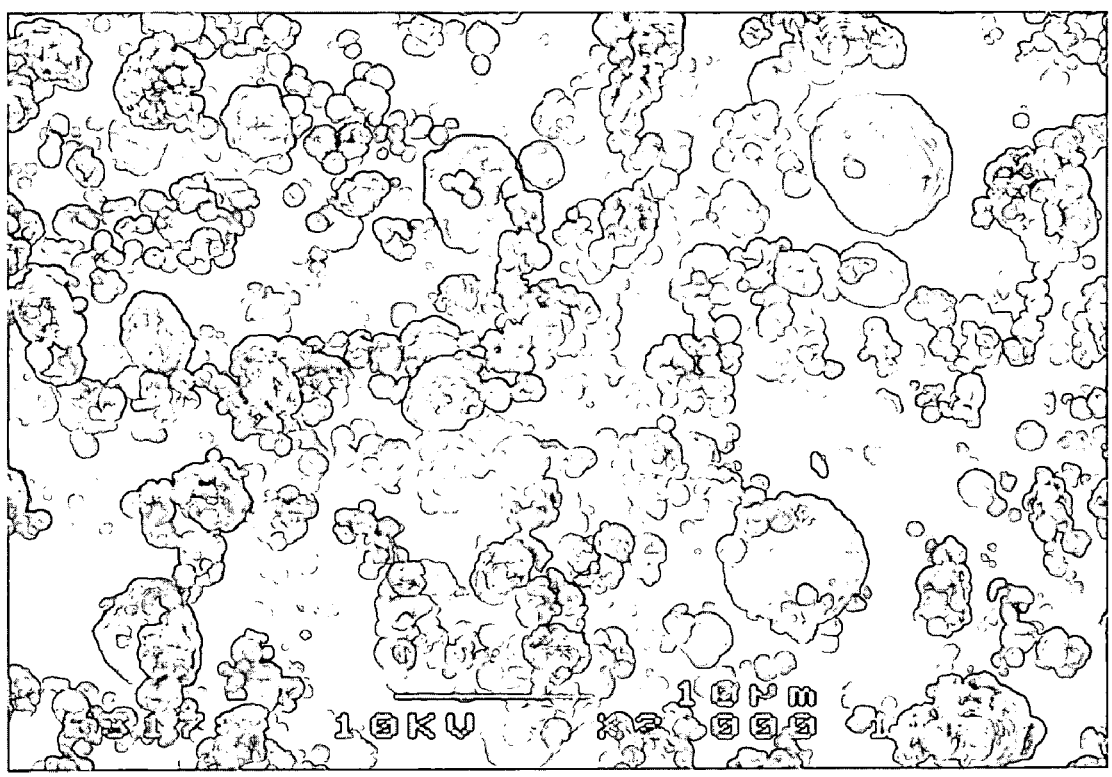
Figure 10:
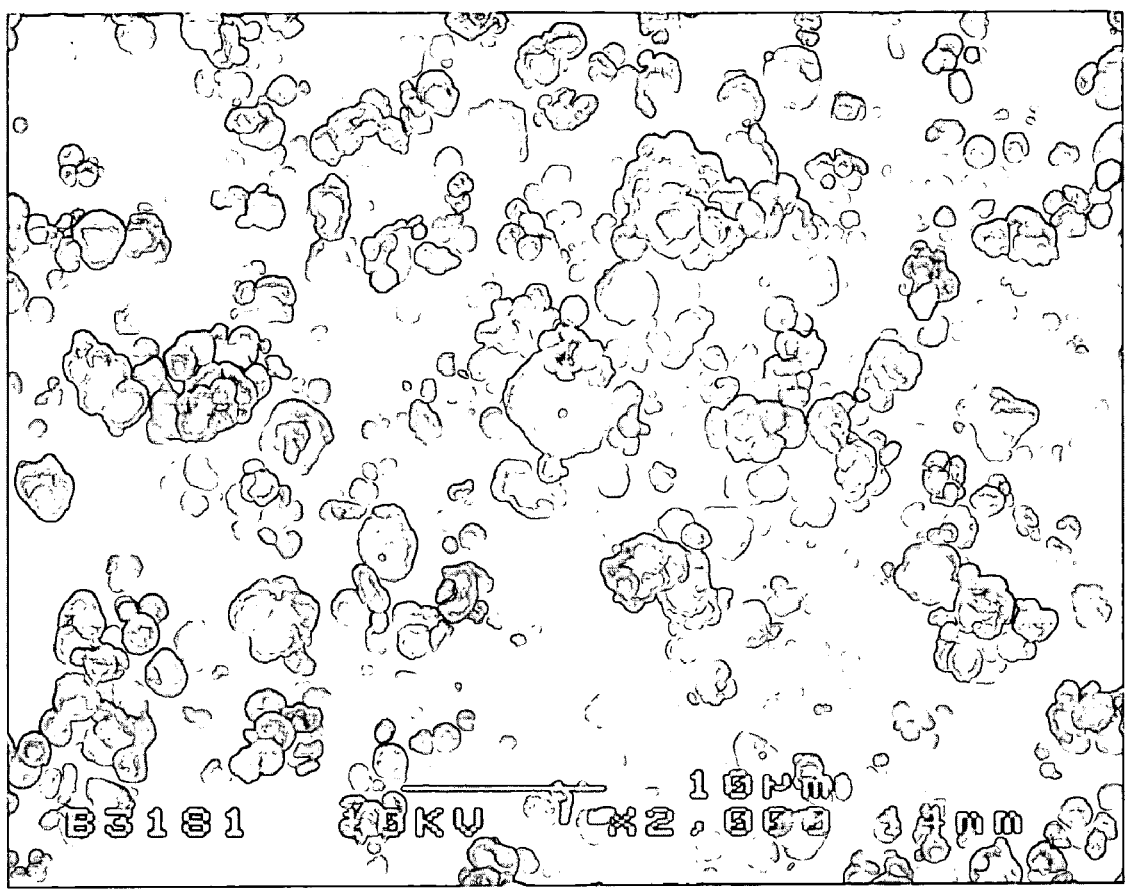
Figure 11:
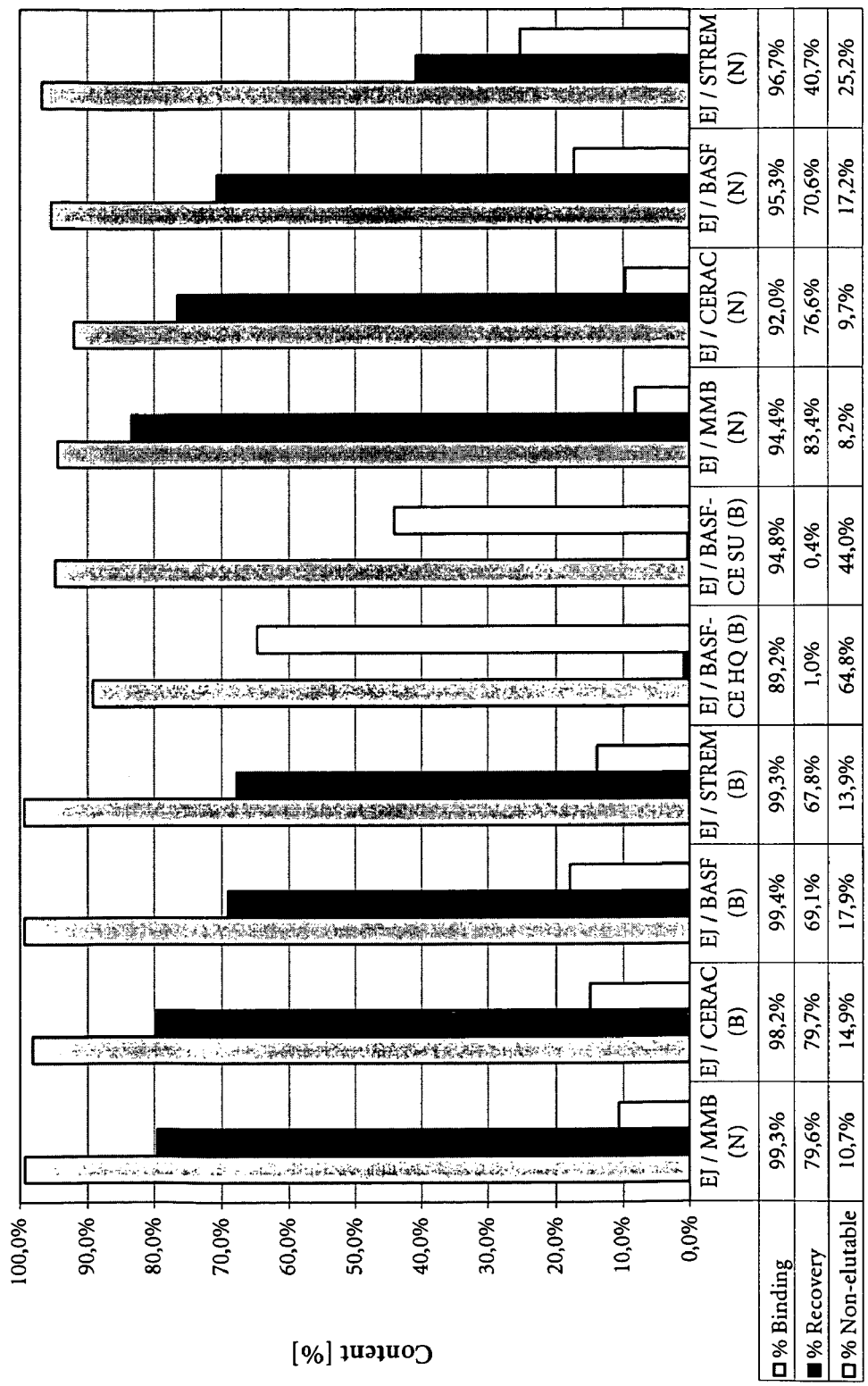
Figure 12:
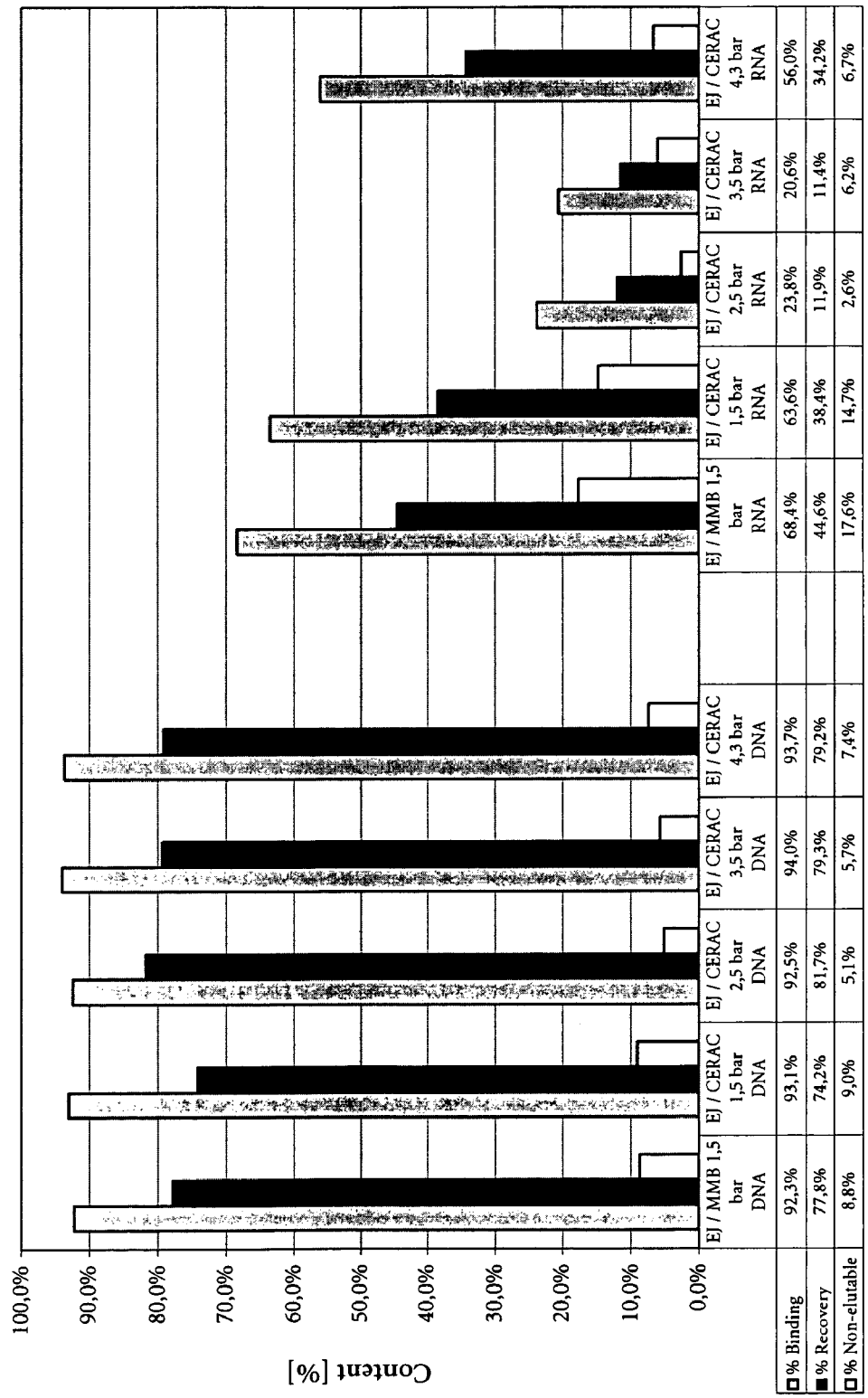
Figure 13:
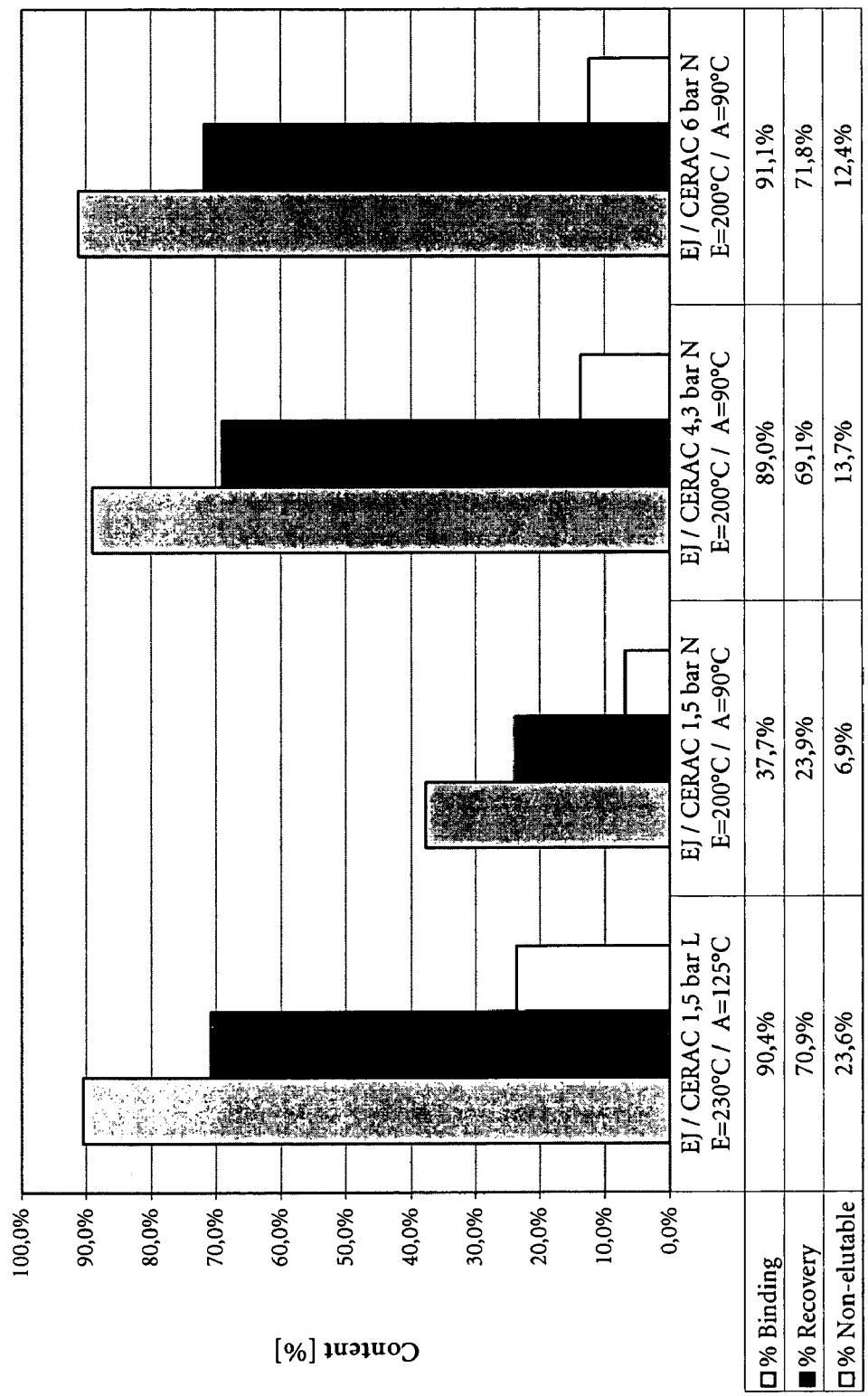
Figure 14:
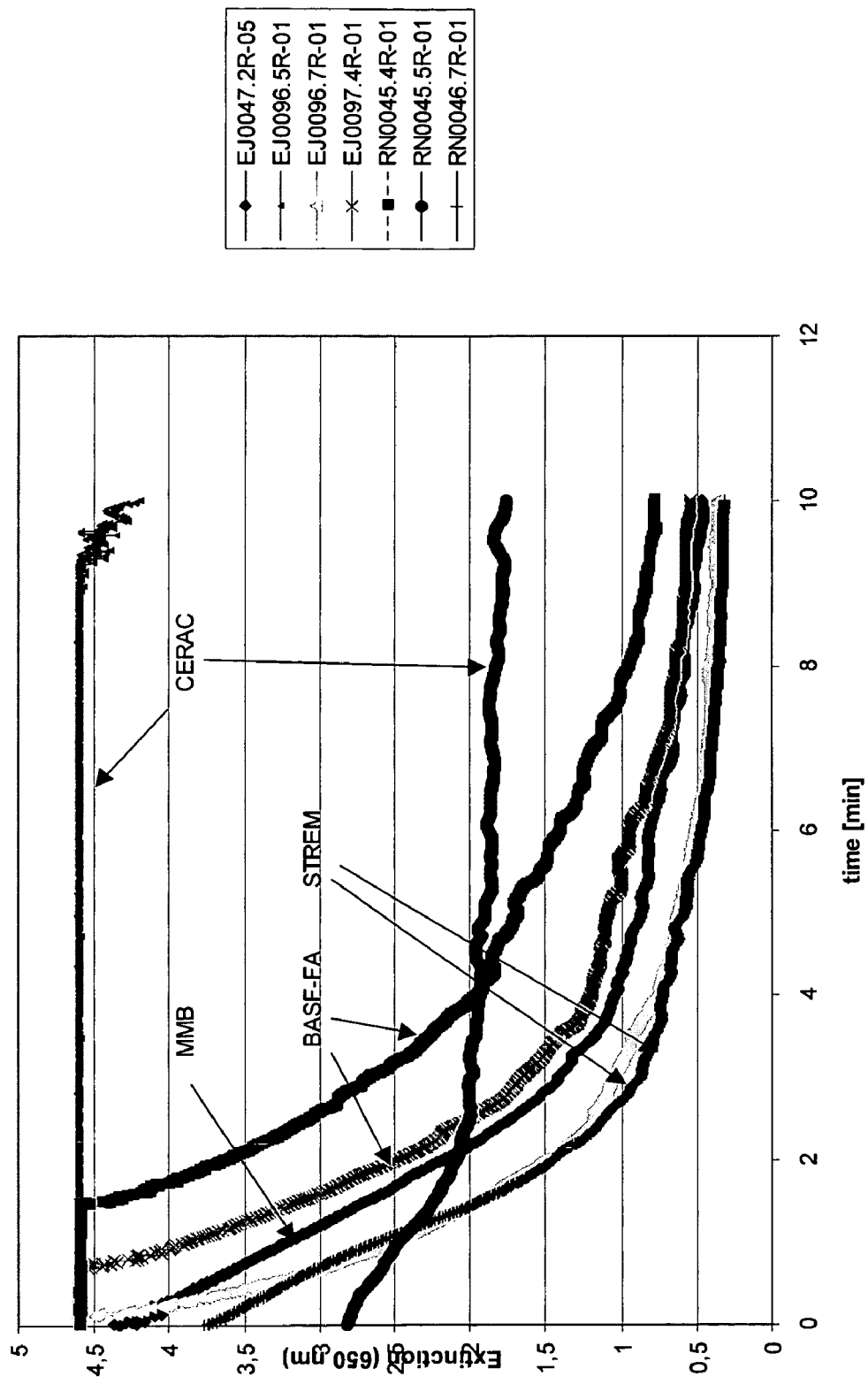
Figure 14:
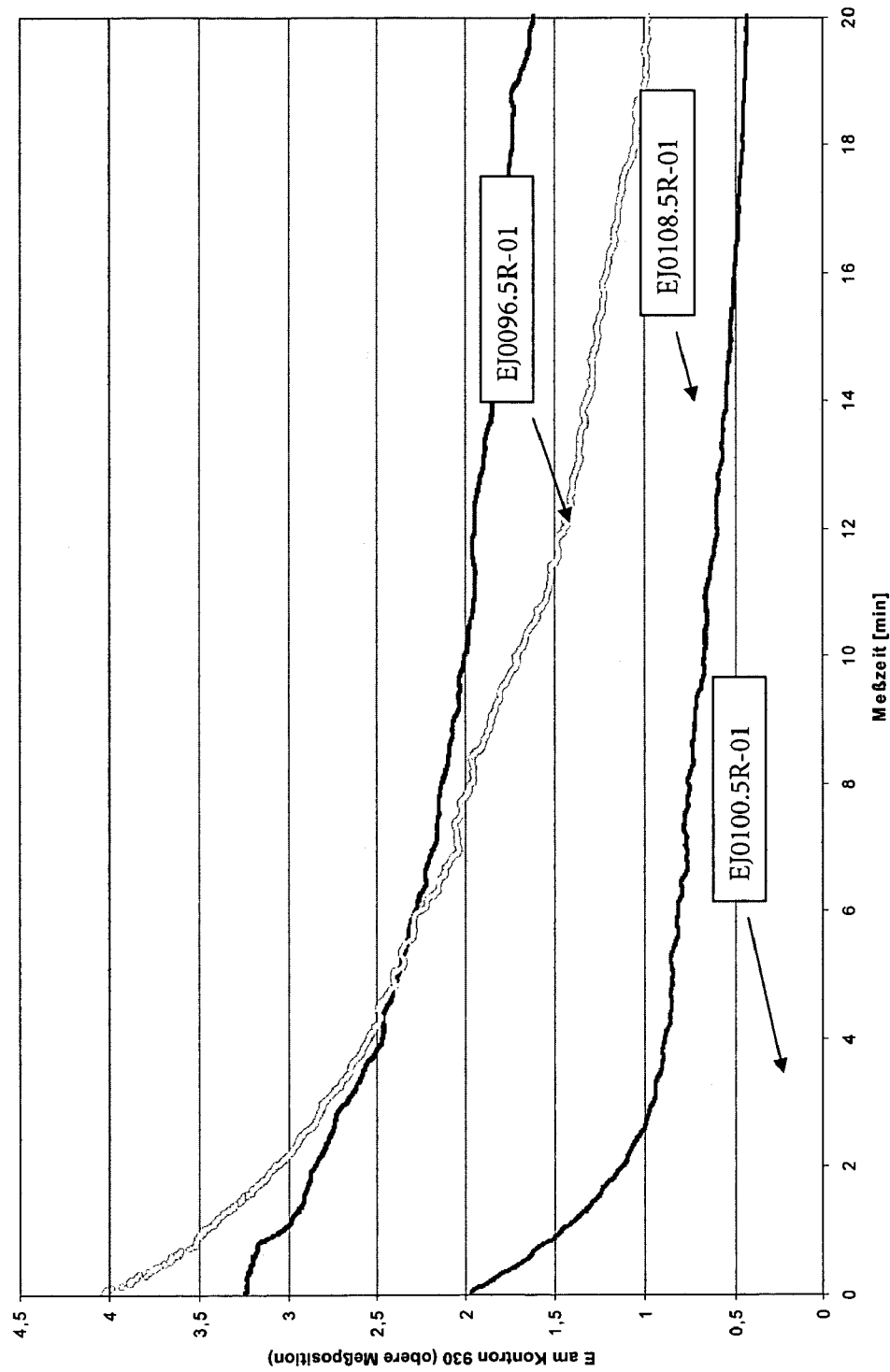
Figure 15:
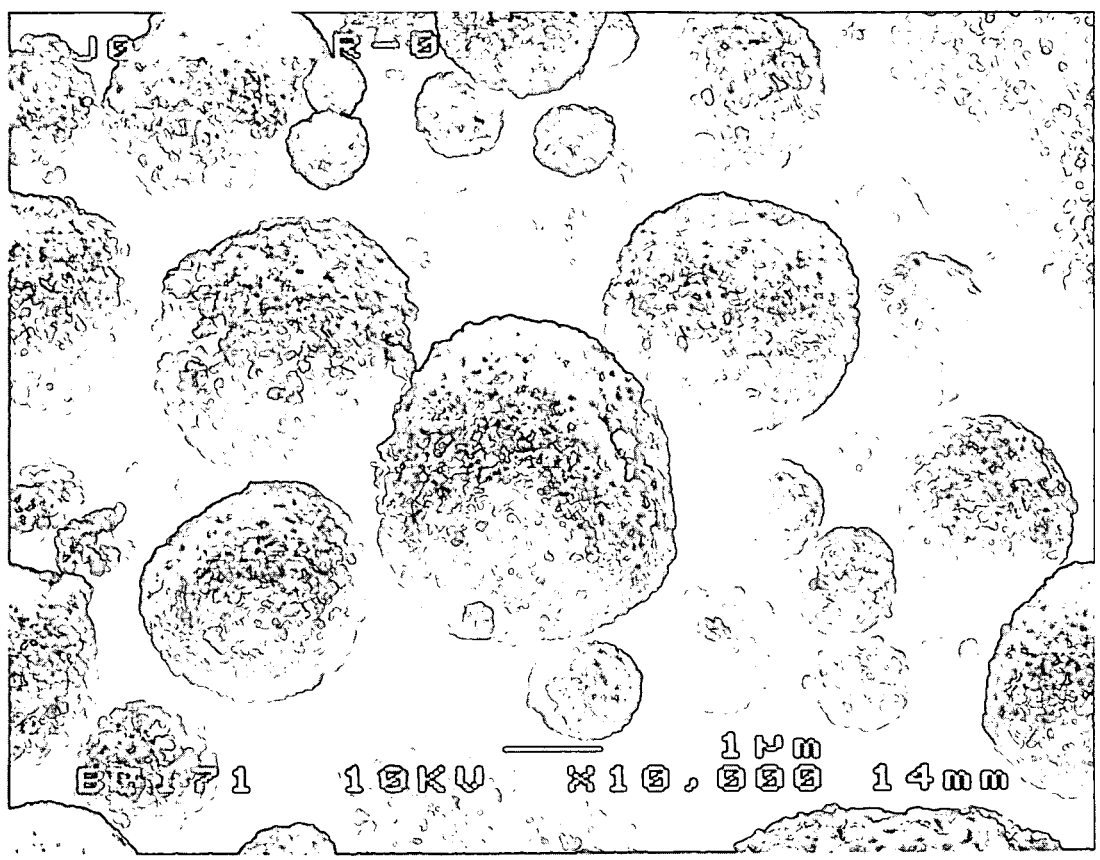
Figure 16:
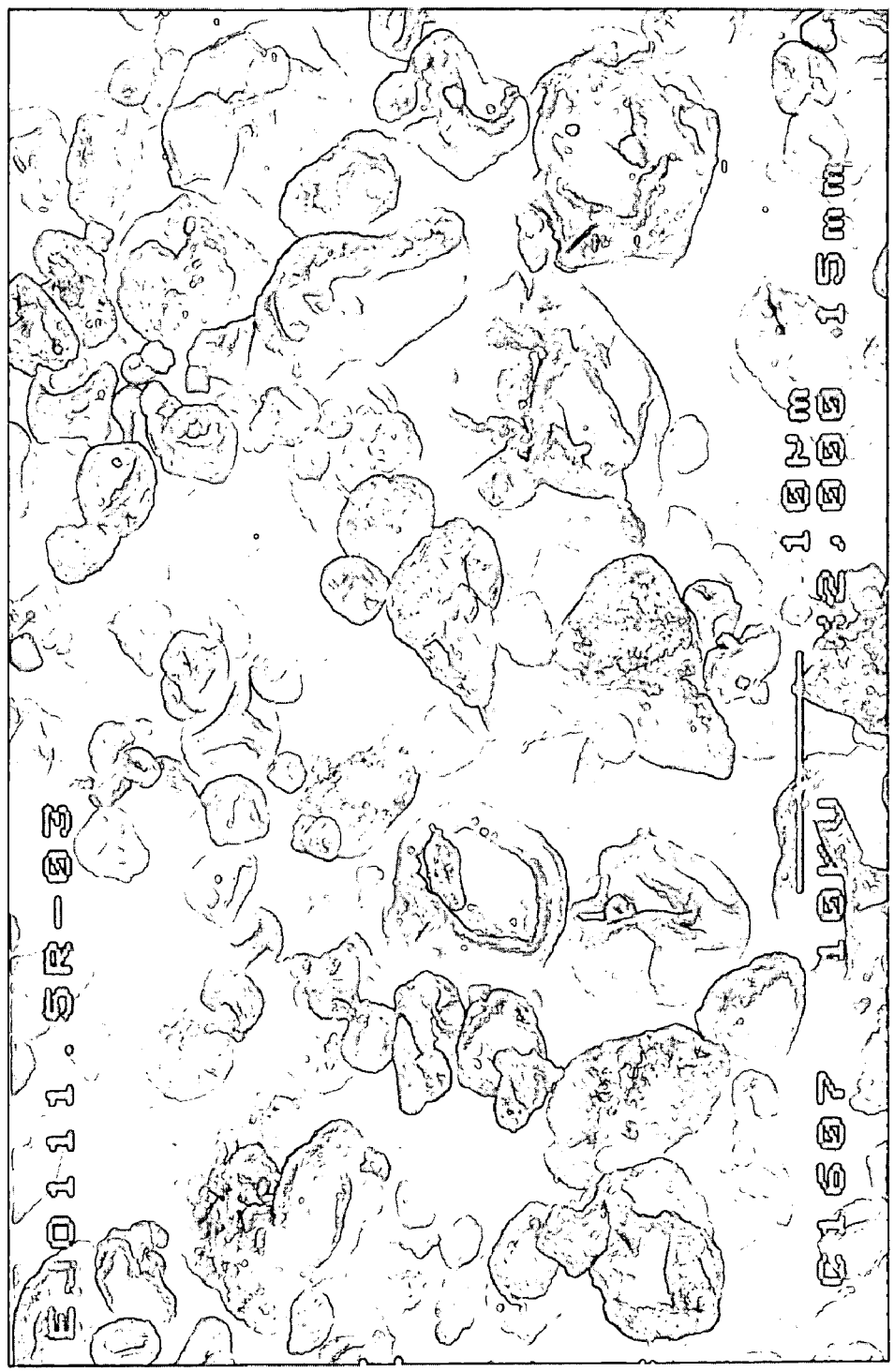

FIG. 1: Flow scheme for the production by sol synthesis & spray drying.
FIG. 2: Flow scheme for the preparation of the raw MGPs.
FIG. 3: Schematic depiction of the spray dryer manufactured by Nubilosa. The details are described in the text under Example 1.3.
FIG. 4: High resolution scanning electron microscopic image of MGP with Merck pigment BM.
FIG. 5: High resolution scanning electron microscopic image of MGP with CERAC pigment.
FIG. 6: High resolution scanning electron microscopic image of MGP with Merck pigment MMB.
FIG. 7: High resolution scanning electron microscopic image of MGP with Strem pigment.
FIG. 8: High resolution scanning electron microscopic image of MGP with BASF pigment FA.
FIG. 9: High resolution scanning electron microscopic image of MGP with BASF pigment CE-HQ.
FIG. 10: High resolution scanning electron microscopic image of MGP with BASF pigment CE-SU.
FIG. 11: Influence of the magnetic core pigment or the spray dryer on the RNA isolation (spray dryer: Büchi (B) or Nubilosa (N)).
FIG. 12: Influence of the parameter "Spray pressure" on the isolation of DNA or RNA.
FIG. 13: Influence of different MGP production parameters on the isolation of RNA (spray pressure, (L=air, N=nitrogen), inlet temperature (E) or outlet temperature (A).
FIG. 14A: Sedimentation behaviour of different MGPs in different suspension media.
FIG. 14B: Sedimentation behaviour of different MGPs in different suspension media.
FIG. 15: HREM-image of sample EJ0096.5R-01; MGP with CERAC pigment.
FIG. 16: HREM image of EJ0100.5R-01, sprayed at low pressure and high temperature, consisting mainly of deformed μ-scale particles.

EXAMPLES

The following examples serve to illustrate the embodiments of the invention.

1. Example 1

Production of the Magnetic Glass Particles

Classically, raw materials like $SiO_2$ and alkali- or alkaline earth carbonates ($Na_2CO_3$, $K_2CO_3$, $CaCO_3$) are molten together
Type of Reaction:

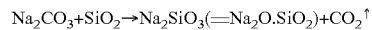

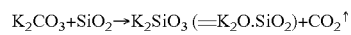

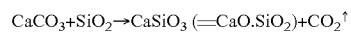

In most cases, however, a composite matrix of silicate, borate and aluminate is used, i.e. pertinent to the matrix constituents, $SiO_2$ is partially replaced by $B_2O_3$ and $Al_2O_3$.

Alternatively, glass can be synthesized via sol-gel-reaction.
Type of Reaction:
either acid-catalyzed sol-gel reaction, e.g.

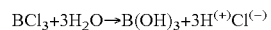

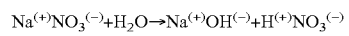

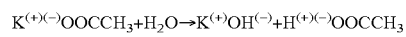

or base-catalyzed, as in our case, e.g.

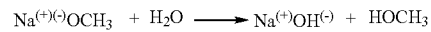

-continued

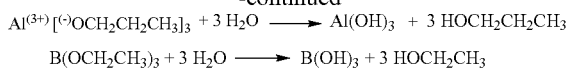

Advantage: alcohols are easily evaporated during spray-drying; ideally no recristallisation of salts on the surface.

Thus, alcoholates are turned into hydroxides, which yield by way of elimination of water the corresponding oxides. These, then, form a 3-dimensional, amorphous glass matrix consisting of $SiO_2/B_2O_3/Al_2O_3$, into which certain metal oxide ingredients are embedded as matrix bond separators, e.g.

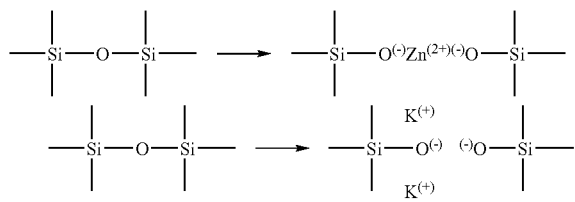

For the experiments described here, the glass component was produced via base-catalyzed sol-gel synthesis. The glass composition used in all experiments was (unless stated otherwise) as follows:

70.67 Mol % $SiO_2$, 14.33 Mol % $B_2O_3$, 5.00 Mol % $Al_2O_3$, 4.00 Mol % $K_2O$, 2.00 Mol % CaO, 4.00 Mol % ZnO (calculated from the mass of particular educts brought to reaction)

Description of the Investigated Magnetic Pigments

Different types of magnetic pigments were investigated and are summarized in Table 1.

Production of the Coating Sol (EJ-Composition)

The educts are added in the following order and amount into the heatable stirring vessel:

| | |
|---|---|
| Tetraethoxysilane (TEOS) | 10700 ml |
| Triethylborate (TEB) | 3305 ml |
| K-methanolate 25% (W/V) in Methanol | 1601 ml |
| Ethanol | 11292 ml |
| Aluminiumisopropanolate | 1385 g |
| Calcium | 54.4 g |
| Zincacetate | 498 g |

The vessel is closed thereafter. The sol is heated to 70° C. and stirred overnight (15 h). The temperature is regulated via a thermosensor which dips into the liquid.

Then the sol is heated to 90° C. and the alcohol/water mixture (Ethanol: 3781 ml, $H_2O$: 1512 ml) is added at a rate of 5000 ml/h. The vessel is cooled to 20° C. after the complete addition of the said mixture.

The lid is opened and 10249 g magnetic pigment (CERAC) is added under vigorous stirring. The prepared sol is transferred into the spray dryer via a hose.

Spray Drying

The inlet temperature of the spray dryer is regulated to 200° C. The nozzle pressure is regulated to 6 bar and the nozzle is cooled for 3 min with ethanol. Then the hose is connected to the outlet of the glass container and the pigment-containing sol is pumped at a rate of 110 ml/min to the two fluid nozzle (diameter of the opening: 2 mm; supplier: Nubilosa, Type 1B1VVS1) of the spray dryer via a ultrasound device (200 W). The spray drying system is shown schematically in FIG. 3. The particles which are formed in the first two minutes are discarded. After the complete spraying of the sol the container under the cyclone (AVO, see FIG. 3) with the particles will be taken and the particles will be further treated as described in the next steps.

The pigment containing sol is stirred in the stirring vessel to prevent sedimentation of the suspended particles. The sol is transferred from the vessel to the nozzle using a pump (SP). Nitrogen heated by an electric heater (EWT) is used as drying gas. The coated pigment is transferred from the drying chamber (T) to the cyclone (ZY). The dried powder an be removed from the container (AVO) under the cyclone. Very fine particles are removed by a filter (SF) from the nitrogen. The spray dryer is used with overpressure to prevent an air intake into the dryer. The gas flow is produced by gas blower (AV).

Further Processing of the Spray-dried Powder

The powder is transferred into a ceramics bowl and heated in an furnace to 200° C. at a heating rate of 1 K/min. Then temperature is held at 200° C. for one hour and the oven is cooled to room temperature afterwards. The bowl is transferred to an atmosphere furnace with a volume of 27 l which is rinsed with 60 l nitrogen per hour. The furnace is heated to 750° C. with a heating rate of 1 K/min and is held at that temperature for 1 hour. Then the furnace is cooled to 150° C. and rinsed with 60 l air per hour. The furnace is heated to 200° C. with a heating rate of 2 K/min and is held at that temperature for 1 hour and is cooled to temperature afterwards. The powder is transferred to a sieve (50 µm) and sieved for 30 min. Afterwards, the sieved sample is bottled in glass containers, which are sterilized unclosed in an oven which is heated to 200° C. with a heating rate of 1 K/min, held at that temperature for 4 h and then cooled to 80° C. Then the glass vessels are taken from the furnace, covered with sterile foil and closed with a lid.

A summary of the important process parameters is presented in Table 2 and Table 3, the produced individual samples with some data are provided in Table 3. Each sample has a specific code. The first two letters describe the used glass chemistry (see below) and the next four numbers encode the production process (see Table 2). The number after the describes the used pigment (see Table 1). The letter R means that the fine content has not been removed, whereas E means that the fine content has been removed with ethanol. The last two numbers describe the number of the lot. The composition of the glass (code EJ) as calculated from the quantity of the educts was 70.67 Mol % $SiO_2$, 14.33 Mol % $B_2O_3$, 5.00 Mol % $Al_2O_3$, 4.00 Mol % $K_2O$, 2.00 Mol % CaO, 4.00 Mol % ZnO. The composition of the glass (code RN) was 74 Mol % $SiO_2$, 15 Mol % $B_2O_3$, 5.00 Mol % $Al_2O_3$, 4.00 Mol % $K_2O$, 2.00 Mol % CaO. The composition of the glass (code EP) was 73.61 Mol % $SiO_2$, 14.93 Mol % $B_2O_3$, 5.21 Mol % $Al_2O_3$, 4.17 Mol % $K_2O$, 2.08 Mol % CaO.

2. Example 2

High Resolution Scanning Electron Microscopy

To obtain information about the surface, size and form of the MGP, we carried out investigations with a high resolution scanning electron microscope manufactured by the company JEOL (JSM). The samples were spread onto the sample holder with an electrically conducting double-sided adhesive and sputtered with gold for 36 s with a current of 30 mA. For the imagining of the surface, the emitted secondary electrons (topography) as well as the back-scattered electrons (order number contrast) were viewed. The used primary electron voltage was 10 kV (secondary electrons) or 25 kV (back-scattered electrons).

The FIG. 4 shows MGPs with mica covered with ferric oxide as magnet pigment (BM). The fissure in the glass shell can be clearly seen which stem from the spray drying of the particles when the layer starts to shrink on a non-shrinking substrate (drying fissures). Further more a greater number of spheric particles can be seen which do not contain one of the bigger magnet particles (10-60 µm). These spheres without magnetic core (non-magnetic fine content) cannot be removed in a magnetic field, may be transferred into the PCR reaction and will interfere with this reaction. The particles with CERAC pigment (see FIG. 5) do not have fissure, as the magnet pigment (23 nm average particle size) does not cause tension forces in the layer so that no fissures are created during the spray drying process. Furthermore, the small CERAC-particles are also incorporated in the fine content so that there are no non-magnetic particles contained therein. The particles are also substantially smaller than the particles with mica which can be observed in these figures with the same magnification. MGPs with the other magnetic pigments are shown at the same magnification in FIG. 6 to FIG. 10.

3. Example 3

Physical Investigations of the MGPs

To allow an evaluation of the MGPs before the actual functional tests, in addition the HREM investigations further physical measurements were done with the MGPs. It was interesting to learn about the iron solubility in water, the magnetic force, the fine content and the density. In the following the experiments are described and the results presented.

3.1 Extinction Measurements

To test whether the fines have been removed, 1000 mg of the temperature-treated and sieved powder, are weighed into a 50 ml centrifugation tube (Sarstedt), 40 ml water added and dispersed by shaking. Then, the tube is dipped into a ultrasonic bath (Sonorex (RK 102H; 120/240W) with the total filling height and is put into a magnetic separator (Roche Diagnostics GmbH RD Art.Nr. 1858 025). After 3.5 min magnetic separation, liquid is taken from the vessel with a pasteur glass pipette in the height of the 15 ml mark at the opposite side of the magnet and filled into a 5 mm quartz cuvette (Type 110-QS, Hellma). The extinction of the supernatant is measured in an UV-VIS-NIR spectrometer (Hitachi U-3000) against a corresponding cuvette filled with deionized water. The measuring range was 200 to 1100 nm in steps of 1 nm to investigate this wavelength range for the absorption bands of eventual impurities. The extinction at a wavelength of 280 nm and 400 nm was taken as a reference.

3.2 Density Measurements

For the density measurements a gas pyknometer (AccuPyc 1330, Fa. Micromeritics) is used. Helium 6.0 is used as gas. The device is calibrated with the supplied standard (steel beads with known volume). Further, the sample is dried for at least 1 hour at 150° C. and then filled into the measurement container and weighed. After the measuring container is put into the gas pyknometer, 10 washing cycles and 5 measuring cycles are used to determine the average value and the standard deviation.

3.3 Determination of the Iron Solubility

The iron solubility of the coated and temperature-treated samples is determined with Inductive Coupled Plasma—Atomic Emission Spectroscopy (JY 24, company ISA). Therefor, 1 g of the sample is transferred into a 50 ml polypropylene-tube, filled up with distilled water and kept at a temperature of 60° C. for 20 hours. Then, the samples are filtrated with a 0.2 µm syringe filter and the filtrate is measured. Four single determinations are carried out at a wavelength of 259, 940 nm and an average value is computed therefrom.

3.4 Measurement of the Magnetic Force

For the measurement of the magnetic force a PP-weighing tube (Company Licefa, Art. Nr. V2-3) completely filled with MGPs is weighed. With the help of a stencil, this sample container is placed in the middle of LDPE tube (Company Kartell, TS 735) burdened with brass so that the lid of the tube can be still closed. The vessel is positioned in the middle of a balance (detection accuracy 0.1 g) with the help of another stencil. After the equalization of the balance, a plastics cap which contains an cylinder-shaped magnet (diameter: 30 mm; height: 113.5 mm; material: samarium-cobalt 2/17) is positioned above the scale.

Thereby, the MGPs in the scale are attracted against to the gravity thereby decreasing their weight. After the adjustment of the equilibrium (1.5 min) the weight loss of the sample is determined and the value is normalized for 250 mg MGP.

3.5 Results

The results of the physical characterization of the MGPs with EJ composition and different pigments are summarized in Table 3. It is noticeable that the extinction values are very low when CERAC pigment is used. This can be explained by the lack of non-magnetic fine content because the small CERAC pigment (23 nm) can be incorporated into each magnetic glass particle. The density of the CERAC-MGPs is not very high. This has a positive influence on the sedimentation velocity. The magnetic force is subjected to high fluctuations, however, it is positively influenced by the use of CERAC-pigments. The CERAC-MGPs have a comparatively high leak of iron to the water. However, even ten-fold higher values did not show any effect on the PCR process.

In summary, it can be said that the physical properties do not have any significant differences between the different pigments but the CERAC-MGPs have a very low fine content.

4. Example 4

Influence of the Magnetic Core Pigment and of the Spray Dryer on the BET Surface The surfaces were determined using a device from Micromeritics (Type ASAP 2400). The measurement was performed at liquid nitrogen temperature. Nitrogen 5.0 was used as measuring gas and Helium 4.6 was used as inert gas. Typically, 5 g of sample was used for one measurement.

The surface of the MGPs plays an obvious role for the isolation of DNA and RNA. The higher the surface the more DNA can be bound by the same mass of MGPs. It is also possible to use less MGPs and obtain the same performance. This has the effect that the intergrain volume is less which means that less alcohol may be introduced as contaminant into the PCR reaction. The data for the measured BET-surfaces for some samples are summarized in Table 4. When the surfaces of the samples produced on the big spray dryer are compared, it should be noted that the samples with small pigments (BASF FA, STREM and CERAC) have relatively high surfaces, whereas the big Merck pigments have small surfaces. This may be caused by the fact that big magnetic particles cause big MGPs whereas the small magnetic particles are incorporated into the spherical droplets during the spray drying process and have therefore similar surfaces under similar spraying conditions. The BASF CE-SU particles have a size distribution in between the small (BASF FA, STREM and CERAC) and the big Merck particles. In contrast to the Merck particles, they do not possess a structured surface so that these particles have a very smooth glass surface. This results into a smaller surface. A higher pressure was used with the smaller spray dryer and the nozzle of this spray dryer is remarkably smaller than that of the bigger spray dryer. This causes smaller particles whereby the surface increases remarkably. This is in good agreement with the results of Example 5.2.1.

Any influence of the magnetic pigment or the spraying pressure on the results of further physical investigations cannot be recognized except the above-mentioned influence on the fissure formation and the fine content. However, only the measurements of the surface show a direct connection to the results of the functional investigations. Other physical investigation results do not show this direct correlation.

5. Example 5

Binding Studies Via Radio Tracing

There are several methods for the evaluation of MGPs with regard to their suitability for the extraction of nucleic acids. The determination of the extinction at 260 nm before and after the purification is not very sensitive and does not resemble the situation when small amounts of target nucleic acid are extracted from clinical material. The results of functional evaluation methods which rely upon a method for the amplification of nucleic acids, as e.g. by PCR, RT-PCR, NASBA or anything similar, are often not enough convincing. Furthermore, these methods, which are suitable for the determination of a small number of copies of the target genome, are susceptible to disturbances by substances from the sample material or from the sample preparation process. Radioactive binding studies are a suitable analytical method which makes it possible to analyze the sample preparation process step by step. The performance data are no absolute data but are always relative to the performance of a reference particle 5.1 Experimental Protocol At first, radioactively labelled DNA or RNA is synthesized enzymatically in a PCR or in vitro transcription process in the presence of $^{32}$P-markied desoxynucleoside or nucleoside-triphosphates. Then, the marked DNA or RNA is separated from the free nucleoside-triphosphates, the content determined and a defined dilution is prepared. A small amount of marked DNA or RNA is added to each sample before the examination. During sample preparation, all nucleic acids bind to the MGPs in the presence of chaotropic agents. The MGPs are pelleted by the exertion of magnetic forces and the supernatants can be discarded. The pellet is washed and the bound nucleic acids are eluted at elevated temperature by the reversal of the reaction conditions, i.e. by the addition of a low salt elution buffer. After the binding and an optionally after the washing step, an aliquot of the particle supernatant is spotted onto a filter. The eluate as well as the in water redispersed MGP are spotted onto a filter as well and dried thereafter. At last, the filters are measured in a Beta.Counter and for each sample preparation a distribution is calculated.

5.1.1 Preparation of Radioactively Labelled DNA
5.1.1.1 A.1.1. Reagents
Expand High Fidelity PCR System (Roche Molecular Biochemicals Cat. No. 732641)
dNTP Mix (Roche Molecular Biochemicals Cat. No. 1277049)
Deoxycytidine 5'-alpha-P32 Triphosphate dCTP 3000 Ci/mmol (Amersham Cat. No. PB 10205)
lambda-DNA (Roche Cat. No. 1029053) concentration 1 ng/ml
Radiotracer primer 1 (SEQ ID NO 1) concentration 5.3 $OD_{260}$/ml
Radiotracer primer 2 (SEQ ID NO 2) concentration 5.2 $OD_{260}$/ml
QIA Quick PCR Purification Kit (Qiagen Cat. No. 28104)
5.1.1.2 Reaction
29.5 µl double distilled water
5 µl Expand High Fidelity Buffer
2.5 µl dNTP Mix (1:10) diluted with double distilled water
1 µl Radiotracer primer 1 (SEQ ID NO 1)
1 µl Radiotracer primer 2 (SEQ ID NO 2)
0.31 µl $^{32}$P-dCTP
10 µl lambda-DNA
0.75 µl Expand High Fidelity —Enzyme Mix
5.1.1.3 Amplification
2 min. 94° C.
10 cycles (10 sec. 94° C./30 sec. 60° C./60 sec. 72° C.)
20 cycles (10 sec. 94° C./30 sec. 60° C./60 sec. 72° C.+10 sec. 72° C. extension per cycle)
7 min 72° C.
4° C.
5.1.1.4 Purification
according to the QIA Quick PCR Purification Protocol (Qiagen)
5.1.1.5 Dilution
Dilution of DNA 1:10 in double distilled water and measurement in the Beta-Counter
5.1.2 A.2. Preparation of Radioactively Labelled RNA
5.1.2.1 Reagents
SP6/T7 Transcription Kit (Roche Molecular Biochemicals Cat. No. 999644)
Uridine 5'-alpha-P32 Triphosphate UTP 3000 Ci/mmol (Amersham Cat. No. PB 10203)
Plasmid pBKBH10S, linearized with EcoRI at 100 µg/ml
High Pure RNA Isolation Kit (Roche Molecular Biochemicals Cat. No. 1828665)
5.1.2.2 Reaction
2 µl 10× buffer
3 µl NTP Mix (AGC)
1 µl UTP (1:50 with double distilled water)
5 µl $^{32}$P-UTP
7 µl linearized plasmid
1 µl RNAse Inhibitor (Roche Molecular Biochemicals Cat. No. 802808)
1 µl T7 RNA-Polymerase
5.1.2.3 Transcription and DNAse-Digest
20 min incubation at 37° C.
Addition of 2 µl DNAse, RNAse free
10 min incubation at 37° C.
Addition of 178 µl double distilled water
5.1.2.4 Purification
according to the High Pure RNA Isolation Protocol (Roche Molecular Biochemicals)
5.1.2.5 Dilution:
Dilution of RNA 1:30 in double distilled water and measurement at the Beta-Counter

5.1.3 Radioactive Sample Preparation
5.1.3.1 Reagents
negative plasma

Proteinase K concentration 20 mg/ml (e.g. Roche Id.Nr. 1942387)

Poly-A-RNA (e.g. Roche Id.Nr. 108626) concentration 1 mg/ml; diluted 1:1000 (volume/volume ratio) with lysis buffer lysis buffer (50 mM Tris pH 7.0, 15% (v/v) Polydocanol, 5M Guanidiniumisothiocyanate, 1 mM DTT)

MGP (with glass composition EJ and different core pigments (BM, MMB, CERAC, STREM, BASF-FA, BASF-CE)) suspended in isopropanol at 60 mg/ml or at 6 mg/ml Washing buffer (20 mM Tris pH 7.5, 20 mM NaCl, 70% (v/v) Ethanol)

Elution solution: double distilled water

Auxiliary material: Whatman GF/D Filter

5.1.3.2 Reaction (1.5 ml Protocol)
80 µl Proteinase K add 410 µl negative plasma and mix add 500 µl lysis buffer and mix add 10 µl radioactive labelled DNA or RNA and mix 10 min incubation at room temperature under shaking add 500 µl MGP suspension (concentration 6 mg/ml) and mix 20 min. incubation at room temperature under shaking separation for 2 min in Magnetic separator (Dynal)

discard supernatant and spot 300 µl onto a filter add 750 µl wash buffer, vortex, 2 min separation discard supernatant, eventually spot 375 µl supernatant onto a filter repeat washing procedure twice add 100 µl elution solution, incubate 5 min. at 80° C. in a thermomixer separate 2 min in a magnet holder, spot supernatant onto a filter add 100 µl elution solution, resuspend and spot MGPs onto a filter dry filters for 60 min at 75° C. in a drying oven transfer filter into scintillation tubes, add 5 ml scintillation solution and measure in the beta-counter

5.1.3.3 Experimental Protocol (1 ml Protocol)
25 µl Proteinase K add 415 µl negative plasma and mix add 500 µl lysis buffer and mix add 10 µl radioactive labelled DNA or RNA and mix 5 min incubation at room temperature under shaking add 50 µl MGP suspension (concentration 60 mg/ml) and mix 20 min. incubation at room temperature under shaking separation for 2 min in the magnetic separator (Dynal)

discard supernatant and spot 300 µl onto a filter add 700 µl wash buffer, vortex, 2 min separation discard supernatant, eventually spot 350 µl supernatant onto a filter repeat washing procedure twice add 120 µl elution solution, incubate 10 min. at 80° C. in a thermomixer separate 2 min in a magnet holder, spot supernatant onto a filter add 100 µl elution solution, resuspend and spot MGPs onto a filter dry filters for 60 min at 75° C. in a drying oven transfer filter into scintillation tubes, add 5 ml scintillation solution and measure in the beta-counter

5.2 Results of the Radiotracing Experiments:
5.2.1 Influence of the Magnetic Core Pigment or the Spray Dryer on the RNA Isolation Different MGP-types, which were produced using EJ glass chemistry and various cores in the nano- or mikrorange (MMB, CERAC, etc.) on different spray dryers (Büchi or Nubilosa), were characterized with regard to their behaviour at the nucleic acid extraction from virus-negative pool material with the radiotracing method according to Example 5.1.3.2. The RNA parameter proved to be the most sensitive in the course of the studies and was therefore chosen as parameter. FIG. 11 shows BASF-CE is not suitable as core material because only small amounts of the bound RNA can be found in the eluate. The EJ/CERAC particles which were sprayed in the Büchi system at 6 bar showed the performance of the reference EJ/MMB which were sprayed in the Nubilosa system.

5.2.2 Influence of the Parameter Spray Pressure on the Isolation of DNA or RNA Different MGP types produced with the Nubilosa system with different spraying pressures are compared according to 0. The reference particles are EJ/MMB MGP. The DNA and RNA binding properties are investigated. Whereas the DNA parameter shows no dependence from the spraying pressure, the RNA parameter shows significant performance differences. The performance of the EJ/CERAC particles produced with 1.5 bar spraying pressure with the Nubilosa system is lower than that of the reference. There is a lower performance in the series in dependence of the spraying pressure which varied from 1.5 to 3.4 bar (~30%). Particles which are sprayed with 4.3 bar reached 90% of the performance of the particles which are sprayed at 1.5 bar (see FIG. 12).

The experiments prove the direct connection between the process parameters for the production of the MGPs and of the performance in the test. It should be noted that an increase in the spraying pressure leads to a lower test performance but, beginning from a certain spraying pressure, the particle properties are improved leading to a better performance.

5.2.3 Influence of Different MGP Production Parameters on the Isolation of RNA and DNA These experiments should lead to the result whether a variation of the spraying pressure leads to MPGs with even better performance.

Therefor, MGPs are produced on the Nubilosa system at a pressure of 1.5 bar, 4.3 bar and 6 bar using nitrogen as spraying gas.

In order to obtain a careful drying process, inlet and outlet temperature of the spray dryer are additionally decreased. The influence of these factors on the RNA isolation is investigated according to 5.1.3.3 using EJ/MMB MGP as reference.

The results (see FIG. 13) show the surprising effect of a dramatic performance reduction which is caused by the decrease of the spraying temperature and could not be foreseen. It was possible to reach the performance of the reference quality by the increase of the spraying pressure. Concomitant with the superior suspension stability, these particles are therefore superior to the reference.

6. Example 6

Sedimentation Analytics of the Magnetic Glass Particles

6.1 Experimental Protocol

An Uvikon Spectrophotometer Model 930 produced by Kontron Instruments is used for the evaluation of the sedimentation behaviour of the magnetic glass particles. This spectrophotometer is modified to allow variable adjustment of the cuvette along a scale bar. For the measurements the cuvette is set at a position in which the measuring beam with a wavelength of 650 nm traverses the cuvette at a position which is at ⅔ of the filling height (scale position 7.5). Macro cuvettes made from polystyrene are used which have a volume of 4 ml and a path length of 1 cm. Prior to measurements, calibration is made in a one beam procedure against pure suspension medium. The MGP samples are dispersed to homogeneity in suspension medium, typically at a mass/volume ratio of 3 mg/ml, and measured immediately. The change of the extinction with time is monitored continuously at the said wavelength of 650 nm. The physical quantity used for the comparison of the sedimentaton velocity of different samples is the half life ($t_{1/2}$) in a particular suspension medium. This is the peroid of time until the extinction of the suspension in the upper third of the cuvette is half the value at the beginning of the measurement. The decline of extinction is caused by the sedimentation of the particles and the concomitant clearance of the upper third of test volume.

The above-described device further allows the installation of a magnet beneath the cuvette. Thereby the velocity of the magnetic separation can be determined.

6.2 Results of the Sedimentation Analytics 6.2.1 Experiment 1:

Several MGP-types with different cores in the range of nano- or micrometers and produced with EJ glass chemistry are investigated spectrophotometrically for their sedimentation and separation behaviour, i.e. with and without magnet under the cuvette. Mass/volume is 6 mg/ml in this case. The suspension medium is a 1:1 mixture of isopropanol and lysis buffer. The results are summarized in SEQARABIC. The particles from the CERAC type show a clear advantage in the stability of the suspension but no disadvantages for the magnetic separation. (See also FIG. 14).

6.2.2 Experiment 2:

The sedimentation behaviour of different MGPs from the type CERAC produced with EJ glass chemistry are investigated in pure isopropanol.

Important production parameters EJ0100.5R-01-1.5 bar spraying pressure, 230° C. inlet temperature, Nubilosa system EJ0108.5R-01-4.3 bar spraying pressure, 230° C. inlet temperature, Nubilosa system EJ0096.5R-01-6.0 bar spraying pressure, 150° C. inlet temperature, Büchi system EJ0096.5R-01 is shown in FIG. 16. These beads are largely spherical, with a highly structured surface and a size of predominantly 0.5-5 µm. The sample EJ0100.5R-01, sprayed at low pressure and high temperature, consists mainly of deformed µ-scale particles (see FIG. 16, which shows a functional equivalent to EJ0100.5R). In conclusion, particles like EJ0096.5R-01 show significant retardation of sedimentation, which is most advantageous for liquid transfers of MGP suspensions (see FIG. 14b).

7. Example 7

Functional Test with PCR 7.1 Heterogeneous Functional Assays: Amplification with PCR on a Perkin Elmer GeneAmp 9600® and Detection with a Biospecific Binding Test with a Chemiluminiscent-Marked Detection Probe on a Modified Elecsys1010®

7.1.1 General Considerations

Virus particles in the sample (e.g. plasma) are lysed in the presence of protease and high concentrations of chaotropic salt as well as detergent. Then, the particulate adsorbent (=MGP) is added for physico-chemical adsorption of released nucleic acids onto the glass surface, followed by magnetic separation and washing of the loaded beads, i.e. bound/free separation. Finally, dissociation of bound nucleic acids from the beads (=elution) is conducted under reversed reaction conditions relative to adsorption, i.e. with low salt buffer or even distilled water. An aliquot of eluate is then mixed with an aliquot of PCR mastermix to start amplification of the nucleic acids recovered in the eluate. This reaction is characterized by the equation $N_i = N_0 \times (1+E)^n$, with
$N_0$=number of molecules at the start of the polymerase chain reaction
$N_i$=number of molecules at the end of polymerase chain reaction
E=efficiency of amplification=$0 \leq E \leq 1$
n=number of reaction cycles=typically $20 \leq n \leq 35$ After PCR with at least one biotinylated primer, an aliquot of biotin-tagged amplificate is mixed with hybridization buffer and detection probe. After incubation, streptavidin-coated beads are added, followed by another incubation. Finally the beads are washed, signal buffer is added and the chemiluminescent signal intensity measured, which is correlated with the mass of amplified nucleic acid bound and, thus, the viral load of the plasma sample.

The expert in the field may also carry out the 1 ml protocol manually.

7.1.2 Experimental Protocol 7.1.2.1 Reagents 7.1.2.1.1 Sample Preparation

Proteinase K, liquid in glycerol/Ca-acetate, 20 mg/ml
Poly-A-RNA, 1 mg/ml, use level is a 1:1000 dilution in lysis buffer lysis buffer, consisting of:
  Tris-buffer, 50 mmol/l, pH 7.0 (1.0 & extractor protocol, respectively) or 4.0 (1.5 ml protocol)
  Polydocanol, 15% (v/v) (1.0 & extractor protocol, respectively) or Triton X-100 20% (v/v) (1.5 ml protocol)
  Guanidinium-isothiocyanate, 5 mol/l
  1 mmol/l DTT
  magnetic glass particles (MGP) either of the type EJ/BM, EJ/MMB oder EJ/CERAC suspended in isopropanol (99.8% purity) at 60 mg/ml
wash buffer consisting of
  Tris-Puffer, 20 mmol/l, pH 7.5
  60% Ethanol/aq (1.0 & extractor protocol, respectively) or 70% (1.5 ml protocol)
  NaCl, 20 mmol/l
Eluent=double distilled water
  Amplification/Mastermix:
  PCR-buffer, consisting of
    buffer medium
  RT-PCR (Human immunodeficiency virus (HIV), Hepatitis C Virus (HCV)): 250 mmol/l Bicine/KOH pH 8.2, 557 mmol/l K-Acetat, 40% Glycerol
  HBV-PCR (Hepatitis B virus (HBV)): 20 mmol/l Tris-HCl pH 8.3; 100 mmol/l KCl, 0.012% Brij 35 (=2×-concentrate)
  Metal cations, $MgCl_2$ (HBV-PCR) 3 mmol/l or $MnCl_2$, (RT-PCR) 2.5 mmol/l (HCV) and 1.25 mmol/l (HIV)
  Deoxynucleoside-triphosphate (dATP, dGTP, dCTP, dTTP, dUTP)
  Analyte-specific forward-primer
  Analyte-specific reverse-primer
  Uracil-N-glycosidase (UNG)
  DNA-polymerase (Taq- or Tth-polymerase for HBV or HIV/HCV, respectively).
  $H_2O$-demineralised (molecular biology grade) for volume adjustment ad 100 µl
  Stop-reagent for UNG after the amplification
  N-lauroylsarcosine (e.g. Roche Id.Nr. 133895), 1% w/v); 5 µl per 100 µl amplificate

7.1.2.1.2 Detection

Hybridisation buffer (e.g. Roche Id.Nr. 1930273)
chemiluminescence-marked detection probes:
HCV (Roche BMO 28.140336), working stock 8.0 nmol/l
HIV (Roche BMO 28.540948), working stock=7.8 nmol/l
HBV (Roche BMO 28.540917), working stock=9.2 nmol/l
SA-covered ECL-Beads (e.g. Roche Id.Nr. 1865943-001)
denaturation solution (e.g. Roche Id.Nr. 1930257)
ProCell (e.g. Roche Id.Nr. 1717685)
CleanCell (e.g. Roche Id.Nr. 1717642)

7.1.2.1.3 Primers and Probes

| Primer: | |
|---|---|
| HIV-forward: | SEQ ID NO 3 |
| HIV-reverse: | SEQ ID NO 4 |
| HCV-forward: | SEQ ID NO 5 |
| HCV-reverse: | SEQ ID NO 6 |
| HBV-forward: | SEQ ID NO 7 |
| HBV-reverse: | SEQ ID NO 8 |
| Detection probes: | |
| HIV: | SEQ ID NO 9 |
| HCV: | SEQ ID NO 10 |
| HBV: | SEQ ID NO 11 |

7.1.2.2 Reaction Conditions & Test Procedure

Sample Preparation:
1.0 ml Manual Protocol; => Used for Experiment 1 see Example 7.3.1
add 25 µl of proteinase K to 425 µl of plasma sample, vortex,
add 500 µl of lysis buffer, incubate 5 min at room temperature with mechanical
agitation (1300 rpm in Eppendorf mixer),
add 50 µl of MGP suspended in isopropanol (concentration 60 mg/ml), vortex, and
incubate 20 min at room temperature on a roller mixer,
magnetic separation using a Dynal magnetic separator (2 min);
remove unbound fraction through aspiration, and ad 700 µl wash buffer, vortex, separate, aspire;
repeat wash procedure another 4 times,
add 120 µl of DEPC-water, vortex, and elute 10 min at 80° C. in an Eppendorf Thermomixer at 1300 rpm with cups uncapped,
separate beads from aquous supernatant (=eluate) with Dynal magnetic separator (2 min), freeze eluate until further use.

Automated Protocol on in-House-Built Extractor; => Used for Experiment 2 and 3 (see Example 7.3.2 and Example 7.3.3)

Basically the same procedure and reagent set as above. Additionally, an amoured RNA internal control (IC, see below) is spiked into each and every sample, the extraction process is thermostated at ca. 40° C., and volumes are adjusted to 2 ml total volume of lysis mix, i.e.

50 µl IC
50 µl proteinase K
850 µl sample
1000 µl lysis buffer
100 µl MGP suspension
2200 µl wash buffer for 5 wash steps each
125 µl eluent 1.5 ml Manual Protocol; => Used for Experiment 4 (see Example 7.3.4)
add 80 µl of proteinase K to 420 µl of plasma sample, vortex,
add 500 µl of lysis buffer, incubate 10 min at room temperature with mechanical
agitation (1300 rpm in Eppendorf mixer),
add 500 µl of MGP suspended in isopropanol (concentration 6 mg/ml), vortex, and
incubate 20 min at room temperature on a roller mixer,
magnetic separation using a Dynal magnetic separator (2 min);
remove unbound fraction through aspiration, and ad 700 µl wash buffer, vortex, separate, aspire;
repeat wash procedure another 4 times,
add 100 ml of DEPC-water, close the cups, vortex, and elute 15 min at 80° C. in an Eppendorf Thermomixer at 1300 rpm,
separate beads from aquous supernatant (=eluate) with Dynal magnetic separator (2 min), freeze eluate until further use.

| | stock solution | end concentration in PCR/µl |
|---|---|---|
| amplification total reaction volume = 100 µl for all assays HBV: eluate volume for PCR = 20 µl | | |
| Water (PCR-Grade) | | 4 µl |
| DNA-Mastermix | 2-x | 1-x/50 µl |
| MgCl$_2$ | 25 mM | 3.0 mM/12 µl |
| Primer SEQ ID NO 7 | 5 µM | 0.2 µM/4 µl |
| Primer SEQ ID NO 8 | 5 µM | 0.4 µM/8 µl |
| UNG | 1 U/µl | 2 U/2 µl |
| HCV: eluate volume for PCR = 40 µl | | |
| Water (PCR-Grade) | | 18 µl |
| Bicine-Buffer RT 5x | 5-x | 1-x/20 µl |
| MnOAc | 25 mM | 2.5 mM/10 µl |
| DNTP-Mix (dUTP/ DATP/dCTP/dGTP) | 30 mM 10 mM | 0.6 mM 0.2 mM/2 µl |
| Primer SEQ ID NO 5 | 10 µM | 300 nM/3 µl |
| Primer SEQ ID NO 6 | 10 µM | 300 nM/3 µl |
| UNG | 1 U/µl | 2 U/2 µl |
| Tth-Polymerase | 5.5 U/µl | 10 U/2 µl |
| HIV: eluate volume for PCR = 40 µl | | |
| Water (PCR-Grade) | | 20 µl |
| Bicine-Buffer RT 5x | 5-x | 1-x/20 µl |
| MnOAc | 25 mM | 1.25 mM/5 µl |
| dNTP-Mix (dUTP/ dATP/dCTP/dGTP) | 10 mM | 0.2 mM/2 µl |
| Primer SEQ ID NO 3 | 5 µM | 0.2 µM/4 µl |
| Primer SEQ ID NO 4 | 5 µM | 0.2 µM/4 µl |
| UNG | 1 U/µl | 2 U/2 µl |
| Tth-Polymerase | 5.5 U/µl | 15 U/3 µl |

After PCR, UNG is blocked through the addition of laurylsarcosin concentration 1% use level.

Thermocycling profiles are as follows:

| HBV: | UNG-step | 1x | 10 min | 37° C. |
|---|---|---|---|---|
| | PCR | 35x | 30 sec | 92° C. |
| | | | 30 sec | 55° C. |
| | | | 40 sec | 72° C. |
| HCV: | UNG-step | 1x | 10 min | 37° C. |
| | reverse transcriptase step | 1x | 30 min | 60° C. |
| | denaturation | | 1 min | 95° C. |
| | PCR | 2x | 10 sec | 95° C. |
| | | | 20 sec | 60° C. |
| | | 33x | 15 sec | 90° C. |
| | | | 20 sec | 60° C. |
| | follow-up incubation | | 7 min | 72° C. |

-continued

| HIV: | UNG-step | 1x | 10 min | 37° C. |
| --- | --- | --- | --- | --- |
| | reverse transcriptase step | 1x | 30 min | 60° C. |
| | PCR | 4x | 10 sec | 95° C. |
| | | | 10 sec | 55° C. |
| | | | 10 sec | 72° C. |
| | | 31x | 10 sec | 95° C. |
| | | | 10 sec | 60° C. |
| | | | 10 sec | 72° C. | detection on modified Elecsys 1010®

| reagent | volume (HBV, HCV, HIV) | incubation time (HBV, HCV, HIV) |
| --- | --- | --- |
| PCR product | 10 µl | |
| denaturation solution | 35 µl | 5 min |
| detection probe | 120 µl | 30 min |
| SA-beads | 35 µl | 10 min |

7.2 Homogeneous Functional Assays: 5'-Nuclease-assay-technology on a Cobas Taqman®

7.2.1 General Considerations

Lysis of viral particles as well as adsorption, purification and elution of nucleic acids extracted from the sample are conducted as described above (see Example 7.1.2). Again, amplification of target molecules is described by the equation $N_i = N_0 \times (1+E)^n$, with $N_0$=number of molecules at the start of the polymerase chain reaction $N_i$=number of molecules at the end of polymerase chain reaction E=efficiency of amplification=$0 \leq E \leq 1$ n=number of reaction cycles=typically $40 \leq n \leq 60$ in this case.

With 5'-nuclease technology, however, amplification and detection reactions, respectively, are closely interwoven, and occur in solution phase, i.e. without solid phase immmbilisation and corresponding washing steps (=homogeneous PCR). To this end, detection probes with 2 particular chemical modification are added to the PCR mastermix. One of these modifications is a fluorogenic reporter group (R, for instance a derivative of 6-carboxy-fluorescein) covalently attached to the backbone of the probe, the other one is a dye (for instance a polymethine-cyanine derivative) capable of absorbing the fluorescent light of the reporter and to quench it (quencher). The quencher is typically attached to the probe backbone at the 5'-end, whereas the reporter is located within the oligo sequence, spaced from the quencher by a number of nucleotide building blocks. These probes bind to the target nucleic acid (sense or anti-sense strand) close to the 3'-end of a primer (reverse or forward). As soon as primer has annealed to the target and DNA-polymerse gets bound to the primer:target hybrid, elongation starts. Due to the 5'-nuclease activity of the enzyme, simultaneously with copy strand synthesis the probe is cleaved as soon as the polymerase reaches the probe binding site, reporter and quencher get separated and the fluorescent signal becomes measurable. This process is repeated with every cycle, and more and more fluorescent reporter is accumulated in solution until reagent depletion at the end of the reaction. So, in a signal-over-time plot, sigmoidal growth curves are generated. The bigger $N_0$, the earlier the signal curve rises above noise level.

The point on the time axis, where the fluorescent signal can be significantly distinguished from background signal is called threshold cycle (ct). ct is a measure of assay sensitivity: the smaller the ct-value, the more sensitive is the assay. ct values can be calculated by means of different mathematical operations, for example cut-off approaches (average background signal intensity multiplied by a constant factor yields a cut-off signal intensity to discern negative from positive) or approaches where the location of the maximum of the first differentiation of the signal-over-time curve (i.e. the steepness profile), or the location of the maximum of the second differentiation on the time axis, are computed and defined as ct.

This amplification/detection technology allows for real-time monitoring of PCR and for closed-tube processing as well, i.e. in contrast to standard procedures, the PCR tubes remains closed after pipetting eluate and mastermix which effectively reduces contamination risks.

Moreover, if one uses primer and probe sets for different viral species (and, thus, different analyte molecules and target sequences) combined in one mastermix, it is possible to perform multiple amplification/detection reactions simultaneously, depending on the viral load of the individual under inspection. This is the basis for so-called multiplex assays.

What is more, due to the generic nature of MGP based sample preparation, all nucleic acids present in the sample are extracted by way of physico-chemical adsorption to the particle surface, independent of sequence characteristics. This will also include human DNA (hDNA), released from disrupted blood cells, e.g. leucocytes, the titer of which may differ widely according to the physiological or pathological status of the individual blood sample donor. For instance, in cases of autoimmune diseases like SLE, hDNA levels may be elevated substantially. So, hDNA and one or more pathogenic nucleic acids present in a given sample constitute a mixture of various nucleic acids of different sequence specificities which are co-extracted. They constitute a matrix of polynucleotides that are extracted without discrimination, followed by sequence-specific amplification and detection of target nucleic acids via interaction with specific primers and probes under appropriate reaction conditions.

Given a pathological level of 4000 ng/ml hDNA in plasma in case of SLE, and a low viral load of 50 copies of viral genomic RNA per ml of plasma, and 10000 nucleotides per genomic RNA. With ca. 325 dalton (1 dalton=$1.66 \times 10^{-24}$ g) per nucleotide, 50 copies or 500000 nucleotides of target RNA make ca. $2.7 \times 10^{-7}$ ng per ml of plasma, resulting in a relative abundance of target: non-target nucleic acid of approximately $1:10^{+12}$!

hat is more, in order to monitor the whole process, an artificial nucleic acid construct may be added to the samples, preferably packaged (armored) in a modified virus particle, which is co-extracted and co-amplified with the natural target. This internal control (IC) features a unique probe binding region for an IC detection probe, which differs from target-specific probes by a different reporter group with distinguishable emission characteristics. Thus, IC signal can be discerned from target signal, and as the IC is known to be present in the sample, it functions as a monitoring agent. So, multi-labeling expands the utility of multiplex assay technology. The internal control (IC) is described in WO98/00547.

7.2.2 Experimental Protocol
7.2.2.1 Reagents
7.2.2.1.1 Sample Preparation

See above (Example 7.1.2=> automated protocol on in-house-built extractor)

7.2.2.1.2 5'-Nuclease-Assay, Reactants & Reaction Conditions

| Reagent | Concentration of stock solution | Final concentration in the test | Addition (µl/ reaction) |
|---|---|---|---|
| Mn(OAc)$_2$ pH 6.5 | 50 mM | 3 mM | 5.75 |
| dNTPs | | | 2.50 |
| (dG, dA, dC) | 100 mM | 300 µM | |
| (dT) | | 50 µM | |
| (dU) | | 500 µM | |
| DEPC-H$_2$0 | — | | 9.50 |
| Glycerol | 80% | 5.64% in total 2.8% added here* | 3.50 |
| K Oac pH 7.5 | 2 M | 100 mM | 5.00 |
| Tricine pH 8.3 | 1 M | 50 mM | 5.00 |
| DMSO | 80% | 5.0% | 6.25 |
| Primer SEQ ID NO 12 | 50 µM | 150 nM | 0.30 |
| Primer SEQ ID NO 13 | 50 µM | 150 nM | 0.30 |
| Primer SEQ ID NO 14 | 50 µM | 400 nM | 0.80 |
| Primer SEQ ID NO 15 | 50 µM | 150 nM | 0.30 |
| Primer SEQ ID NO 16 | 50 µM | 400 nM | 0.80 |
| Primer SEQ ID NO 17 | 50 µM | 150 nM | 0.30 |
| Primer SEQ ID NO 18 | 50 µM | 150 nM | 0.30 |
| Probe SEQ ID NO 19 | 50 µM | 100 nM | 0.20 |
| Probe SEQ ID NO 20 | 50 µM | 100 nM | 0.20 |
| Probe SEQ ID NO 21 | 50 µM | 100 nM | 0.20 |
| Probe SEQ ID NO 22 | 50 µM | 100 nM | 0.20 |
| UNG | 2.4 U/µl | 10 U | 4.20 |
| ZO5 | 10 U/µl | 40 U | 4.00 |
| Aptamer SEQ ID NO 23 | 50.4 µM | 200 nM | 0.40 |

*The rest of glycerol is added through the enzymes ZO5 (a mutein of the Tth-DNA-polymerase) and UNG (uracil-N-glycosidase).

The common multiplex thermocycling profile for all test parameters is as follows:

| UNG-step | 45° C. - 10 min |
|---|---|
| denaturation | 94° C. - 30 sec |
| reverse transcription | 58° C. - 30 min |
| PCR | 95° C. - 20 sec/59° C. - 50 sec 5x |
| | 91° C. - 15 sec/52° C. - 50 sec 55x |

7.2.2.1.3 Sequences

| Primer: | |
|---|---|
| HIV-forward: | SEQ ID NO 12 |
| HIV-forward: | SEQ ID NO 13 |
| HIV-reverse: | SEQ ID NO 14 |
| HCV-forward: | SEQ ID NO 15 |
| HCV-reverse: | SEQ ID NO 16 |
| HBV-forward: | SEQ ID NO 17 |
| HBV-reverse: | SEQ ID NO 18 |
| Probes: | |
| HIV: | SEQ ID NO 19 |
| HCV: | SEQ ID NO 20 |
| HBV: | SEQ ID NO 21 |
| IC: | SEQ ID NO 22 |
| Aptamer: | SEQ ID NO 23 |

Melting temperature of the DNA polymerase-aptamer complex=51.7° C. (=50% dissociation)

Terminology of the Chemical Derivatisations:

Some of the oligonucleotides are derivatised with Cy5 which is a Pentamethine-di-indocarbocyanine coupled to alkylphosphatidyl-linker (Pharmacia Biotech Cy5-N-ethyl-phosphoramidite) and which functions as quencher (O); $\lambda_{EX}$=630 nm, $\lambda_{EM}$=665 nm. Some of the oligonucleotides are derivatised with FAM which is 6-carboxy-fluorescein coupled to a 2-(amino-cyclohexyl-)propane-1,3-diol-linker (Biogenex CX-FAM-phosphoramidite) and which functions as s reporter for targets (R); $\lambda_{EX}$=485 nm, $\lambda_{EM}$=515 nm. Some of the oligonucleotides are derivatised with which is hexachloro-6-carboxy-fluorescein coupled to a 2-(amino-cyclohexyl-)propane-1,3-diol-linker (Biogenex CX-HEX-phosphoramidite) and which functions as reporter for the internal control (R); $\lambda_{EX}$=530 nm, $\lambda_{EM}$=585 nm 7.2.2.1.4 Reaction Conditions The reaction conditions are described in the results of the experiments (see Example 7.3).

7.2.2.1.5 Other Materials
- virus-negative plasma (O-Matrix, single plasma or Plasma-Pool), e.g. citrate-plasma or EDTA-plasma
- virus-positive plasma or virus-containing culture supernatants, which can be used to adjust certain virus titers by mixing with O-matrix in appropriate ratios.
- alternatively: in vitro-transcripts with the target-sequences to be investigated
- human placental DNA (a. genomic, Sigma cat. no. D4642; b. fragmented, Sigma cat. no. D3287), added to the samples to simulate pathological conditions which lead to the enhanced release of intracellular substances and thus to enhanced levels of DNA/RNA in the blood, e.g. auto immune disease as SLE or hemolysis.

7.3 Results of the Functional Tests 7.3.1 Experiment 1

Different MGP-samples of the type EJ/CERAC are investigated with the methods described in 7.1. The test variable was the spraying pressure:

EJ0100.5R—1.5 bar
EJ0106.5R—2.5 bar
EJ0107.5R—3.5 bar
EJ0108.5R—4.3 bar

It could be demonstrated that with increasing spraying pressure, i.e. shift towards smaller average bead diameter, the unspecific binding (USB) decreases whereas the highly specific signal generation is unchanged which results in elevated signal-to-noise ratios The virus titer adjustment 0.5×GG is approximately 100 sgu/ml (sgu=signal generating units) in the case of HBV, and approximately 150 sgu/ml in the case of HIV. The data are summarized in Table 7.

7.3.2 Experiment 2:

Two variants each of the type EJ/MMB and EJ/CERAC, respectively, are functionally compared using the method as described in Example 7.2 in conjunction with multipool (MP) and individual (PL) plasma samples. EJ0047.2R (MMB) and EJ0100.5R (CERAC) are sprayed under standard conditions, i.e. 1.5 bar, 230° C. inlet temperature and approximately 110° C. outlet temperature. EJ0102.2R (MMB) and EJ0108.5R (CERAC) are development variants with regard to the spraying conditions (inlet temperature decreased to 200° C. [MMB]), and spraying pressure increased to 4.3 bar [CERAC]). The results are summarized in Table 8 and show the potential of the CERAC nano-core particles to obtain higher sensitivity as exemplified by the earlier threshold cycle and/or the larger signal differences (saturation signal minus noise level, S-N).

7.3.3 Experiment 3

Several MGP preparations of the type EJ/MMB and EJ/CERAC (see Table 9) are functionally compared using the method as described in Example 7.2. The results are summarized in Table 10 and show the potential of the of the EJ0096.5R-01-type particles to obtain higher sensitivity as exemplified by the earlier threshold cycle or higher hit rate irrespective of the particular assay.

7.3.4 Experiment 4

Several MGP preparations of the type EJ/MMB and EJ/CERAC are functionally compared using the method as described in Example 7.1 wherein the adsorption incubation is conducted with or without shaking. Thereby, the sedimentation velocity becomes decisive, i.e. the higher the sedimentation velocity the higher the number of particles which are removed from the interaction with the analyte in the forming precipitate. In contrast, if the sedimentation velocity is smaller then time span is longer in which analyte molecules from the liquid may adsorb to the surface of the adsorbent.

The results are summarized in Table 11 (EJ0047.2R was used as a reference) show that without mechanical agitation the loss of performance is highest (>40%) with the MMB-type (differs considerably from the characteristics of this invention), and least, or practically absent, with the CERAC-type (most close to the characteristics of the invention within this series).

To be able to assess the functionality of the different types of MGP thoroughly, a performance index was calculated for each type in the following way:

the eluate of several batches for each type of MGP and each titer level, respectively, are pooled into 1 eluate pool out of each eluate pool, 3 amplifications were performed for each assay (HIV, HCV, HBV)

each amplificate was measured in singlicate on the modified Elecsys 1010® signals are averaged for each type of MGP, assay, and titer level signal-to-noise (S/N) factors are calculated for each type of MGP and assay, respectively, i.e. low titer (weakly positive) over O-matrix (negative), and elevated titer over O-matrix S/N factors are normalized to the reference type of MGP at the time calculation of the sum of normalized S/N factors for each type of MGP, cumulated over all assays and titer levels; S/N factors for the low titer range are weighted 2-fold relative to those for the high titer level so as to pronounce sensitivity aspects the resulting sum is assigned performance index for each type of MGP investigated

7.3.5 Experiment 5

Different types of MGP were used to extract HCV in vitro transcripts which were diluted to various titer levels in diluent containing 10 mmol/l Tris, pH 80, 1 mM EDTA, 20 µg/ml poly-A-RNA and 0.05% $NaN_3$, and spiked into pooled plasma. Human background DNA (hBG-DNA) was spiked at 0 or 4000 ng/ml into the sample, respectively. Surprisingly, it is possible to reduce interference by hBG-DNA by way of bead selection, as demonstrated by the data presented in Table 12.

7.3.6 Experiment 6

Various types of MGP were used to process HCV positive plasma samples. Human background DNA (hBG-DNA) was spiked at 0 or 4000 ng/ml into the sample, respectively. Again, a significant impact of bead size and bead geometry is being observed. MGP preparation EJ0096.5R, which represents the MGP quality according to the present invention the most, shows very clearcut advantages both in terms of minimal shift of ct values, and reducing loss of specific signal generation (S-N), as indicated by the data presented in Table 13.

TABLE 1

| Company | Abbreviation | Description | Code (see Example 1.4) |
|---|---|---|---|
| — | — | No pigment | 0 |
| Merck Darmstadt, Germany | BM | Merck Black Mica: Small plates of mica (support), diameter = 10-60 µm, thickness approximately 1-2 µm, $Fe_3O_4$-ashlars and $TiO_2$-grains are attached; typically, several pigment units are aggregated (Merck Iriodin ®) | 1 |
| Merck Darmstadt, Germany | MMB | Merck Microna Matte Black Small plates of mica (support), diameter = 3-15 µm, thickness approximately 1-2 µm, $Fe_3O_4$-ashlars are attached; typically, several pigment units are aggregated | 2 |
| BASF Ludwigshafen, Germany | BASF-FA | BASF iron oxide FA28-41: Needles in the nanoscale range made from $\gamma$-$Fe_2O_3$, length approximately 200-400 nm, very high tendency to aggregate to particles in the µ-scale because of the form and large highly structured surface | 4 |
| Cerac, Milwaukee, WI, USA | CERAC | CERAC $\gamma$-$Fe_2O_3$ (Catalogue number I-2012, distributed by Chemco Chemieprodukte GmbH in Germany) $\gamma$-$Fe_2O_3$-microbeads in the nanoscale (pure ferric oxide), diameter = 23 nm, non-aggregating | 5 |
| Strem Chemicals, Newburyport, MA, USA | STREM | STREM $Fe_3O_4$ >95% (Catalogue-No.: 93-2616) Microbeads in the nanoscale range made from precipitated $Fe_3O_4$, diameter = 200-500 nm, strong tendency to aggregate to particles in the µ-range | 7 |
| BASF, Ludwigshafen, Germany | BASF-CE | Beads in the µ-scale made from metallic iron BASF Carbonyl iron powder HQ: 10% <1.04 µm, 50% <1.91 µm, 90% <3.71 µm | 8 |
| | | BASF Carbonyl iron powder SU: 10% <0.43 µm, 50% <0.93 µm, 90% <1.81 µm | 9 |

TABLE 2

| Code | M1 TEOS | Water (ml/100 ml TEOS) | Alcohol | Alcohol (ml/100 ml TEOS) | Ageing (h) | spray pressure (bar) | Nozzle | inlet temperature (° C.) | Temperature in air before FA (° C.) | temperature in N$_2$ after FA (° C.) | temperature in O$_2$ after FA (° C.) | temperature treatment in bottle under air (° C.) |
|---|---|---|---|---|---|---|---|---|---|---|---|---|
| 0005 | 1750 | 13.33 | EtOH | 50 | 1 | 1.5 | A | 230 | 250 | 675 | 300 | 300 |
| 0009 | 1750 | 13.33 | EtOH | 50 | 1 | 1.5 | A | 230 | 250 | 675 | 300 | 300 |

| Code | M1 TEOS | Water (ml/100 ml TEOS) | Alcohol | Alcohol (ml/100 ml TEOS) | Ageing (h) | Pigment (g/100 g Oxid) | Spray pressure (bar) | Nozzle | inlet temperature (° C.) | Temperature treatment in air (° C.) | temperature (post) in N$_2$ (° C.) | temperature treatment in air (° C.) | temperature treatment in bottle under air (° C.) |
|---|---|---|---|---|---|---|---|---|---|---|---|---|---|
| 0045 | 1400 | 13.33 | EtOH | 50 | 0 | | 1.5 | A | 230 | 200 | 675 | 300 | 200 |
| 0046 | 250 | 13.33 | EtOH | 50 | 0 | | 5 | Büchi | 150 | 200 | 675 | 300 | 200 |
| 0047 | 1300 | 14.13 | EtOH | 137 | 0 | | 1.5 | A | 230 | 250 | 750 | 200 | 200 |
| 0096 | 150 | 14.1 | EtOH | 141 | 0 | 230 | 6 | Büchi | 150 | 200 | 750 | 200 | 200 |
| 0097 | 150 | 14.1 | EtOH | 141 | 0 | 191 | 6 | Büchi | 150 | 200 | 750 | 200 | 200 |
| 0098 | 210 | 14.1 | EtOH | 141 | 0 | 230 | 6 | Büchi | 150 | 200 | 690 | 200 | 200 |
| 0099 | 210 | 14.1 | EtOH | 141 | 0 | 230 | 6 | Büchi | 150 | 200 | 710 | 200 | 200 |
| 0100 | 840 | 14.1 | EtOH | 141 | 0 | 230 | 1.5 | A | 230 | 200 | 750 | 200 | 200 |
| 0101 | 840 | 14.1 | EtOH | 141 | 0 | 191 | 1.5 | A | 230 | 200 | 750 | 200 | 200 |
| 0102 | 1300 | 14.1 | EtOH | 141 | 0 | 230 | 1.5 | A | 230 | 200 | 750 | 200 | 200 |
| 0106 | 840 | 14.1 | EtOH | 141 | 0 | 230 | 2.5 | A | 230 | 200 | 750 | 200 | 200 |
| 0107 | | | | | | | 3.5 | A | 230 | 200 | 750 | 200 | 200 |
| 0108 | | | | | | | 4.3 | A | 230 | 200 | 750 | 200 | 200 |
| 0109 | 8000 | 14.1 | EtOH | 141 | 0 | 230 | 1.5 | A | 210 | 200 | 750 | 200 | 200 |
| 0111 | 1300 | 14.1 | EtOH | 141 | 0 | 230 | 1.5 | A | 210 | 200 | 750 | 200 | 200 |
| 0119 | 1200 | 14.6 | EtOH | 130 | 0 | 230 | 1.5 | A | 210 | 200 | 750 | 200 | 200 |
| 0124 | | | | | | | 6 | Büchi | 150 | 200 | 750 | 200 | 200 |
| 0128 | 7830 | 14.1 | EtOH | 141 | 0 | 230 | 1.5 | A | 230 | 200 | 750 | 200 | 200 |
| 0129 | | | | | | | 1.5 | A | 200 | 200 | 750 | 200 | 200 |
| 0130 | | | | | | | 4.3 | A | 200 | 200 | 750 | 200 | 200 |
| 0131 | | | | | | | 6 | A | 200 | 200 | 750 | 200 | 200 |

TABLE 3

| Sample | Outlet temperature (° C.) | Density (g/cm$^3$) | Extinction (280 nm) | Extinction (400 nm) | Iron solubility (mg/l) | Magnetic force (g/250 mg) |
|---|---|---|---|---|---|---|
| RN0005.2E-01 | 116 | 3.420 | 0.037 | 0.027 | <determination limit | 16.04 |
| RN0009.1E-01 | 119 | 3.155 | 0.106 | 0.093 | <determination limit | 9.50 |
| EJ0028.2R-01 | 118 | 3.602 | 0.019 | 0.024 | <determination limit | 12.25 |
| RN0045.4R-01 | 130 | 3.647 | 0.032 | 0.034 | <determination limit | 9.23 |
| RN0046.7R-01 | 98 | 3.866 | 0.013 | 0.013 | <determination limit | 13.12 |
| RN0045.5R-01 | 120 | 3.802 | 0.019 | 0.017 | 0.047 | 9.52 |
| EJ0047.2R-01 | 118 | 3.659 | 0.022 | 0.018 | <determination limit | 12.00 |
| EJ0096.5R-01 | 96 | 4.203 | 0.001 | 0.000 | <determination limit | 13.53 |
| EJ0096.7R-01 | 96 | 4.328 | 0.000 | 0.001 | <determination limit | 18.36 |
| EJ0097.4R-01 | 96 | 3.859 | 0.001 | 0.000 | <determination limit | 15.17 |
| EJ0098.8R-01 | 95 | 5.588 | 0.065 | 0.055 | <determination limit | 15.76 |
| EJ0099.9R-01 | 95 | 5.538 | 0.103 | 0.101 | 0.016 | 14.13 |
| EJ0100.7R-01 | 122 | 4.196 | 0.027 | 0.003 | <determination limit | 16.29 |
| EJ0100.5R-01 | 126 | 4.069 | 0.012 | 0.012 | <determination limit | 12.42 |
| EJ0101.4R-01 | 119 | 4.079 | 0.083 | 0.084 | 0.015 | 11.67 |
| EJ0102.2R-01 | 128 | 3.668 | 0.009 | 0.009 | <determination limit | 13.36 |
| EJ0047.2R-07 | 118 | 3.612 | 0.024 | 0.022 | 0.159 | 11.26 |
| EJ0100.5R-02 | 127 | 4.107 | 0.029 | 0.023 | 0.054 | 14.51 |
| EJ0100.5R-03 | 127 | 4.173 | 0.063 | 0.045 | 0.126 | 10.44 |
| EJ0106.5R-01 | 127 | 4.191 | 0.004 | 0.004 | 0.025 | 10.09 |
| EJ0107.5R-01 | 127 | 4.235 | 0.016 | 0.009 | 0.037 | 10.25 |
| EJ0108.5R-01 | 127 | 4.233 | 0.026 | 0.026 | 0.039 | 11.56 |
| EJ0109.2R-01 | 110 | 3.700 | 0.046 | 0.043 | 0.028 | 11.23 |
| EJ0111.5R-01 | 117 | 3.612 | 0.071 | 0.036 | 0.166 | 16.48 |
| EJ0111.5R-02 | 121 | 4.082 | 0.065 | 0.040 | 0.161 | 15.95 |
| EJ0124.5R-01 | | 3.992 | 0.001 | 0.001 | 0.051 | 17.57 |
| EJ0128.5R-01 | 125 | 4.078 | 0.023 | 0.028 | | 8.97 |
| EJ0129.5R-01 | 92 | 4.013 | 0.044 | 0.043 | | 9.64 |
| EJ0130.5R-01 | 87 | 4.022 | 0.031 | 0.036 | | 11.70 |
| EJ0131.5R-01 | 89 | 3.908 | 0.033 | 0.037 | | 11.73 |
| EP0119.5R-01 | 127 | 4.110 | 0.003 | 0.003 | 0.079 | 17.15 |

TABLE 4

| Lot | BET surface [m²/g] | Remarks |
|---|---|---|
| EJ0096.5R-01 | 26.85 | Cerac, small spray dryer, 6 bar |
| EJ0100.5R-01 | 8.95 | Cerac, big spray dryer, 1, 5 bar |
| EJ0101.4R-01 | 8.47 | BASF FA, big spray dryer, 1, 5 bar |
| RN0005.2E-01 | 3.54 | MERCK MMB, big spray dryer, 1, 5 bar |
| RN0009.1E-01 | 3.25 | MERCK BM, big spray dryer, 1, 5 bar |
| EJ0099.9R | 0.74 | BASF CE-SU, big spray dryer, 6 bar |
| EJ0100.7R | 8.53 | STREM, big spray dryer, 1, 5 bar |

TABLE 5

| MGP-type | Size of the isolated cores | Constitution | Form | $t_{1/2}$ sedimentation [min] | $t_{1/2}$ separation [sec] |
|---|---|---|---|---|---|
| MMB | 3–15 μm | Aggregated | Plates | 3.9 | 14 |
| CERAC | 23 nm | Singular | Beads | >>10 | 16 |
| STREM | 300–500 nm | Aggregated | Beads | 4.8 | 10 |
| BASF-FA | 200–300 nm | Aggregated | Needles | 4.6 | 12 |

TABLE 6

| MGP-sample | $t_{0,9}$ (90%-Wert) sedimentation [min] | $t_{1/2}$ (50%-Wert) sedimentation [min] |
|---|---|---|
| EJ0100.5R-01 | 0.35 | 2.78 |
| EJ0108.5R-01 | 0.62 | 7.58 |
| EJ0096.5R-01 | 1.39 | 19.85 |

TABLE 7

| MGP | USB [counts] - 0-matrix HIV | USB [counts] - 0-matrix HBV | SB [counts] - 0.5 × GG HIV | SB [counts] - 0.5 × GG HBV |
|---|---|---|---|---|
| EJ0100.5R-01 | 4997 | 2277 | 20380 | 80292 |
| EJ0100.5R-02 | 6100 | 3590 | 22036 | 53417 |
| EJ0100.5R-03 | 4856 | 2270 | 19791 | 65109 |
| EJ0106.5R-01 | 4427 | 2263 | 19030 | 75128 |
| EJ0107.5R-01 | 3940 | 2261 | 19255 | 68285 |
| EJ0108.5R-01 | 3429 | 2217 | 20048 | 80426 |

TABLE 8

| Sample | MGP lot# | HBV Ct | HBV S-N | HCV ct | HCV S-N |
|---|---|---|---|---|---|
| MP2 | EJ0047.2 | 40.49 | 19.88 | 41.68 | 12.6 |
| MP2 | EJ100.5 | 40.96 | 21.80 | 43.08 | 12.74 |
| MP2 | EJ0102.2 | 41.93 | 21.39 | 44.74 | 10.10 |
| MP2 | EJ0108.5 | 40.09 | 22.01 | 47.36 | 10.61 |
| Pl. 1/2 | EJ0047.2 | 41.03 | 18.14 | — | — |
| Pl. 1/2 | EJ100.5 | 40.12 | 19.31 | — | — |
| Pl. 1/2 | EJ0102.2 | 41.81 | 22.80 | 44.69 | 14.30 |
| Pl. 1/2 | EJ0108.5 | 39.93 | 21.77 | 43.27 | 12.58 |
| Pl. 4/5 | EJ0047.2 | 46.33 | 12.83 | 39.54 | 18.30 |
| Pl. 4/5 | EJ100.5 | 40.82 | 15.12 | 38.24 | 21.48 |
| Pl. 4/5 | EJ0102.2 | 42.49 | 19.65 | 39.24 | 19.05 |
| Pl. 4/5 | EJ0108.5 | 47.33 | 9.51 | 39.47 | 17.81 |
| Pl. 6/8 | EJ0047.2 | 41.08 | 20.83 | 49.44 | 9.46 |
| Pl. 6/8 | EJ100.5 | 40.68 | 23.16 | 48.98 | 10.31 |
| Pl. 6/8 | EJ0102.2 | 40.50 | 22.49 | 54.50 | 6.50 |
| Pl. 6/8 | EJ0108.5 | 38.79 | 18.60 | 50.41 | 8.61 |
| Pl. 6/8 | EJ0047.2 | 44.16 | 17.26 | 41.40 | 10.59 |
| Pl. 6/8 | EJ100.5 | 42.97 | 18.59 | 41.01 | 11.33 |
| Pl. 6/8 | EJ0102.2 | 44.49 | 12.41 | 42.18 | 11.32 |
| Pl. 6/8 | EJ0108.5 | 41.24 | 18.73 | 41.46 | 10.80 |

Counting statistics: Which type scores better ?

| "standard samples" MMB:CERAC | | "development variants" MMB:CERAC | | total: best type per sample * assay MMB:CERAC | |
|---|---|---|---|---|---|
| Ct | S-N | Ct | S-N | Ct | S-N |
| 2:7 | 0:9 | 3:7 | 5:5 | 1:9 | 3:7 |

(1 comparison could not be evaluated)

TABLE 9

| MGP | Description |
|---|---|
| EJ0096.5R | 6.0 bar spraying pressure, 150° C. inlet temperature, Büchi-laboratory equipment. This preparation approximates the characteristics according to the invention very well, see FIG. 16. |
| EJ0111.5R | 1.5 bar spraying pressure, 230° C. inlet temperature, Nubilosa- laboratory equipment |
| EP0119.5R | 1.5 bar spraying pressure, 230° C. inlet temperature, Nubilosa- laboratory equipment, changed glass composition without Zn-acetate, K-methanolate substituted by K-acetate, with identical stoichiometry |
| EJ108.5R | 4.3 bar spraying pressure, 230° C. inlet temperature, Nubilosa- laboratory equipment |

TABLE 10 ct-values (HBV)

| Parameter | Titer [sgu/ml] | MGP lot EJ0111.5R-02 AVG | MGP lot EP0119.5R AVG | MGP lot EJ0096.5R AVG | MGP lot EJ0108.5R AVG |
|---|---|---|---|---|---|
| ct-calculation via maximum of first differentiation | | | | | |
| HBV | NK | — | — | — | — |
| | 100 | 46.1 | 44.1(6/6) | 43.4 | 44.2 |
| | 40 | 47.6 | 46.5(7/8) | 45.5(7/8) | 46.7(6/7) |
| | 20 | 50.6(6/8) | 46.1(6/8) | 46.8(7/8) | 50.0(4/8) |
| | 10 | 47.6(5/8) | 50.1(5/8) | 46.8(4/8) | 47.7(3/7) |
| | 5 | 51.2(3/8) | 48.6(4/8) | 47.8(5/8) | 49.7(4/7) |
| | hit rate | 75% | 74% | 77.5% | 67.5% |
| ct-calculation via cut-off formula | | | | | |
| HBV | NK | — | — | — | — |
| | 100 | 44.2 | 41.7(6/6) | 41.5 | 41.9 |
| | 40 | 45.5 | 44.1(7/8) | 42.7(6/8) | 45.0(6/7) |
| | 20 | 47.7(6/8) | 43.5(6/8) | 44.3(7/8) | 47.2(6/8) |
| | 10 | 45.5(5/8) | 47.7(5/8) | 44.4(6/8) | 45.6(3/8) |
| | 5 | 49.3(3/8) | 45.7(4/8) | 45.4(4/8) | 46.6(4/7) |
| | hit rate | 75% | 74% | 77.5% | 71% | ct-values (HCV)

| Parameter | Titer [IU/ml] | MGP lot EJ0111.5R-02 AVG | MGP lot EP0119.5R AVG | MGP lot EJ0096.5R AVG | MGP lot EJ0108.5R AVG |
|---|---|---|---|---|---|
| ct-calculation via maximum of first differentiation | | | | | |
| HCV | NK | — | — | — | — |
| | 400 | 42.7 | 42.5(7/8) | 41.8 | 42.6(7/7) |
| | 80 | 44.4(7/8) | 44.1(6/6) | 44.2(7/8) | 44.2(7/7) |
| | 60 | 45.1 | 44.7(7/7) | 44.6(7/7) | 45.1(6/6) |

TABLE 10-continued

|  |  |  |  |  |  |
|---|---|---|---|---|---|
|  | 40 | 46.2(7/8) | 45.8(7/7) | 43.9(5/7) | 44.5(7/7) |
|  | 20 | 46.5(5/8) | 46.3(7/7) | 45.0(6/8) | 47.4(4/8) |
|  | hit rate | 90% | 97% | 84% | 88.5% | ct-calculation via cut-off formula

| | | | | | |
|---|---|---|---|---|---|
| HCV | NK | — | — | — | — |
|  | 400 | 41.8 | 41.6(7/8) | 40.9 | 41.7(7/7) |
|  | 80 | 44.6(7/7) | 44.0(6/6) | 43.4(7/8) | 44.5(7/7) |
|  | 60 | 44.7 | 45.3(7/7) | 45.1(6/7) | 44.3(5/6) |
|  | 40 | 47.9(7/8) | 46.1(7/7) | 44.7(4/7) | 47.5(7/7) |
|  | 20 | 49.6(5/8) | 47.2(7/7) | 45.3(5/8) | 47.4(4/8) |
|  | hit rate | 90% | 97% | 79% | 86% | ct-values (HIV)

ct-calculation via maximum of first differentiation

| Parameter | Titer [sgu/ml] | MGP lot EJ0111.5R AVG | MGP lot EP0119.5R AVG | MGP lot EJ0096.5R AVG | MGP lot EJ0108.5R AVG |
|---|---|---|---|---|---|
| HIV | NK | — | — | — | — |
|  | 30 | 43.2(6/8) | 46.9(3/8) | 43.9(3/7) | 41.9(1/7) |
|  | 60 | 42.7(4/7) | 42.6(4/7) | 42.8(7/7) | 42.4(2/7) |
|  | 150 | 42.4(5/7) | 42.0 | 41.7(6/6) | 42.6(6/8) |
|  | 300 | 41.9(5/5) | 41.0(5/5) | 41.5(6/6) | 41.3(6/6) |
|  | 600 | 41.6(7/7) | 40.8(6/6) | 40.8(5/5) | 41.5 |
|  | hit rate | 79% | 76% | 87% | 64.0% | ct-calculation via cut-off formula

| Parameter | Titer [IU/ml] | MGP lot EJ0111.5R AVG | MGP lot EP0119.5R AVG | MGP lot EJ0096.5R AVG | MGP lot EJ0108.5R AVG |
|---|---|---|---|---|---|
| HIV | NK | — | — | — | — |
|  | 30 | 44.3(1/8) | 47.3(2/8) | 46.8(1/7) | —(0/7) |
|  | 60 | 50.3(3/7) | 54.1(1/7) | 51.4(4/7) | —(0/7) |
|  | 150 | 47.4(5/7) | 43.7(5/8) | 45.5(5/7) | 52.2(2/8) |
|  | 300 | 42.2(5/5) | 44.8(5/5) | 41.6(4/6) | 46.5(6/6) |
|  | 600 | 41.2(7/7) | 41.3(5/6) | 41.1(5/5) | 42.5 |
|  | hit rate | 62% | 53% | 59% | 44% |

TABLE 12

| particles N | HCV-Titer (IVT-RNA) | ΔhDNA | Δct | ΔS- |
|---|---|---|---|---|
| RN0009.1E = big platelets (3-60 μm) | 1000 cp/PCR | 4000 ng/ml | +2 | −6,1 |
| EJ0100.5R = deformed balls (ca. 1-12 μ-range) | ↓ | ↓ | −1 | −3,2 |
| EJ0108.5R = deformed balls* (ca. 1-4 μ-range) |  |  | ±0 | −1,2 |

*high-pressure variant, see sections 7.2.4.2. & 7.3.1, respectively.

note:

(+)Δct = less sensitive (i.e. bias towards false negative results); (−)Δct = more sensitive (bias towards false positive results?)

(−)ΔS-N = less specific signal generation = negative interference

TABLE 13

| particles N (EJ/CERAC throughout) | HCV-Titer (extracted genomic RNA) | ΔhDNA | Δct | ΔS- |
|---|---|---|---|---|
| EJ0096.5R = design goal* | 200 IU/ml sample | 4000 ng/ml | −0,95 | −8,5 |
| EJ0127.5R = standard 13,89 | ↓ | ↓ | −3,08 | — |
| EJ0129.5R = p-variant 12,62 |  |  | −2,30 | — |
| EJ0130.5R = p-variant 10,57 |  |  | −2,62 | — |
| EJ0131.5R = p-variant 12,41 |  |  | −2,46 | — |

*= 0,5-5 μ-range; > 50% sub-μ-scale; big surface area (27 m$^2$/g BET); perfectly spherical beads p-variant = spray-dried at elevated pressure (see section 7.3.1).

TABLE 11

| MGP type | HIV 1 60 sgu/ neg | 600 sgu/ neg | HCV → 480 sgu/ neg | 4800 sgu/ neg | HBV 40 sgu/ neg | 400 sgu/ neg | Performance index Cumulated/ weighted/ normalized | ratio of performance indices Without/with shaking |
|---|---|---|---|---|---|---|---|---|
| EJ0047.2R (reference) | 100 | 100 | 100 | 100 | 100 | 100 | 900 | — |
| EJ0096.5R | 55 | 34 | 44 | 74 | 146 | 112 | 709 | — |
| EJ0096.7R | 47 | 47 | 18 | 8 | 116 | 107 | 523 | — |
| EJ0097.4R | 32 | 54 | 29 | 47 | 169 | 132 | 692 | — |
| RN0045.5R | 85 | 64 | 76 | 63 | 7 | 84 | 545 | — |
| RN0046.7R | 109 | 80 | 43 | 40 | 121 | 135 | 803 | — |
| RN0045.4R | 48 | 93 | 112 | 128 | 136 | 96 | 908 | — |
| EJ0047.2R (reference) | 24 | 24 | 52 | 49 | 93 | 122 | 534 | 0.59 |
| EJ0096.5R | 28 | 23 | 47 | 88 | 102 | 154 | 619 | 0.87 |
| EJ0096.7R | 34 | 23 | 38 | 14 | 99 | 70 | 449 | 0.86 |
| EJ0097.4R | 33 | 36 | 20 | 18 | 101 | 94 | 456 | 0.66 |
| RN0045.5R | 53 | 74 | 60 | 25 | 107 | 72 | 610 | 1.12 |
| RN0046.7R | 141 | 90 | 16 | 8 | 32 | 40 | 518 | 0.64 |
| RN0045.4R | 55 | 113 | 25 | 146 | 78 | 101 | 675 | 0.74 |

The invention claimed is:

1. A procedure for isolating a biological material comprising;
   a) contacting a sample that contains the biological material in a liquid with a composition of magnetic glass particles, wherein each magnetic glass particle comprises at least one magnetic object with a mean diameter between 5 to 500 nm, wherein the glass comprises a metal and metal oxides, wherein the metal is zinc, and the metal oxides are $SiO_2$, $B_2O_3$, $Al_2O_3$, $K_2O$ CaO, and ZnO, under conditions in which the biological material binds non-covalently to the surface of the magnetic glass particle, wherein the binding does not comprise precipitation to lower the solubility of the material to be bound, and
   b) separating the biological material from the liquid.

2. The procedure of claim 1 wherein the biological material is a nucleic acid.

3. The procedure of claim 1 wherein the biological material contains a mixture of nucleic acids, wherein at least one of the nucleic acids is a target nucleic acid indicative of the presence of a certain condition or disease.

4. The procedure of claim 1 wherein the separation is accomplished with the aid of a magnet.

5. The procedure of claim 1 wherein the magnetic particles are not premagnetized when brought into contact with the sample.

6. The procedure of claim 1 wherein the procedure is automatized.

7. The procedure of claim 1 wherein the procedure is in a high-throughput format.

8. The procedure of claim 1 wherein a suspension of the magnetic glass particles is taken from a storage container and partial volumes of the suspension are added to different reaction vessels.

9. The procedure of claim 1 further comprising the steps of:
   (c) washing the magnetic glass particles isolated from the fluid in a buffer that does not cause the biological material to be released from the surface;
   (d) eluting the biological material from the surface of the magnetic glass particles using an elution buffer under conditions in which the biological material separates from the surface of the magnetic glass particle and;
   (e) detecting the purified biological material.

10. The procedure of claim 9, further comprising an amplification step after step (d).

11. The procedure of claim 9 wherein a nucleic acid is detected by a process comprising:
   a) contacting a target nucleic acid with an oligonucleotide comprising a sequence complementary to a region of the target nucleic acid and a labeled oligonucleotide comprising a sequence complementary to a second region of the same target nucleic acid sequence strand, but not including the nucleic acid sequence defined by the first oligonucleotide, to create a mixture of duplexes during hybridization conditions, wherein the duplexes comprise the target nucleic acid annealed to the first oligonucleotide and to the labeled oligonucleotide such that the 3'-end of the first oligonucleotide is adjacent to the 5'-end of the labeled oligonucleotide;

b) maintaining the mixture of step a) with a template-dependent nucleic acid polymerase having a 5' to 3' nuclease activity under conditions sufficient to permit the 5' to 3' nuclease activity of the polymerase to cleave the annealed, labeled oligonucleotide and release labeled fragments; and c) detecting and/or measuring the signal generated by the hydrolysis of the labeled oligonucleotide.

12. The procedure of claim 10, wherein the amplification/detection step is carried out using a polymerase chain reaction in the presence of a blocking oligonucleotide.

13. The procedure of claim 12 wherein the blocking oligonucleotide is an aptamer.

14. The procedure of claim 13 wherein the aptamer has the sequence shown in SEQ ID NO:23.

15. The procedure of claim 12 wherein the amplification and detection reaction is carried out in a homogenous solution-phase multiplex assay format for the simultaneous detection of multiple targets.

16. The procedure of claim 13, wherein a polymerase-aptamer complex is formed, and an annealing temperature of less than 8° C. above a dissociation temperature of the polymerase-aptamer complex is used for at least 5 cycles of the polymerase chain reaction.

17. The procedure of claim 16, wherein the annealing temperature is less than 3° C. above the dissociation temperature of the polymerase -aptamer complex for at least 5 cycles of the polymerase chain reaction.

* * * * *

SEQUENCE LISTING

<160> NUMBER OF SEQ ID NOS: 23

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 1
tcagggcaaa actcagctca ccg                                             23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gatgagttcg tgtccgtaca act                                             23

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide primer (HIV forward)
<220> FEATURE:
<221> NAME/KEY: modified_base
<222> LOCATION: (1)
<223> OTHER INFORMATION: Biotin derivatization

<400> SEQUENCE: 3
agttggagga catcaagcag ccatgcaaat                                      30

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide primer (HIV reverse)
<220> FEATURE:
<221> NAME/KEY: modified_base
<222> LOCATION: (1)
<223> OTHER INFORMATION: Biotin derivatization

<400> SEQUENCE: 4
tgctatgtca gttcccttg gttctct                                          27

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide primer (HCV forward)

<400> SEQUENCE: 5
gcagaaagcg tctagccatg gcgt                                            24

<210> SEQ ID NO 6
<211> LENGTH: 24

```
<212> TYPE: DNA
<213> ORGANISM: Artificial Sequence
<220> FEATURE:
<223> OTHER INFORMATION: Description of Artificial Sequence: Synthetic
      oligonucleotide primer (HCV reverse)
<220> FEATURE:
<221> NAME/KEY: modified_base
<222> LOCATION: (1)
<223> OTHER INFORMATION: Biotin derivatization

<400> SEQUENCE: 6
ctcgcaagca ccctatcagg cagt                                          24

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide primer (HBV forward)

<400> SEQUENCE: 7
ggagtgtgga ttcgcact                                                 18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide primer (HBV reverse)
<220> FEATURE:
<221> NAME/KEY: modified_base
<222> LOCATION: (1)
<223> OTHER INFORMATION: Biotin derivatization

<400> SEQUENCE: 8
tgagatcttc tgcgacgc                                                 18

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide probe (HIV)
<220> FEATURE:
<221> NAME/KEY: modified_base
<222> LOCATION: (1)
<223> OTHER INFORMATION: Ruthenium3+ (tris bipyridyl) derivatisation

<400> SEQUENCE: 9
atcaatgagg aagctgcaga                                               20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide probe (HCV)
<220> FEATURE:
<221> NAME/KEY: modified_base
<222> LOCATION: (1)
<223> OTHER INFORMATION: Ruthenium3+ (tris bipyridyl) derivatisation

<400> SEQUENCE: 10
gtcgtgcagc ctccaggacc c                                             21

<210> SEQ ID NO 11
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide probe (HCV)
<220> FEATURE:
<221> NAME/KEY: modified_base
<222> LOCATION: (1)
<223> OTHER INFORMATION: Ruthenium3+ (tris bipyridyl) derivatisation

<400> SEQUENCE: 11
agaccaccaa atgcccct                                                       18

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide primer (HIV)
<220> FEATURE:
<221> NAME/KEY: modified_base
<222> LOCATION: (29)
<223> OTHER INFORMATION: derivatization with a p (t butyl)benzyl residue

<400> SEQUENCE: 12
agtgggggga catcaagcag ccatgcaaa                                           29

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide primer (HIV)
<220> FEATURE:
<221> NAME/KEY: modified_base
<222> LOCATION: (29)
<223> OTHER INFORMATION: derivatization with a p (t butyl)benzyl residue

<400> SEQUENCE: 13
agtgggggga caccaggcag caatgcaaa                                           29

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide primer (HIV reverse)
<220> FEATURE:
<221> NAME/KEY: modified_base
<222> LOCATION: (30)
<223> OTHER INFORMATION: derivatization with a p (t butyl)benzyl residue

<400> SEQUENCE: 14
ggtactagta gttcctgcta tgtcacttcc                                          30

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide primer (HCV forward)
<220> FEATURE:
<221> NAME/KEY: modified_base
<222> LOCATION: (26)
<223> OTHER INFORMATION: derivatization with a p (t butyl)benzyl residue

<400> SEQUENCE: 15
```

```
gcagaaagcg tctagccatg gcgtta                                             26
```

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide (HCV reverse)
<220> FEATURE:
<221> NAME/KEY: modified_base
<222> LOCATION: (28)
<223> OTHER INFORMATION: derivatization with a p (t butyl)benzyl residue

<400> SEQUENCE: 16

```
gcaagcaccc tatcaggcag taccacaa                                           28
```

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide primer (HBV forward)
<220> FEATURE:
<221> NAME/KEY: misc_feature
<222> LOCATION: (20)
<223> OTHER INFORMATION: n = i
<220> FEATURE:
<221> NAME/KEY: modified_base
<222> LOCATION: (28)
<223> OTHER INFORMATION: derivatization with a p (t butyl)benzyl residue

<400> SEQUENCE: 17

```
agaagtcaga aggcaaaaan gagagtaa                                           28
```

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide primer (HBV reverse)
<220> FEATURE:
<221> NAME/KEY: modified_base
<222> LOCATION: (27)
<223> OTHER INFORMATION: derivatization with a p (t butyl)benzyl residue

<400> SEQUENCE: 18

```
cacctctgcc taatcatctc ttgttca                                            27
```

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide probe (HIV)
<220> FEATURE:
<221> NAME/KEY: modified_base
<222> LOCATION: (1)
<223> OTHER INFORMATION: derivatisation with a
      Pentamethine di indocarbocyanine via a
      alkylphosphatidyl linker (Pharmacia Biotech
      Cy5 N ethyl phosphoramidite)
<220> FEATURE:
<221> NAME/KEY: misc_feature
<222> LOCATION: (10)
<223> OTHER INFORMATION: N represents a
      2 (amino cyclohexyl )propane 1,3 diol linker
      derivatised with 6 carboxy fluorescein (Biogenex
      CX FAM phosphoramidite)

```
<220> FEATURE:
<221> NAME/KEY: modified_base
<222> LOCATION: (31)
<223> OTHER INFORMATION: derivatisation with a 3' terminal phosphate
      group

<400> SEQUENCE: 19
tctgcagctn tcctcattga tggtatcttt ta                                   32

<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide probe (HCV)
<220> FEATURE:
<221> NAME/KEY: modified_base
<222> LOCATION: (1)
<223> OTHER INFORMATION: derivatisation with a
      Pentamethine di indocarbocyanine via a
      alkylphosphatidyl linker (Pharmacia Biotech
      Cy5 N ethyl phosphoramidite)
<220> FEATURE:
<221> NAME/KEY: misc_feature
<222> LOCATION: (15)
<223> OTHER INFORMATION: N represents a
      2 (amino cyclohexyl )propane 1,3 diol linker
      derivatised with 6 carboxy fluorescein (Biogenex
      CX FAM phosphoramidite)
<220> FEATURE:
<221> NAME/KEY: modified_base
<222> LOCATION: (31)
<223> OTHER INFORMATION: derivatisation with a 3' terminal phosphate
      group

<400> SEQUENCE: 20
cggtgtactc accgnttccg cagaccacta tg                                   32

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)
<223> OTHER INFORMATION: derivatisation with a
      Pentamethine di indocarbocyanine via a
      alkylphosphatidyl linker (Pharmacia Biotech
      Cy5 N ethyl phosphoramidite)
<220> FEATURE:
<221> NAME/KEY: misc_feature
<222> LOCATION: (17)
<223> OTHER INFORMATION: N represents a
      2 (amino cyclohexyl )propane 1,3 diol linker
      derivatised with 6 carboxy fluorescein (Biogenex
      CX FAM phosphoramidite)
<220> FEATURE:
<221> NAME/KEY: modified_base
<222> LOCATION: (32)
<223> OTHER INFORMATION: derivatisation with a 3' terminal phosphate
      group

<400> SEQUENCE: 21
ccaagctgtg ccttggntgg ctttggggca tgg                                  33

<210> SEQ ID NO 22
<211> LENGTH: 31
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (1)
<223> OTHER INFORMATION: derivatisation with a
      Pentamethine di indocarbocyanine via a
      alkylphosphatidyl linker (Pharmacia Biotech
      Cy5 N ethyl phosphoramidite)
<220> FEATURE:
<221> NAME/KEY: misc_feature
<222> LOCATION: (14)
<223> OTHER INFORMATION: N represents a
      2 (amino cyclohexyl )propane 1,3 diol linker
      derivatised with hexachloro 6 carboxy fluorescein
      (Biogenex CX HEX phosphoramidite)
<220> FEATURE:
<221> NAME/KEY: modified_base
<222> LOCATION: (30)
<223> OTHER INFORMATION: derivatisation with a 3' terminal phosphate
      group

<400> SEQUENCE: 22
tggactcagt cctntggtca tctcaccttc t                             31

<210> SEQ ID NO 23
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide  (Aptamer)
<220> FEATURE:
<221> NAME/KEY: modified_base
<222> LOCATION: (46)
<223> OTHER INFORMATION: derivatisation with a 3' terminal phosphate
      group

<400> SEQUENCE: 23
cgatcatctc agaacattct tagcgttttg ttcttgtgta tgatcg              46
```